US008217140B2

(12) United States Patent
Revets et al.

(10) Patent No.: US 8,217,140 B2
(45) Date of Patent: Jul. 10, 2012

(54) PEPTIDES CAPABLE OF BINDING TO SERUM PROTEINS AND COMPOUNDS, CONSTRUCTS AND POLYPEPTIDES COMPRISING THE SAME

(75) Inventors: Hilde Adi Pierrette Revets, Meise (BE); Carlo Boutton, Wielsbeke (BE); Stephanie Staelens, Wevelgem (BE); Peter Verheesen, Ghent (BE)

(73) Assignee: Ablynx N.V., Zwijnaarde (BE)

( * ) Notice: Subject to any disclaimer, the term of this patent is extended or adjusted under 35 U.S.C. 154(b) by 55 days.

(21) Appl. No.: 12/424,986

(22) Filed: Apr. 16, 2009

(65) Prior Publication Data

US 2009/0281277 A1     Nov. 12, 2009

Related U.S. Application Data

(60) Provisional application No. 61/045,690, filed on Apr. 17, 2008, provisional application No. 61/050,385, filed on May 5, 2008, provisional application No. 61/119,803, filed on Dec. 4, 2008.

(51) Int. Cl.
*C07K 2/10* (2006.01)
*C07K 4/10* (2006.01)

(52) U.S. Cl. ........................................ 530/326; 530/300

(58) Field of Classification Search ........................ None
See application file for complete search history.

(56) References Cited

U.S. PATENT DOCUMENTS

| 7,091,323 B2 * | 8/2006 | Pan et al. .................. 530/388.15 |
| 7,138,501 B2 * | 11/2006 | Ruben et al. ............. 530/388.23 |

FOREIGN PATENT DOCUMENTS

| EP | 0 361 991 A2 | 4/1990 |
| EP | 1 134 231 A1 | 9/2001 |
| EP | 1 433 793 A1 | 6/2004 |
| WO | WO 94/04678 A1 | 3/1994 |
| WO | WO 94/25591 A1 | 11/1994 |
| WO | WO 95/04079 A1 | 2/1995 |
| WO | WO 96/34103 A1 | 10/1996 |
| WO | WO 97/49805 A2 | 12/1997 |
| WO | WO 98/49185 A1 | 11/1998 |
| WO | WO 99/37681 A2 | 7/1999 |
| WO | WO 00/40968 A1 | 7/2000 |
| WO | WO 00/43507 A1 | 7/2000 |
| WO | WO 00/46383 A2 | 8/2000 |
| WO | WO 00/65057 A1 | 11/2000 |
| WO | WO 01/09300 A2 | 2/2001 |
| WO | WO 01/21817 A1 | 3/2001 |
| WO | WO 01/40310 A2 | 6/2001 |
| WO | WO 01/44301 A1 | 6/2001 |
| WO | WO 01/90190 A2 | 11/2001 |
| WO | WO 02/48193 A2 | 6/2002 |
| WO | WO 03/025020 A1 | 3/2003 |
| WO | WO 03/035694 A2 | 5/2003 |
| WO | WO 03/050531 A2 | 6/2003 |
| WO | WO 03/054016 A2 | 7/2003 |
| WO | WO 03/055527 A2 | 7/2003 |
| WO | WO 2004/003019 A2 | 1/2004 |
| WO | WO 2004/037999 A2 | 5/2004 |
| WO | WO 2004/041862 A2 | 5/2004 |
| WO | WO 2004/041863 A2 | 5/2004 |
| WO | WO 2004/041865 A2 | 5/2004 |
| WO | WO 2004/041867 A2 | 5/2004 |
| WO | WO 2004/062551 A2 | 7/2004 |
| WO | WO 2005/044858 A1 | 5/2005 |
| WO | WO 2005/118642 A2 | 12/2005 |
| WO | WO 2006/030220 A1 | 3/2006 |
| WO | WO 2006/038027 A2 | 4/2006 |
| WO | WO 2006/040153 A2 | 4/2006 |
| WO | WO 2006/059106 A2 | 6/2006 |
| WO | WO 2006/059108 A2 | 6/2006 |
| WO | WO 2006/079372 A1 | 8/2006 |
| WO | WO 2006/122786 A2 | 11/2006 |
| WO | WO 2006/122787 A1 | 11/2006 |
| WO | WO 2006/122825 A2 | 11/2006 |
| WO | WO 2007/042289 A2 | 4/2007 |
| WO | WO 2007/049017 A2 | 5/2007 |
| WO | WO 2007/063308 A2 | 6/2007 |
| WO | WO 2007/063311 A2 | 6/2007 |
| WO | WO 2007/066106 A1 | 6/2007 |
| WO | WO 2007/080392 A2 | 7/2007 |
| WO | WO 2007/085815 A2 | 8/2007 |
| WO | WO 2007/110219 A1 | 10/2007 |
| WO | WO 2008/020079 A1 | 2/2008 |
| WO | WO 2008/043821 A1 | 4/2008 |
| WO | WO 2008/043822 A2 | 4/2008 |
| WO | WO 2008/068280 A1 | 6/2008 |
| WO | WO 2008/074839 A2 | 6/2008 |
| WO | WO 2008/077945 A2 | 7/2008 |
| WO | WO 2008/101985 A2 | 8/2008 |
| WO | WO 2008/142164 A2 | 11/2008 |
| WO | WO 2008/148150 A1 | 12/2008 |
| WO | WO 2008/149144 A2 | 12/2008 |
| WO | WO 2008/149146 A2 | 12/2008 |
| WO | WO 2008/149147 A2 | 12/2008 |
| WO | WO 2008/149148 A2 | 12/2008 |
| WO | WO 2008/149149 A2 | 12/2008 |

OTHER PUBLICATIONS

Janeway et al., Immunobiology, 3rd ed. Garlend Press, 1997, p. 3:7-3:11.*

(Continued)

*Primary Examiner* — Yunsoo Kim
(74) *Attorney, Agent, or Firm* — Wolf, Greenfield & Sacks, P.C.

(57) ABSTRACT

The present invention relates to amino acid sequences that are capable of binding to serum proteins; to compounds, proteins, polypeptides, fusion proteins or constructs comprising or essentially consisting of such amino acid sequences; to nucleic acids that encode such amino acid sequences, compounds, proteins, polypeptides, fusion proteins or constructs; to compositions, and in particular pharmaceutical compositions, that comprise such amino acid sequences, compounds, proteins, polypeptides, fusion proteins or constructs; and to uses of such amino acid sequences, compounds, proteins, polypeptides, fusion proteins or constructs.

18 Claims, 18 Drawing Sheets

OTHER PUBLICATIONS

Fundamental Immunology, William E.Paul, M.D. 3rd Ed. 1993, p. 242.*
Portolano et al., J of Immunology, 1993, vol. 15, p. 880-887.*
Attwood, Science 2000; 290:471-473.*
Skolnick et al., Trends in Biotech. 2000; 18(1):34-39.*
Metzler et al.,Nature Structural Biol. 1997; 4:527-531.*
GenBank Submission; NIH/NCBI, Accession No. CAA00844; Fleer et al.; Sep. 2, 2002.
Chou et al., Conformational parameters for amino acids in helical, beta-sheet, and random coil regions calculated from proteins. Biochemistry. Jan. 15, 1974;13(2):211-22.
Decanniere et al., A single-domain antibody fragment in complex with RNase A: non-canonical loop structures and nanomolar affinity using two CDR loops. Structure. Apr. 15, 1999;7(4):361-70.
Dennis et al., Albumin binding as a general strategy for improving the pharmacokinetics of proteins. J Biol Chem. Sep. 20, 2002;277(38):35035-43. Epub Jul. 15, 2002.
Desmyter et al. Antigen specificity and high affinity binding provided by one single loop of a camel single-domain antibody. J Biol Chem. Jul. 13, 2001;276(28):26285-90. Epub May 7, 2001.
Desmyter et al., Crystal structure of a camel single-domain VH antibody fragment in complex with lysozyme. Nat Struct Biol. Sep. 1996;3(9):803-11.
Eisenberg et al., The hydrophobic moment detects periodicity in protein hydrophobicity. Proc Natl Acad Sci U S A. Jan. 1984;81(1):140-4.
Engelman et al., Identifying nonpolar transbilayer helices in amino acid sequences of membrane proteins. Annu Rev Biophys Biophys Chem. 1986;15:321-53.
Marquardt et al., A synthetic camel anti-lysozyme peptide antibody (peptibody) with flexible loop structure identified by high-resolution affinity mass spectrometry. Chemistry. Feb. 20, 2006;12(7):1915-23.
Minghetti et al., Molecular structure of the human albumin gene is revealed by nucleotide sequence within q11-22 of chromosome 4. J Biol Chem. May 25, 1986;261(15):6747-57.
Muyldermans et al., Single domain camel antibodies: current status. Rev Mol Biotechnol. Jun. 2001;74(4):277-302.
Nicaise et al., Affinity transfer by CDR grafting on a nonimmunoglobulin scaffold. Protein Sci. Jul. 2004;13(7):1882-91. Epub May 28, 2004.
Spinelli et al., The crystal structure of a llama heavy chain variable domain. Nat Struct Biol. Sep. 1996;3(9):752-7.

* cited by examiner

Figure 1

```
17D12 (comp.)      AASYSDYDVFGGGTDFGP
PMP56B2            AARYFDYDVFGGGTPAGD
PMP54D2            AARYFDYDVFGGGTDLGD
PMP56E6            AARYYDYDVFGGGTPLGG
PMP56F5            AARYYDYDVFGGGTPLGG
PMP56G6            AARYYDYDVFGGGTPLGG
PMP56E3            AARYYDYDVFGGGTPLGA
PMP56C3            AARYYDYDVFGGGTPLGA
PMP56E5            AARYYDYDVFGGGTPLGA
PMP54B2            AARYYDYDVFGGGTVVGE
PMP54C1            AARYYDYDVFGGGTRSGE
PMP56A6            AARYYDYDVFGGGTAGGQ
PMP56B4            AARYWDYDVFGGGTPVGG
PMP56E4            AARYWDYDVFGGGTPVGG
PMP56B1            AARYWDYDVFGGGTPQGE
PMP56C2            AARYWDYDVFGGGTPQGE
PMP56G2            AARYWDYDVFGGGTDPGG
PMP54D3            AARYLDYDVFGGGTQLGS
PMP54F3            AARYLDYDVFGGGTDVGS
PMP54C3            AARYLDYDVFGGGTPIGE
PMP54C2            AARYPDYDVFGGGTPVGG
PMP56C6            AARYPDYDVFGGGTPSGG
PMP54E2            AALYRDYDVFAGGTPGGG
PMP56B5            AALYRDYDVFGGGTPVGG
PMP56F6            AALYRDYDVFGGGTPVGG
PMP56A3            AALYDDYDVFGGGTPVGG
PMP56D6            AALYDDYDVFGGGTPVGG
PMP56B3            AAVYDDYDVFGGGTPVGG
PMP56C5            AAMYYDYDVFGGGTPTGA
PMP56F1            AAWYTDYDVFGGGTPQGG
PMP56H1            AAWYRDYDVFGGGTPLGA
PMP54B1            AAWYRDYDVFGGGTDEGS
PMP56H5            AAFYDDYDVFGGGTPAGG
```

Figure 1 (continued)

```
17D12 (comp.)    AASYSDYDVFGGGTDFGP
PMP56H3          AAFYWDYDVFGGGTDPGA
PMP56G3          AAFYWDYDVFGGGTDPGA
PMP56G1          AAYYFDYDVFGGGTPEGT
PMP56C1          AAYYFDYDVFGGGTPEGT
PMP54G1          AATYFDYDVFGGGTAVGS
PMP56G5          AAAYLDYDVFGGGTPVGG
PMP54H2          AAAYWDYDVFGGGTSAGT
PMP56B6          AAVYWDYDVFGGGTSLGD
PMP56H6          AAWYFDYDVFGGGTADGE
PMP56F3          AAWYFDYDVFGGGTADGE
PMP54G3          AAYYYDYDVFGGGTPGGE
PMP56A1          AADYYDYDVFGGGTSVGE
PMP56E1          AAYYYDYDVFGGGTPGGE
PMP56E2          AAYYYDYDVFGGGTPGGE
PMP56A5          AAYYRDYDVFGGGTPVGE
PMP54B3          AALYRDYDVFGGGTQVGE
PMP56D4          AALYKDYDVFGGGTPGGE
PMP56F2          AAPYRDYDVFGGGTPRGE
PMP56A2          AAPYHDYDVFGGGTPVGE
PMP54F2          AALYGDYDVFGGGTPLGE
PMP54H1          AASYLDYDVFGGGTPFGE
PMP54E1          AAFYRDYDVFGGGTGSGN
PMP54G2          AAIYRDYDVFGGGTPLGQ
PMP56D5          AATYYDYDVFGGGTPLGQ
PMP54H3          AASYRDYDVFGGGTPRGW
PMP54E3          AATYLDYDVFGGGTPDGR
PMP56A4          AAFYMDYDVFGGGTPRGQ
```

Figure 1 (continued)

```
17D12 (comp)    AASYSDYDVFGGGTDFGP
PMP54G5         AAPYFDYDVFGGGTARGG
PMP54F5         AAPYFDYDVFGGGTEVGG
PMP56A9         AAPYFDYDVFGGGTPMGG
PMP56B9         AARYYDYDVFGGGTPGGV
PMP56D7         AARYYDYDVFGGGTPGGV
PMP56H10        AARYYDYDVFGGGTSRGG
PMP56G10        VARYYDYDVFGGGTWSGD
PMP56G11        AVRYYDYDVFGGGTSVGG
PMP54G6         AALYYDYDVFGGGTPEGI
PMP56A10        AALYYDYDVFGGGTAAGS
PMP56A7         AALYYDYDVFGGGTPRGG
PMP56C7         AAYYYDYDVFGGGTALGG
PMP56B11        AADYYDYDVFGGGTVFGS
PMP56D8         AATYYDYDVFGGGTSLGN
PMP56G7         AALYYDYDVFGGGTYKGS
PMP54D6         AATYYDYDVFGGGTDGGS
PMP56C10        AARYWDYDVFGGGTPEGV
PMP54B5         AARYWDYDVFGGGTAQGE
PMP54E6         AARYWDYDVFGGGTPEGV
PMP56A8         AARYWDYDVFGGGTPEGV
PMP56B7         AARYWDYDVFGGGTPEGV
PMP56C9         AARYWDYDVFGGGTPEGI
PMP56D12        AARYWDYDVFGGGTPEGV
PMP56E8         AARYWDYDVFGGGTPEGV
PMP56F10        AGRYWDYDVFGGGTAQGA
PMP56G9         AGRYWDYDVFGGGTAQGA
PMP56E11        VAKYWDYDVFGGGTDSGG
PMP56F7         AASYWDYDVFGGGTPVGD
PMP56B12        AAQYWDYDVFGGGTPKGE
PMP54C6         AALYRDYDVFGGGTPVGG
PMP56A11        AALYRDYDVFGGGTSAGV
PMP56B10        AALYRDYDVFGGGTPSGV
```

Figure 1 (continued)

```
PMP56D11        AALYRDYDVFGGGTPKGE
PMP56D9         AALYRDYDVFGGGTPKGE
PMP56C8         AALYRDYDVFGGGTPSGV
PMP56E9         AALYRDYDVFGGGTPSGV
PMP56F11        AALYRDYDVFGGGTPRGG
PMP56F9         AALYRDYDVFGGGTPKGE
PMP56H7         AALYRDYDVFGGGTPVGG
PMP56H9         AALYRDYDVFGGGTPRGS
PMP56H11        AAFYRDYDVFGGGTPKGG
PMP56A12        AAFYRDYDVFGGGTPKGG
PMP54H5         AAFYRDYDVFGGGTDMGN
PMP54E5         AAWYRDYDVFGGGTPLGA
PMP56D10        AAWYRDYDVFGGGTPLGA
PMP54H4         AARYPDYDVFGGGTSMGQ
PMP54B6         AAMYDDYDVFGGGTPSGA
PMP54C5         AAYYLDYDVFGGGTPGGG
PMP54F6         AAFYDDYDVFGGGTPAGG
PMP54H6         AASYLDYDVFGGGTPGGG
PMP56B8         AAPYLDYDVFGGGTPEGS
PMP56C12        AALYSDYDVFGGGTPPGV
PMP56E10        AAPYPDYDVFGGGTPQGS
PMP56E12        AAMYDDYDVFGGGTPSGA
01B3            AALYDDYDVFGGGTPAGG
```

Figure 2: Phage ELISA
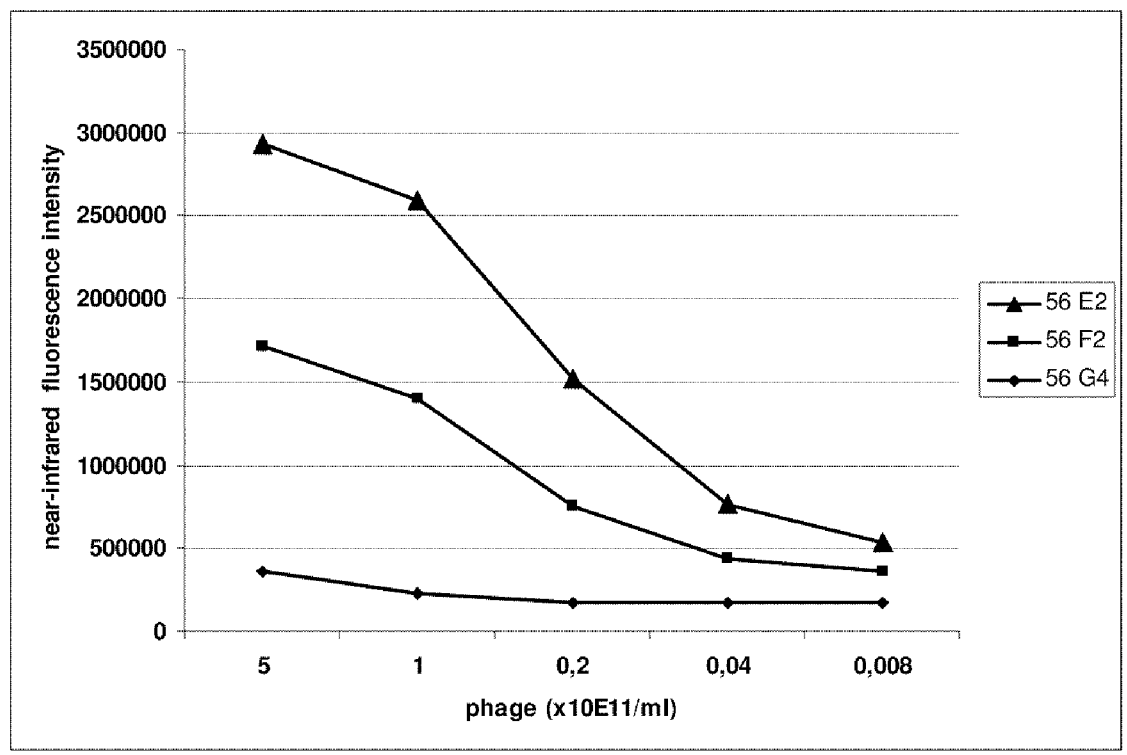

Figure 3: Solution binding competition assay
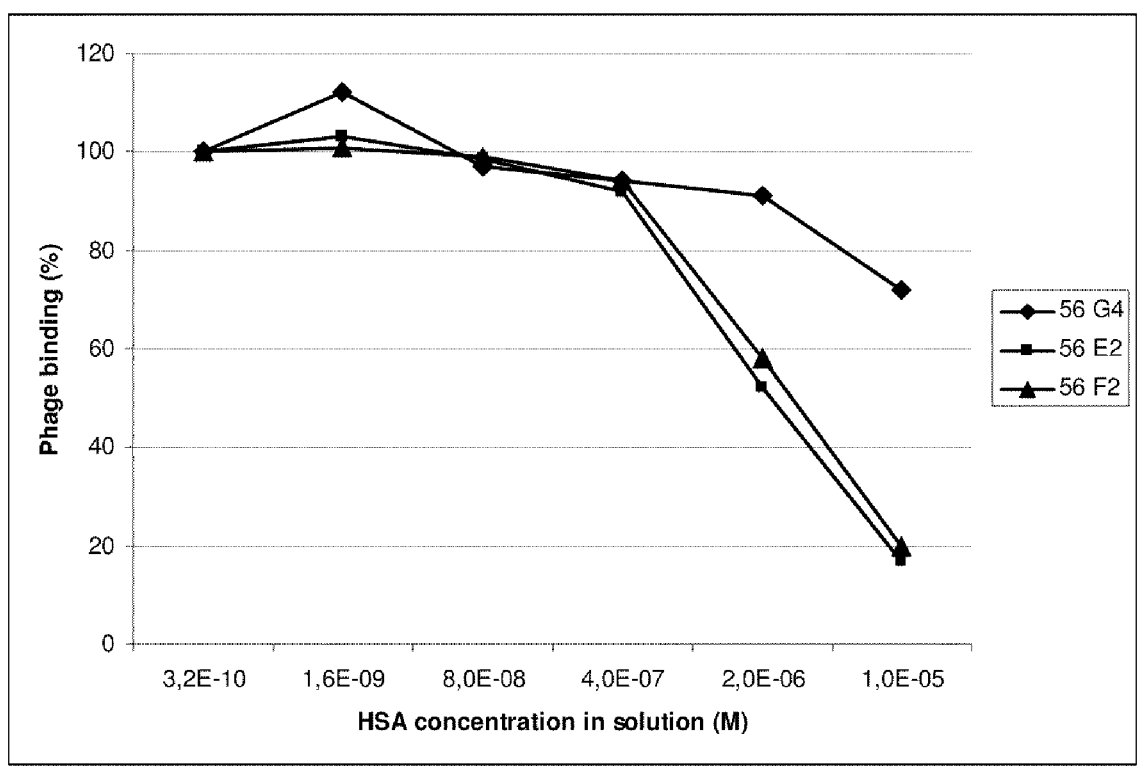

SEQUENCE LISTING

```
<160> NUMBER OF SEQ ID NOS: 194

<210> SEQ ID NO 1
<211> LENGTH: 18
<212> TYPE: PRT
<213> ORGANISM: Artificial
<220> FEATURE:
<223> OTHER INFORMATION: synthetic amino acid sequence

<400> SEQUENCE: 1

Ala Ala Ser Tyr Ser Asp Tyr Asp Val Phe Gly Gly Gly Thr Asp Phe
1               5                   10                  15

Gly Pro

<210> SEQ ID NO 2
<211> LENGTH: 18
<212> TYPE: PRT
<213> ORGANISM: Artificial
<220> FEATURE:
<223> OTHER INFORMATION: synthetic amino acid sequence
```

```
<400> SEQUENCE: 2

Ala Ala Arg Tyr Phe Asp Tyr Asp Val Phe Gly Gly Gly Thr Pro Ala
1               5                   10                  15

Gly Asp

<210> SEQ ID NO 3
<211> LENGTH: 18
<212> TYPE: PRT
<213> ORGANISM: Artificial
<220> FEATURE:
<223> OTHER INFORMATION: synthetic amino acid sequence

<400> SEQUENCE: 3

Ala Ala Arg Tyr Phe Asp Tyr Asp Val Phe Gly Gly Gly Thr Asp Leu
1               5                   10                  15

Gly Asp

<210> SEQ ID NO 4
<211> LENGTH: 18
<212> TYPE: PRT
<213> ORGANISM: Artificial
<220> FEATURE:
<223> OTHER INFORMATION: synthetic amino acid sequence

<400> SEQUENCE: 4

Ala Ala Arg Tyr Tyr Asp Tyr Asp Val Phe Gly Gly Gly Thr Pro Leu
1               5                   10                  15

Gly Gly

<210> SEQ ID NO 5
<211> LENGTH: 18
<212> TYPE: PRT
<213> ORGANISM: Artificial
<220> FEATURE:
<223> OTHER INFORMATION: synthetic amino acid sequence

<400> SEQUENCE: 5

Ala Ala Arg Tyr Tyr Asp Tyr Asp Val Phe Gly Gly Gly Thr Pro Leu
1               5                   10                  15

Gly Gly

<210> SEQ ID NO 6
<211> LENGTH: 18
<212> TYPE: PRT
<213> ORGANISM: Artificial
<220> FEATURE:
<223> OTHER INFORMATION: synthetic amino acid sequence

<400> SEQUENCE: 6

Ala Ala Arg Tyr Tyr Asp Tyr Asp Val Phe Gly Gly Gly Thr Pro Leu
1               5                   10                  15

Gly Gly

<210> SEQ ID NO 7
<211> LENGTH: 18
<212> TYPE: PRT
<213> ORGANISM: Artificial
<220> FEATURE:
<223> OTHER INFORMATION: synthetic amino acid sequence

<400> SEQUENCE: 7

Ala Ala Arg Tyr Tyr Asp Tyr Asp Val Phe Gly Gly Gly Thr Pro Leu
1               5                   10                  15
```

Gly Ala

<210> SEQ ID NO 8
<211> LENGTH: 18
<212> TYPE: PRT
<213> ORGANISM: Artificial
<220> FEATURE:
<223> OTHER INFORMATION: synthetic amino acid sequence

<400> SEQUENCE: 8

```
Ala Ala Arg Tyr Tyr Asp Tyr Asp Val Phe Gly Gly Gly Thr Pro Leu
1               5                   10                  15
Gly Ala
```

<210> SEQ ID NO 9
<211> LENGTH: 18
<212> TYPE: PRT
<213> ORGANISM: Artificial
<220> FEATURE:
<223> OTHER INFORMATION: synthetic amino acid sequence

<400> SEQUENCE: 9

```
Ala Ala Arg Tyr Tyr Asp Tyr Asp Val Phe Gly Gly Gly Thr Pro Leu
1               5                   10                  15
Gly Ala
```

<210> SEQ ID NO 10
<211> LENGTH: 18
<212> TYPE: PRT
<213> ORGANISM: Artificial
<220> FEATURE:
<223> OTHER INFORMATION: synthetic amino acid sequence

<400> SEQUENCE: 10

```
Ala Ala Arg Tyr Tyr Asp Tyr Asp Val Phe Gly Gly Gly Thr Val Val
1               5                   10                  15
Gly Glu
```

<210> SEQ ID NO 11
<211> LENGTH: 18
<212> TYPE: PRT
<213> ORGANISM: Artificial
<220> FEATURE:
<223> OTHER INFORMATION: synthetic amino acid sequence

<400> SEQUENCE: 11

```
Ala Ala Arg Tyr Tyr Asp Tyr Asp Val Phe Gly Gly Gly Thr Arg Ser
1               5                   10                  15
Gly Glu
```

<210> SEQ ID NO 12
<211> LENGTH: 18
<212> TYPE: PRT
<213> ORGANISM: Artificial
<220> FEATURE:
<223> OTHER INFORMATION: synthetic amino acid sequence

<400> SEQUENCE: 12

```
Ala Ala Arg Tyr Tyr Asp Tyr Asp Val Phe Gly Gly Gly Thr Ala Gly
1               5                   10                  15
Gly Gln
```

<210> SEQ ID NO 13
<211> LENGTH: 18

```
<212> TYPE: PRT
<213> ORGANISM: Artificial
<220> FEATURE:
<223> OTHER INFORMATION: synthetic amino acid sequence

<400> SEQUENCE: 13

Ala Ala Arg Tyr Trp Asp Tyr Asp Val Phe Gly Gly Gly Thr Pro Val
1               5                   10                  15

Gly Gly

<210> SEQ ID NO 14
<211> LENGTH: 18
<212> TYPE: PRT
<213> ORGANISM: Artificial
<220> FEATURE:
<223> OTHER INFORMATION: synthetic amino acid sequence

<400> SEQUENCE: 14

Ala Ala Arg Tyr Trp Asp Tyr Asp Val Phe Gly Gly Gly Thr Pro Val
1               5                   10                  15

Gly Gly

<210> SEQ ID NO 15
<211> LENGTH: 18
<212> TYPE: PRT
<213> ORGANISM: Artificial
<220> FEATURE:
<223> OTHER INFORMATION: synthetic amino acid sequence

<400> SEQUENCE: 15

Ala Ala Arg Tyr Trp Asp Tyr Asp Val Phe Gly Gly Gly Thr Pro Gln
1               5                   10                  15

Gly Glu

<210> SEQ ID NO 16
<211> LENGTH: 18
<212> TYPE: PRT
<213> ORGANISM: Artificial
<220> FEATURE:
<223> OTHER INFORMATION: synthetic amino acid sequence

<400> SEQUENCE: 16

Ala Ala Arg Tyr Trp Asp Tyr Asp Val Phe Gly Gly Gly Thr Pro Gln
1               5                   10                  15

Gly Glu

<210> SEQ ID NO 17
<211> LENGTH: 18
<212> TYPE: PRT
<213> ORGANISM: Artificial
<220> FEATURE:
<223> OTHER INFORMATION: synthetic amino acid sequence

<400> SEQUENCE: 17

Ala Ala Arg Tyr Trp Asp Tyr Asp Val Phe Gly Gly Gly Thr Asp Pro
1               5                   10                  15

Gly Gly

<210> SEQ ID NO 18
<211> LENGTH: 18
<212> TYPE: PRT
<213> ORGANISM: Artificial
<220> FEATURE:
<223> OTHER INFORMATION: synthetic amino acid sequence
```

```
<400> SEQUENCE: 18

Ala Ala Arg Tyr Leu Asp Tyr Asp Val Phe Gly Gly Gly Thr Gln Leu
1               5                   10                  15

Gly Ser

<210> SEQ ID NO 19
<211> LENGTH: 18
<212> TYPE: PRT
<213> ORGANISM: Artificial
<220> FEATURE:
<223> OTHER INFORMATION: synthetic amino acid sequence

<400> SEQUENCE: 19

Ala Ala Arg Tyr Leu Asp Tyr Asp Val Phe Gly Gly Gly Thr Asp Val
1               5                   10                  15

Gly Ser

<210> SEQ ID NO 20
<211> LENGTH: 18
<212> TYPE: PRT
<213> ORGANISM: Artificial
<220> FEATURE:
<223> OTHER INFORMATION: synthetic amino acid sequence

<400> SEQUENCE: 20

Ala Ala Arg Tyr Leu Asp Tyr Asp Val Phe Gly Gly Gly Thr Pro Ile
1               5                   10                  15

Gly Glu

<210> SEQ ID NO 21
<211> LENGTH: 18
<212> TYPE: PRT
<213> ORGANISM: Artificial
<220> FEATURE:
<223> OTHER INFORMATION: synthetic amino acid sequence

<400> SEQUENCE: 21

Ala Ala Arg Tyr Pro Asp Tyr Asp Val Phe Gly Gly Gly Thr Pro Val
1               5                   10                  15

Gly Gly

<210> SEQ ID NO 22
<211> LENGTH: 18
<212> TYPE: PRT
<213> ORGANISM: Artificial
<220> FEATURE:
<223> OTHER INFORMATION: synthetic amino acid sequence

<400> SEQUENCE: 22

Ala Ala Arg Tyr Pro Asp Tyr Asp Val Phe Gly Gly Gly Thr Pro Ser
1               5                   10                  15

Gly Gly

<210> SEQ ID NO 23
<211> LENGTH: 18
<212> TYPE: PRT
<213> ORGANISM: Artificial
<220> FEATURE:
<223> OTHER INFORMATION: synthetic amino acid sequence

<400> SEQUENCE: 23

Ala Ala Leu Tyr Arg Asp Tyr Asp Val Phe Ala Gly Gly Thr Pro Gly
1               5                   10                  15
```

Gly Gly

```
<210> SEQ ID NO 24
<211> LENGTH: 18
<212> TYPE: PRT
<213> ORGANISM: Artificial
<220> FEATURE:
<223> OTHER INFORMATION: synthetic amino acid sequence

<400> SEQUENCE: 24

Ala Ala Leu Tyr Arg Asp Tyr Asp Val Phe Gly Gly Gly Thr Pro Val
1               5                   10                  15

Gly Gly

<210> SEQ ID NO 25
<211> LENGTH: 18
<212> TYPE: PRT
<213> ORGANISM: Artificial
<220> FEATURE:
<223> OTHER INFORMATION: synthetic amino acid sequence

<400> SEQUENCE: 25

Ala Ala Leu Tyr Arg Asp Tyr Asp Val Phe Gly Gly Gly Thr Pro Val
1               5                   10                  15

Gly Gly

<210> SEQ ID NO 26
<211> LENGTH: 18
<212> TYPE: PRT
<213> ORGANISM: Artificial
<220> FEATURE:
<223> OTHER INFORMATION: synthetic amino acid sequence

<400> SEQUENCE: 26

Ala Ala Leu Tyr Asp Asp Tyr Asp Val Phe Gly Gly Gly Thr Pro Val
1               5                   10                  15

Gly Gly

<210> SEQ ID NO 27
<211> LENGTH: 18
<212> TYPE: PRT
<213> ORGANISM: Artificial
<220> FEATURE:
<223> OTHER INFORMATION: synthetic amino acid sequence

<400> SEQUENCE: 27

Ala Ala Leu Tyr Asp Asp Tyr Asp Val Phe Gly Gly Gly Thr Pro Val
1               5                   10                  15

Gly Gly

<210> SEQ ID NO 28
<211> LENGTH: 18
<212> TYPE: PRT
<213> ORGANISM: Artificial
<220> FEATURE:
<223> OTHER INFORMATION: synthetic amino acid sequence

<400> SEQUENCE: 28

Ala Ala Val Tyr Asp Asp Tyr Asp Val Phe Gly Gly Gly Thr Pro Val
1               5                   10                  15

Gly Gly

<210> SEQ ID NO 29
<211> LENGTH: 18
```

```
<212> TYPE: PRT
<213> ORGANISM: Artificial
<220> FEATURE:
<223> OTHER INFORMATION: synthetic amino acid sequence

<400> SEQUENCE: 29

Ala Ala Met Tyr Tyr Asp Tyr Asp Val Phe Gly Gly Gly Thr Pro Thr
1               5                   10                  15

Gly Ala

<210> SEQ ID NO 30
<211> LENGTH: 18
<212> TYPE: PRT
<213> ORGANISM: Artificial
<220> FEATURE:
<223> OTHER INFORMATION: synthetic amino acid sequence

<400> SEQUENCE: 30

Ala Ala Trp Tyr Thr Asp Tyr Asp Val Phe Gly Gly Gly Thr Pro Gln
1               5                   10                  15

Gly Gly

<210> SEQ ID NO 31
<211> LENGTH: 18
<212> TYPE: PRT
<213> ORGANISM: Artificial
<220> FEATURE:
<223> OTHER INFORMATION: synthetic amino acid sequence

<400> SEQUENCE: 31

Ala Ala Trp Tyr Arg Asp Tyr Asp Val Phe Gly Gly Gly Thr Pro Leu
1               5                   10                  15

Gly Ala

<210> SEQ ID NO 32
<211> LENGTH: 18
<212> TYPE: PRT
<213> ORGANISM: Artificial
<220> FEATURE:
<223> OTHER INFORMATION: synthetic amino acid sequence

<400> SEQUENCE: 32

Ala Ala Trp Tyr Arg Asp Tyr Asp Val Phe Gly Gly Gly Thr Asp Glu
1               5                   10                  15

Gly Ser

<210> SEQ ID NO 33
<211> LENGTH: 18
<212> TYPE: PRT
<213> ORGANISM: Artificial
<220> FEATURE:
<223> OTHER INFORMATION: synthetic amino acid sequence

<400> SEQUENCE: 33

Ala Ala Phe Tyr Asp Asp Tyr Asp Val Phe Gly Gly Gly Thr Pro Ala
1               5                   10                  15

Gly Gly

<210> SEQ ID NO 34
<211> LENGTH: 18
<212> TYPE: PRT
<213> ORGANISM: Artificial
<220> FEATURE:
<223> OTHER INFORMATION: synthetic amino acid sequence
```

```
<400> SEQUENCE: 34

Ala Ala Phe Tyr Trp Asp Tyr Asp Val Phe Gly Gly Gly Thr Asp Pro
1               5                   10                  15

Gly Ala

<210> SEQ ID NO 35
<211> LENGTH: 18
<212> TYPE: PRT
<213> ORGANISM: Artificial
<220> FEATURE:
<223> OTHER INFORMATION: synthetic amino acid sequence

<400> SEQUENCE: 35

Ala Ala Phe Tyr Trp Asp Tyr Asp Val Phe Gly Gly Gly Thr Asp Pro
1               5                   10                  15

Gly Ala

<210> SEQ ID NO 36
<211> LENGTH: 18
<212> TYPE: PRT
<213> ORGANISM: Artificial
<220> FEATURE:
<223> OTHER INFORMATION: synthetic amino acid sequence

<400> SEQUENCE: 36

Ala Ala Tyr Tyr Phe Asp Tyr Asp Val Phe Gly Gly Gly Thr Pro Glu
1               5                   10                  15

Gly Thr

<210> SEQ ID NO 37
<211> LENGTH: 18
<212> TYPE: PRT
<213> ORGANISM: Artificial
<220> FEATURE:
<223> OTHER INFORMATION: synthetic amino acid sequence

<400> SEQUENCE: 37

Ala Ala Tyr Tyr Phe Asp Tyr Asp Val Phe Gly Gly Gly Thr Pro Glu
1               5                   10                  15

Gly Thr

<210> SEQ ID NO 38
<211> LENGTH: 18
<212> TYPE: PRT
<213> ORGANISM: Artificial
<220> FEATURE:
<223> OTHER INFORMATION: synthetic amino acid sequence

<400> SEQUENCE: 38

Ala Ala Thr Tyr Phe Asp Tyr Asp Val Phe Gly Gly Gly Thr Ala Val
1               5                   10                  15

Gly Ser

<210> SEQ ID NO 39
<211> LENGTH: 18
<212> TYPE: PRT
<213> ORGANISM: Artificial
<220> FEATURE:
<223> OTHER INFORMATION: synthetic amino acid sequence

<400> SEQUENCE: 39

Ala Ala Ala Tyr Leu Asp Tyr Asp Val Phe Gly Gly Gly Thr Pro Val
1               5                   10                  15
```

Gly Gly

<210> SEQ ID NO 40
<211> LENGTH: 18
<212> TYPE: PRT
<213> ORGANISM: Artificial
<220> FEATURE:
<223> OTHER INFORMATION: synthetic amino acid sequence

<400> SEQUENCE: 40

Ala Ala Ala Tyr Trp Asp Tyr Asp Val Phe Gly Gly Gly Thr Ser Ala
1               5                   10                  15

Gly Thr

<210> SEQ ID NO 41
<211> LENGTH: 18
<212> TYPE: PRT
<213> ORGANISM: Artificial
<220> FEATURE:
<223> OTHER INFORMATION: synthetic amino acid sequence

<400> SEQUENCE: 41

Ala Ala Val Tyr Trp Asp Tyr Asp Val Phe Gly Gly Gly Thr Ser Leu
1               5                   10                  15

Gly Asp

<210> SEQ ID NO 42
<211> LENGTH: 18
<212> TYPE: PRT
<213> ORGANISM: Artificial
<220> FEATURE:
<223> OTHER INFORMATION: synthetic amino acid sequence

<400> SEQUENCE: 42

Ala Ala Trp Tyr Phe Asp Tyr Asp Val Phe Gly Gly Gly Thr Ala Asp
1               5                   10                  15

Gly Glu

<210> SEQ ID NO 43
<211> LENGTH: 18
<212> TYPE: PRT
<213> ORGANISM: Artificial
<220> FEATURE:
<223> OTHER INFORMATION: synthetic amino acid sequence

<400> SEQUENCE: 43

Ala Ala Trp Tyr Phe Asp Tyr Asp Val Phe Gly Gly Gly Thr Ala Asp
1               5                   10                  15

Gly Glu

<210> SEQ ID NO 44
<211> LENGTH: 18
<212> TYPE: PRT
<213> ORGANISM: Artificial
<220> FEATURE:
<223> OTHER INFORMATION: synthetic amino acid sequence

<400> SEQUENCE: 44

Ala Ala Tyr Tyr Tyr Asp Tyr Asp Val Phe Gly Gly Gly Thr Pro Gly
1               5                   10                  15

Gly Glu

<210> SEQ ID NO 45
<211> LENGTH: 18

```
<212> TYPE: PRT
<213> ORGANISM: Artificial
<220> FEATURE:
<223> OTHER INFORMATION: synthetic amino acid sequence

<400> SEQUENCE: 45

Ala Ala Asp Tyr Tyr Asp Tyr Asp Val Phe Gly Gly Gly Thr Ser Val
1               5                   10                  15

Gly Glu

<210> SEQ ID NO 46
<211> LENGTH: 18
<212> TYPE: PRT
<213> ORGANISM: Artificial
<220> FEATURE:
<223> OTHER INFORMATION: synthetic amino acid sequence

<400> SEQUENCE: 46

Ala Ala Tyr Tyr Tyr Asp Tyr Asp Val Phe Gly Gly Gly Thr Pro Gly
1               5                   10                  15

Gly Glu

<210> SEQ ID NO 47
<211> LENGTH: 18
<212> TYPE: PRT
<213> ORGANISM: Artificial
<220> FEATURE:
<223> OTHER INFORMATION: synthetic amino acid sequence

<400> SEQUENCE: 47

Ala Ala Tyr Tyr Tyr Asp Tyr Asp Val Phe Gly Gly Gly Thr Pro Gly
1               5                   10                  15

Gly Glu

<210> SEQ ID NO 48
<211> LENGTH: 18
<212> TYPE: PRT
<213> ORGANISM: Artificial
<220> FEATURE:
<223> OTHER INFORMATION: synthetic amino acid sequence

<400> SEQUENCE: 48

Ala Ala Tyr Tyr Arg Asp Tyr Asp Val Phe Gly Gly Gly Thr Pro Val
1               5                   10                  15

Gly Glu

<210> SEQ ID NO 49
<211> LENGTH: 18
<212> TYPE: PRT
<213> ORGANISM: Artificial
<220> FEATURE:
<223> OTHER INFORMATION: synthetic amino acid sequence

<400> SEQUENCE: 49

Ala Ala Leu Tyr Arg Asp Tyr Asp Val Phe Gly Gly Gly Thr Gln Val
1               5                   10                  15

Gly Glu

<210> SEQ ID NO 50
<211> LENGTH: 18
<212> TYPE: PRT
<213> ORGANISM: Artificial
<220> FEATURE:
<223> OTHER INFORMATION: synthetic amino acid sequence
```

```
<400> SEQUENCE: 50

Ala Ala Leu Tyr Lys Asp Tyr Asp Val Phe Gly Gly Gly Thr Pro Gly
1               5                   10                  15

Gly Glu

<210> SEQ ID NO 51
<211> LENGTH: 18
<212> TYPE: PRT
<213> ORGANISM: Artificial
<220> FEATURE:
<223> OTHER INFORMATION: synthetic amino acid sequence

<400> SEQUENCE: 51

Ala Ala Pro Tyr Arg Asp Tyr Asp Val Phe Gly Gly Gly Thr Pro Arg
1               5                   10                  15

Gly Glu

<210> SEQ ID NO 52
<211> LENGTH: 18
<212> TYPE: PRT
<213> ORGANISM: Artificial
<220> FEATURE:
<223> OTHER INFORMATION: synthetic amino acid sequence

<400> SEQUENCE: 52

Ala Ala Pro Tyr His Asp Tyr Asp Val Phe Gly Gly Gly Thr Pro Val
1               5                   10                  15

Gly Glu

<210> SEQ ID NO 53
<211> LENGTH: 18
<212> TYPE: PRT
<213> ORGANISM: Artificial
<220> FEATURE:
<223> OTHER INFORMATION: synthetic amino acid sequence

<400> SEQUENCE: 53

Ala Ala Leu Tyr Gly Asp Tyr Asp Val Phe Gly Gly Gly Thr Pro Leu
1               5                   10                  15

Gly Glu

<210> SEQ ID NO 54
<211> LENGTH: 18
<212> TYPE: PRT
<213> ORGANISM: Artificial
<220> FEATURE:
<223> OTHER INFORMATION: synthetic amino acid sequence

<400> SEQUENCE: 54

Ala Ala Ser Tyr Leu Asp Tyr Asp Val Phe Gly Gly Gly Thr Pro Phe
1               5                   10                  15

Gly Glu

<210> SEQ ID NO 55
<211> LENGTH: 18
<212> TYPE: PRT
<213> ORGANISM: Artificial
<220> FEATURE:
<223> OTHER INFORMATION: synthetic amino acid sequence

<400> SEQUENCE: 55

Ala Ala Phe Tyr Arg Asp Tyr Asp Val Phe Gly Gly Gly Thr Gly Ser
1               5                   10                  15
```

Gly Asn

```
<210> SEQ ID NO 56
<211> LENGTH: 18
<212> TYPE: PRT
<213> ORGANISM: Artificial
<220> FEATURE:
<223> OTHER INFORMATION: synthetic amino acid sequence

<400> SEQUENCE: 56

Ala Ala Ile Tyr Arg Asp Tyr Asp Val Phe Gly Gly Gly Thr Pro Leu
1               5                   10                  15

Gly Gln

<210> SEQ ID NO 57
<211> LENGTH: 18
<212> TYPE: PRT
<213> ORGANISM: Artificial
<220> FEATURE:
<223> OTHER INFORMATION: synthetic amino acid sequence

<400> SEQUENCE: 57

Ala Ala Thr Tyr Tyr Asp Tyr Asp Val Phe Gly Gly Gly Thr Pro Leu
1               5                   10                  15

Gly Gln

<210> SEQ ID NO 58
<211> LENGTH: 18
<212> TYPE: PRT
<213> ORGANISM: Artificial
<220> FEATURE:
<223> OTHER INFORMATION: synthetic amino acid sequence

<400> SEQUENCE: 58

Ala Ala Ser Tyr Arg Asp Tyr Asp Val Phe Gly Gly Gly Thr Pro Arg
1               5                   10                  15

Gly Trp

<210> SEQ ID NO 59
<211> LENGTH: 18
<212> TYPE: PRT
<213> ORGANISM: Artificial
<220> FEATURE:
<223> OTHER INFORMATION: synthetic amino acid sequence

<400> SEQUENCE: 59

Ala Ala Thr Tyr Leu Asp Tyr Asp Val Phe Gly Gly Gly Thr Pro Asp
1               5                   10                  15

Gly Arg

<210> SEQ ID NO 60
<211> LENGTH: 18
<212> TYPE: PRT
<213> ORGANISM: Artificial
<220> FEATURE:
<223> OTHER INFORMATION: synthetic amino acid sequence

<400> SEQUENCE: 60

Ala Ala Phe Tyr Met Asp Tyr Asp Val Phe Gly Gly Gly Thr Pro Arg
1               5                   10                  15

Gly Gln

<210> SEQ ID NO 61
<211> LENGTH: 18
```

-continued

```
<212> TYPE: PRT
<213> ORGANISM: Artificial
<220> FEATURE:
<223> OTHER INFORMATION: synthetic amino acid sequence

<400> SEQUENCE: 61

Ala Ala Pro Tyr Phe Asp Tyr Asp Val Phe Gly Gly Gly Thr Ala Arg
1               5                   10                  15

Gly Gly

<210> SEQ ID NO 62
<211> LENGTH: 18
<212> TYPE: PRT
<213> ORGANISM: Artificial
<220> FEATURE:
<223> OTHER INFORMATION: synthetic amino acid sequence

<400> SEQUENCE: 62

Ala Ala Pro Tyr Phe Asp Tyr Asp Val Phe Gly Gly Gly Thr Glu Val
1               5                   10                  15

Gly Gly

<210> SEQ ID NO 63
<211> LENGTH: 18
<212> TYPE: PRT
<213> ORGANISM: Artificial
<220> FEATURE:
<223> OTHER INFORMATION: synthetic amino acid sequence

<400> SEQUENCE: 63

Ala Ala Pro Tyr Phe Asp Tyr Asp Val Phe Gly Gly Gly Thr Pro Met
1               5                   10                  15

Gly Gly

<210> SEQ ID NO 64
<211> LENGTH: 18
<212> TYPE: PRT
<213> ORGANISM: Artificial
<220> FEATURE:
<223> OTHER INFORMATION: synthetic amino acid sequence

<400> SEQUENCE: 64

Ala Ala Arg Tyr Tyr Asp Tyr Asp Val Phe Gly Gly Gly Thr Pro Gly
1               5                   10                  15

Gly Val

<210> SEQ ID NO 65
<211> LENGTH: 18
<212> TYPE: PRT
<213> ORGANISM: Artificial
<220> FEATURE:
<223> OTHER INFORMATION: synthetic amino acid sequence

<400> SEQUENCE: 65

Ala Ala Arg Tyr Tyr Asp Tyr Asp Val Phe Gly Gly Gly Thr Pro Gly
1               5                   10                  15

Gly Val

<210> SEQ ID NO 66
<211> LENGTH: 18
<212> TYPE: PRT
<213> ORGANISM: Artificial
<220> FEATURE:
<223> OTHER INFORMATION: synthetic amino acid sequence
```

-continued

```
<400> SEQUENCE: 66

Ala Ala Arg Tyr Tyr Asp Tyr Asp Val Phe Gly Gly Gly Thr Ser Arg
1               5                   10                  15

Gly Gly

<210> SEQ ID NO 67
<211> LENGTH: 18
<212> TYPE: PRT
<213> ORGANISM: Artificial
<220> FEATURE:
<223> OTHER INFORMATION: synthetic amino acid sequence

<400> SEQUENCE: 67

Val Ala Arg Tyr Tyr Asp Tyr Asp Val Phe Gly Gly Gly Thr Trp Ser
1               5                   10                  15

Gly Asp

<210> SEQ ID NO 68
<211> LENGTH: 18
<212> TYPE: PRT
<213> ORGANISM: Artificial
<220> FEATURE:
<223> OTHER INFORMATION: synthetic amino acid sequence

<400> SEQUENCE: 68

Ala Val Arg Tyr Tyr Asp Tyr Asp Val Phe Gly Gly Gly Thr Ser Val
1               5                   10                  15

Gly Gly

<210> SEQ ID NO 69
<211> LENGTH: 18
<212> TYPE: PRT
<213> ORGANISM: Artificial
<220> FEATURE:
<223> OTHER INFORMATION: synthetic amino acid sequence

<400> SEQUENCE: 69

Ala Ala Leu Tyr Tyr Asp Tyr Asp Val Phe Gly Gly Gly Thr Pro Glu
1               5                   10                  15

Gly Ile

<210> SEQ ID NO 70
<211> LENGTH: 18
<212> TYPE: PRT
<213> ORGANISM: Artificial
<220> FEATURE:
<223> OTHER INFORMATION: synthetic amino acid sequence

<400> SEQUENCE: 70

Ala Ala Leu Tyr Tyr Asp Tyr Asp Val Phe Gly Gly Gly Thr Ala Ala
1               5                   10                  15

Gly Ser

<210> SEQ ID NO 71
<211> LENGTH: 18
<212> TYPE: PRT
<213> ORGANISM: Artificial
<220> FEATURE:
<223> OTHER INFORMATION: synthetic amino acid sequence

<400> SEQUENCE: 71

Ala Ala Leu Tyr Tyr Asp Tyr Asp Val Phe Gly Gly Gly Thr Pro Arg
1               5                   10                  15
```

Gly Gly

<210> SEQ ID NO 72
<211> LENGTH: 18
<212> TYPE: PRT
<213> ORGANISM: Artificial
<220> FEATURE:
<223> OTHER INFORMATION: synthetic amino acid sequence

<400> SEQUENCE: 72

Ala Ala Tyr Tyr Tyr Asp Tyr Asp Val Phe Gly Gly Gly Thr Ala Leu
1               5                   10                  15

Gly Gly

<210> SEQ ID NO 73
<211> LENGTH: 18
<212> TYPE: PRT
<213> ORGANISM: Artificial
<220> FEATURE:
<223> OTHER INFORMATION: synthetic amino acid sequence

<400> SEQUENCE: 73

Ala Ala Asp Tyr Tyr Asp Tyr Asp Val Phe Gly Gly Gly Thr Val Phe
1               5                   10                  15

Gly Ser

<210> SEQ ID NO 74
<211> LENGTH: 18
<212> TYPE: PRT
<213> ORGANISM: Artificial
<220> FEATURE:
<223> OTHER INFORMATION: synthetic amino acid sequence

<400> SEQUENCE: 74

Ala Ala Thr Tyr Tyr Asp Tyr Asp Val Phe Gly Gly Gly Thr Ser Leu
1               5                   10                  15

Gly Asn

<210> SEQ ID NO 75
<211> LENGTH: 18
<212> TYPE: PRT
<213> ORGANISM: Artificial
<220> FEATURE:
<223> OTHER INFORMATION: synthetic amino acid sequence

<400> SEQUENCE: 75

Ala Ala Leu Tyr Tyr Asp Tyr Asp Val Phe Gly Gly Gly Thr Tyr Lys
1               5                   10                  15

Gly Ser

<210> SEQ ID NO 76
<211> LENGTH: 18
<212> TYPE: PRT
<213> ORGANISM: Artificial
<220> FEATURE:
<223> OTHER INFORMATION: synthetic amino acid sequence

<400> SEQUENCE: 76

Ala Ala Thr Tyr Tyr Asp Tyr Asp Val Phe Gly Gly Gly Thr Asp Gly
1               5                   10                  15

Gly Ser

<210> SEQ ID NO 77
<211> LENGTH: 18

```
<212> TYPE: PRT
<213> ORGANISM: Artificial
<220> FEATURE:
<223> OTHER INFORMATION: synthetic amino acid sequence

<400> SEQUENCE: 77

Ala Ala Arg Tyr Trp Asp Tyr Asp Val Phe Gly Gly Gly Thr Pro Glu
1               5                   10                  15

Gly Val

<210> SEQ ID NO 78
<211> LENGTH: 18
<212> TYPE: PRT
<213> ORGANISM: Artificial
<220> FEATURE:
<223> OTHER INFORMATION: synthetic amino acid sequence

<400> SEQUENCE: 78

Ala Ala Arg Tyr Trp Asp Tyr Asp Val Phe Gly Gly Gly Thr Ala Gln
1               5                   10                  15

Gly Glu

<210> SEQ ID NO 79
<211> LENGTH: 18
<212> TYPE: PRT
<213> ORGANISM: Artificial
<220> FEATURE:
<223> OTHER INFORMATION: synthetic amino acid sequence

<400> SEQUENCE: 79

Ala Ala Arg Tyr Trp Asp Tyr Asp Val Phe Gly Gly Gly Thr Pro Glu
1               5                   10                  15

Gly Val

<210> SEQ ID NO 80
<211> LENGTH: 18
<212> TYPE: PRT
<213> ORGANISM: Artificial
<220> FEATURE:
<223> OTHER INFORMATION: synthetic amino acid sequence

<400> SEQUENCE: 80

Ala Ala Arg Tyr Trp Asp Tyr Asp Val Phe Gly Gly Gly Thr Pro Glu
1               5                   10                  15

Gly Val

<210> SEQ ID NO 81
<211> LENGTH: 18
<212> TYPE: PRT
<213> ORGANISM: Artificial
<220> FEATURE:
<223> OTHER INFORMATION: synthetic amino acid sequence

<400> SEQUENCE: 81

Ala Ala Arg Tyr Trp Asp Tyr Asp Val Phe Gly Gly Gly Thr Pro Glu
1               5                   10                  15

Gly Val

<210> SEQ ID NO 82
<211> LENGTH: 18
<212> TYPE: PRT
<213> ORGANISM: Artificial
<220> FEATURE:
<223> OTHER INFORMATION: synthetic amino acid sequence
```

```
<400> SEQUENCE: 82

Ala Ala Arg Tyr Trp Asp Tyr Asp Val Phe Gly Gly Gly Thr Pro Glu
1               5                   10                  15

Gly Ile

<210> SEQ ID NO 83
<211> LENGTH: 18
<212> TYPE: PRT
<213> ORGANISM: Artificial
<220> FEATURE:
<223> OTHER INFORMATION: synthetic amino acid sequence

<400> SEQUENCE: 83

Ala Ala Arg Tyr Trp Asp Tyr Asp Val Phe Gly Gly Gly Thr Pro Glu
1               5                   10                  15

Gly Val

<210> SEQ ID NO 84
<211> LENGTH: 18
<212> TYPE: PRT
<213> ORGANISM: Artificial
<220> FEATURE:
<223> OTHER INFORMATION: synthetic amino acid sequence

<400> SEQUENCE: 84

Ala Ala Arg Tyr Trp Asp Tyr Asp Val Phe Gly Gly Gly Thr Pro Glu
1               5                   10                  15

Gly Val

<210> SEQ ID NO 85
<211> LENGTH: 18
<212> TYPE: PRT
<213> ORGANISM: Artificial
<220> FEATURE:
<223> OTHER INFORMATION: synthetic amino acid sequence

<400> SEQUENCE: 85

Ala Gly Arg Tyr Trp Asp Tyr Asp Val Phe Gly Gly Gly Thr Ala Gln
1               5                   10                  15

Gly Ala

<210> SEQ ID NO 86
<211> LENGTH: 18
<212> TYPE: PRT
<213> ORGANISM: Artificial
<220> FEATURE:
<223> OTHER INFORMATION: synthetic amino acid sequence

<400> SEQUENCE: 86

Ala Gly Arg Tyr Trp Asp Tyr Asp Val Phe Gly Gly Gly Thr Ala Gln
1               5                   10                  15

Gly Ala

<210> SEQ ID NO 87
<211> LENGTH: 18
<212> TYPE: PRT
<213> ORGANISM: Artificial
<220> FEATURE:
<223> OTHER INFORMATION: synthetic amino acid sequence

<400> SEQUENCE: 87

Val Ala Lys Tyr Trp Asp Tyr Asp Val Phe Gly Gly Gly Thr Asp Ser
1               5                   10                  15
```

Gly Gly

<210> SEQ ID NO 88
<211> LENGTH: 18
<212> TYPE: PRT
<213> ORGANISM: Artificial
<220> FEATURE:
<223> OTHER INFORMATION: synthetic amino acid sequence

<400> SEQUENCE: 88

Ala Ala Ser Tyr Trp Asp Tyr Asp Val Phe Gly Gly Gly Thr Pro Val
1               5                   10                  15

Gly Asp

<210> SEQ ID NO 89
<211> LENGTH: 18
<212> TYPE: PRT
<213> ORGANISM: Artificial
<220> FEATURE:
<223> OTHER INFORMATION: synthetic amino acid sequence

<400> SEQUENCE: 89

Ala Ala Gln Tyr Trp Asp Tyr Asp Val Phe Gly Gly Gly Thr Pro Lys
1               5                   10                  15

Gly Glu

<210> SEQ ID NO 90
<211> LENGTH: 18
<212> TYPE: PRT
<213> ORGANISM: Artificial
<220> FEATURE:
<223> OTHER INFORMATION: synthetic amino acid sequence

<400> SEQUENCE: 90

Ala Ala Leu Tyr Arg Asp Tyr Asp Val Phe Gly Gly Gly Thr Pro Val
1               5                   10                  15

Gly Gly

<210> SEQ ID NO 91
<211> LENGTH: 18
<212> TYPE: PRT
<213> ORGANISM: Artificial
<220> FEATURE:
<223> OTHER INFORMATION: synthetic amino acid sequence

<400> SEQUENCE: 91

Ala Ala Leu Tyr Arg Asp Tyr Asp Val Phe Gly Gly Gly Thr Ser Ala
1               5                   10                  15

Gly Val

<210> SEQ ID NO 92
<211> LENGTH: 18
<212> TYPE: PRT
<213> ORGANISM: Artificial
<220> FEATURE:
<223> OTHER INFORMATION: synthetic amino acid sequence

<400> SEQUENCE: 92

Ala Ala Leu Tyr Arg Asp Tyr Asp Val Phe Gly Gly Gly Thr Pro Ser
1               5                   10                  15

Gly Val

<210> SEQ ID NO 93
<211> LENGTH: 18

```
<212> TYPE: PRT
<213> ORGANISM: Artificial
<220> FEATURE:
<223> OTHER INFORMATION: synthetic amino acid sequence

<400> SEQUENCE: 93

Ala Ala Leu Tyr Arg Asp Tyr Asp Val Phe Gly Gly Gly Thr Pro Lys
1               5                   10                  15

Gly Glu

<210> SEQ ID NO 94
<211> LENGTH: 18
<212> TYPE: PRT
<213> ORGANISM: Artificial
<220> FEATURE:
<223> OTHER INFORMATION: synthetic amino acid sequence

<400> SEQUENCE: 94

Ala Ala Leu Tyr Arg Asp Tyr Asp Val Phe Gly Gly Gly Thr Pro Lys
1               5                   10                  15

Gly Glu

<210> SEQ ID NO 95
<211> LENGTH: 18
<212> TYPE: PRT
<213> ORGANISM: Artificial
<220> FEATURE:
<223> OTHER INFORMATION: synthetic amino acid sequence

<400> SEQUENCE: 95

Ala Ala Leu Tyr Arg Asp Tyr Asp Val Phe Gly Gly Gly Thr Pro Ser
1               5                   10                  15

Gly Val

<210> SEQ ID NO 96
<211> LENGTH: 18
<212> TYPE: PRT
<213> ORGANISM: Artificial
<220> FEATURE:
<223> OTHER INFORMATION: synthetic amino acid sequence

<400> SEQUENCE: 96

Ala Ala Leu Tyr Arg Asp Tyr Asp Val Phe Gly Gly Gly Thr Pro Ser
1               5                   10                  15

Gly Val

<210> SEQ ID NO 97
<211> LENGTH: 18
<212> TYPE: PRT
<213> ORGANISM: Artificial
<220> FEATURE:
<223> OTHER INFORMATION: synthetic amino acid sequence

<400> SEQUENCE: 97

Ala Ala Leu Tyr Arg Asp Tyr Asp Val Phe Gly Gly Gly Thr Pro Arg
1               5                   10                  15

Gly Gly

<210> SEQ ID NO 98
<211> LENGTH: 18
<212> TYPE: PRT
<213> ORGANISM: Artificial
<220> FEATURE:
<223> OTHER INFORMATION: synthetic amino acid sequence
```

-continued

```
<400> SEQUENCE: 98

Ala Ala Leu Tyr Arg Asp Tyr Asp Val Phe Gly Gly Gly Thr Pro Lys
1               5                   10                  15

Gly Glu

<210> SEQ ID NO 99
<211> LENGTH: 18
<212> TYPE: PRT
<213> ORGANISM: Artificial
<220> FEATURE:
<223> OTHER INFORMATION: synthetic amino acid sequence

<400> SEQUENCE: 99

Ala Ala Leu Tyr Arg Asp Tyr Asp Val Phe Gly Gly Gly Thr Pro Val
1               5                   10                  15

Gly Gly

<210> SEQ ID NO 100
<211> LENGTH: 18
<212> TYPE: PRT
<213> ORGANISM: Artificial
<220> FEATURE:
<223> OTHER INFORMATION: synthetic amino acid sequence

<400> SEQUENCE: 100

Ala Ala Leu Tyr Arg Asp Tyr Asp Val Phe Gly Gly Gly Thr Pro Arg
1               5                   10                  15

Gly Ser

<210> SEQ ID NO 101
<211> LENGTH: 18
<212> TYPE: PRT
<213> ORGANISM: Artificial
<220> FEATURE:
<223> OTHER INFORMATION: synthetic amino acid sequence

<400> SEQUENCE: 101

Ala Ala Phe Tyr Arg Asp Tyr Asp Val Phe Gly Gly Gly Thr Pro Lys
1               5                   10                  15

Gly Gly

<210> SEQ ID NO 102
<211> LENGTH: 18
<212> TYPE: PRT
<213> ORGANISM: Artificial
<220> FEATURE:
<223> OTHER INFORMATION: synthetic amino acid sequence

<400> SEQUENCE: 102

Ala Ala Phe Tyr Arg Asp Tyr Asp Val Phe Gly Gly Gly Thr Pro Lys
1               5                   10                  15

Gly Gly

<210> SEQ ID NO 103
<211> LENGTH: 18
<212> TYPE: PRT
<213> ORGANISM: Artificial
<220> FEATURE:
<223> OTHER INFORMATION: synthetic amino acid sequence

<400> SEQUENCE: 103

Ala Ala Phe Tyr Arg Asp Tyr Asp Val Phe Gly Gly Gly Thr Asp Met
1               5                   10                  15
```

Gly Asn

<210> SEQ ID NO 104
<211> LENGTH: 18
<212> TYPE: PRT
<213> ORGANISM: Artificial
<220> FEATURE:
<223> OTHER INFORMATION: synthetic amino acid sequence

<400> SEQUENCE: 104

Ala Ala Trp Tyr Arg Asp Tyr Asp Val Phe Gly Gly Gly Thr Pro Leu
1               5                   10                  15

Gly Ala

<210> SEQ ID NO 105
<211> LENGTH: 18
<212> TYPE: PRT
<213> ORGANISM: Artificial
<220> FEATURE:
<223> OTHER INFORMATION: synthetic amino acid sequence

<400> SEQUENCE: 105

Ala Ala Trp Tyr Arg Asp Tyr Asp Val Phe Gly Gly Gly Thr Pro Leu
1               5                   10                  15

Gly Ala

<210> SEQ ID NO 106
<211> LENGTH: 18
<212> TYPE: PRT
<213> ORGANISM: Artificial
<220> FEATURE:
<223> OTHER INFORMATION: synthetic amino acid sequence

<400> SEQUENCE: 106

Ala Ala Arg Tyr Pro Asp Tyr Asp Val Phe Gly Gly Gly Thr Ser Met
1               5                   10                  15

Gly Gln

<210> SEQ ID NO 107
<211> LENGTH: 18
<212> TYPE: PRT
<213> ORGANISM: Artificial
<220> FEATURE:
<223> OTHER INFORMATION: synthetic amino acid sequence

<400> SEQUENCE: 107

Ala Ala Met Tyr Asp Asp Tyr Asp Val Phe Gly Gly Gly Thr Pro Ser
1               5                   10                  15

Gly Ala

<210> SEQ ID NO 108
<211> LENGTH: 18
<212> TYPE: PRT
<213> ORGANISM: Artificial
<220> FEATURE:
<223> OTHER INFORMATION: synthetic amino acid sequence

<400> SEQUENCE: 108

Ala Ala Tyr Tyr Leu Asp Tyr Asp Val Phe Gly Gly Gly Thr Pro Gly
1               5                   10                  15

Gly Gly

<210> SEQ ID NO 109
<211> LENGTH: 18

```
<212> TYPE: PRT
<213> ORGANISM: Artificial
<220> FEATURE:
<223> OTHER INFORMATION: synthetic amino acid sequence

<400> SEQUENCE: 109

Ala Ala Phe Tyr Asp Asp Tyr Asp Val Phe Gly Gly Gly Thr Pro Ala
1               5                   10                  15

Gly Gly

<210> SEQ ID NO 110
<211> LENGTH: 18
<212> TYPE: PRT
<213> ORGANISM: Artificial
<220> FEATURE:
<223> OTHER INFORMATION: synthetic amino acid sequence

<400> SEQUENCE: 110

Ala Ala Ser Tyr Leu Asp Tyr Asp Val Phe Gly Gly Gly Thr Pro Gly
1               5                   10                  15

Gly Gly

<210> SEQ ID NO 111
<211> LENGTH: 18
<212> TYPE: PRT
<213> ORGANISM: Artificial
<220> FEATURE:
<223> OTHER INFORMATION: synthetic amino acid sequence

<400> SEQUENCE: 111

Ala Ala Pro Tyr Leu Asp Tyr Asp Val Phe Gly Gly Gly Thr Pro Glu
1               5                   10                  15

Gly Ser

<210> SEQ ID NO 112
<211> LENGTH: 18
<212> TYPE: PRT
<213> ORGANISM: Artificial
<220> FEATURE:
<223> OTHER INFORMATION: synthetic amino acid sequence

<400> SEQUENCE: 112

Ala Ala Leu Tyr Ser Asp Tyr Asp Val Phe Gly Gly Gly Thr Pro Pro
1               5                   10                  15

Gly Val

<210> SEQ ID NO 113
<211> LENGTH: 17
<212> TYPE: PRT
<213> ORGANISM: Artificial
<220> FEATURE:
<223> OTHER INFORMATION: synthetic amino acid sequence

<400> SEQUENCE: 113

Ala Ala Pro Tyr Pro Asp Tyr Asp Val Phe Gly Gly Gly Thr Pro Gly
1               5                   10                  15

Ser

<210> SEQ ID NO 114
<211> LENGTH: 18
<212> TYPE: PRT
<213> ORGANISM: Artificial
<220> FEATURE:
<223> OTHER INFORMATION: synthetic amino acid sequence
```

<400> SEQUENCE: 114

Ala Ala Met Tyr Asp Asp Tyr Asp Val Phe Gly Gly Gly Thr Pro Ser
1               5                   10                  15

Gly Ala

<210> SEQ ID NO 115
<211> LENGTH: 18
<212> TYPE: PRT
<213> ORGANISM: Artificial
<220> FEATURE:
<223> OTHER INFORMATION: synthetic amino acid sequence

<400> SEQUENCE: 115

Ala Ala Leu Tyr Asp Asp Tyr Asp Val Phe Gly Gly Gly Thr Pro Ala
1               5                   10                  15

Gly Gly

<210> SEQ ID NO 116
<211> LENGTH: 4
<212> TYPE: PRT
<213> ORGANISM: Artificial
<220> FEATURE:
<223> OTHER INFORMATION: sequence motif

<400> SEQUENCE: 116

Asp Tyr Asp Val
1

<210> SEQ ID NO 117
<211> LENGTH: 4
<212> TYPE: PRT
<213> ORGANISM: Artificial
<220> FEATURE:
<223> OTHER INFORMATION: sequence motif

<400> SEQUENCE: 117

Tyr Asp Val Phe
1

<210> SEQ ID NO 118
<211> LENGTH: 4
<212> TYPE: PRT
<213> ORGANISM: Artificial
<220> FEATURE:
<223> OTHER INFORMATION: sequence motif

<400> SEQUENCE: 118

Asp Val Phe Gly
1

<210> SEQ ID NO 119
<211> LENGTH: 4
<212> TYPE: PRT
<213> ORGANISM: Artificial
<220> FEATURE:
<223> OTHER INFORMATION: sequence motif

<400> SEQUENCE: 119

Val Phe Gly Gly
1

<210> SEQ ID NO 120
<211> LENGTH: 4
<212> TYPE: PRT
<213> ORGANISM: Artificial
<220> FEATURE:

<223> OTHER INFORMATION: sequence motif

<400> SEQUENCE: 120

Phe Gly Gly Gly
1

<210> SEQ ID NO 121
<211> LENGTH: 4
<212> TYPE: PRT
<213> ORGANISM: Artificial
<220> FEATURE:
<223> OTHER INFORMATION: sequence motif

<400> SEQUENCE: 121

Gly Gly Gly Thr
1

<210> SEQ ID NO 122
<211> LENGTH: 5
<212> TYPE: PRT
<213> ORGANISM: Artificial
<220> FEATURE:
<223> OTHER INFORMATION: sequence motif

<400> SEQUENCE: 122

Asp Tyr Asp Val Phe
1               5

<210> SEQ ID NO 123
<211> LENGTH: 5
<212> TYPE: PRT
<213> ORGANISM: Artificial
<220> FEATURE:
<223> OTHER INFORMATION: sequence motif

<400> SEQUENCE: 123

Tyr Asp Val Phe Gly
1               5

<210> SEQ ID NO 124
<211> LENGTH: 5
<212> TYPE: PRT
<213> ORGANISM: Artificial
<220> FEATURE:
<223> OTHER INFORMATION: sequence motif

<400> SEQUENCE: 124

Asp Val Phe Gly Gly
1               5

<210> SEQ ID NO 125
<211> LENGTH: 5
<212> TYPE: PRT
<213> ORGANISM: Artificial
<220> FEATURE:
<223> OTHER INFORMATION: sequence motif

<400> SEQUENCE: 125

Val Phe Gly Gly Gly
1               5

<210> SEQ ID NO 126
<211> LENGTH: 5
<212> TYPE: PRT
<213> ORGANISM: Artificial
<220> FEATURE:
<223> OTHER INFORMATION: sequence motif

```
<400> SEQUENCE: 126

Phe Gly Gly Gly Thr
1               5

<210> SEQ ID NO 127
<211> LENGTH: 6
<212> TYPE: PRT
<213> ORGANISM: Artificial
<220> FEATURE:
<223> OTHER INFORMATION: sequence motif

<400> SEQUENCE: 127

Asp Tyr Asp Val Phe Gly
1               5

<210> SEQ ID NO 128
<211> LENGTH: 6
<212> TYPE: PRT
<213> ORGANISM: Artificial
<220> FEATURE:
<223> OTHER INFORMATION: sequence motif

<400> SEQUENCE: 128

Tyr Asp Val Phe Gly Gly
1               5

<210> SEQ ID NO 129
<211> LENGTH: 6
<212> TYPE: PRT
<213> ORGANISM: Artificial
<220> FEATURE:
<223> OTHER INFORMATION: sequence motif

<400> SEQUENCE: 129

Asp Val Phe Gly Gly Gly
1               5

<210> SEQ ID NO 130
<211> LENGTH: 6
<212> TYPE: PRT
<213> ORGANISM: Artificial
<220> FEATURE:
<223> OTHER INFORMATION: sequence motif

<400> SEQUENCE: 130

Val Phe Gly Gly Gly Thr
1               5

<210> SEQ ID NO 131
<211> LENGTH: 7
<212> TYPE: PRT
<213> ORGANISM: Artificial
<220> FEATURE:
<223> OTHER INFORMATION: sequence motif

<400> SEQUENCE: 131

Asp Tyr Asp Val Phe Gly Gly
1               5

<210> SEQ ID NO 132
<211> LENGTH: 7
<212> TYPE: PRT
<213> ORGANISM: Artificial
<220> FEATURE:
<223> OTHER INFORMATION: sequence motif

<400> SEQUENCE: 132
```

Tyr Asp Val Phe Gly Gly Gly
1               5

<210> SEQ ID NO 133
<211> LENGTH: 7
<212> TYPE: PRT
<213> ORGANISM: Artificial
<220> FEATURE:
<223> OTHER INFORMATION: sequence motif

<400> SEQUENCE: 133

Asp Val Phe Gly Gly Gly Thr
1               5

<210> SEQ ID NO 134
<211> LENGTH: 8
<212> TYPE: PRT
<213> ORGANISM: Artificial
<220> FEATURE:
<223> OTHER INFORMATION: synthetic amino acid sequence

<400> SEQUENCE: 134

Asp Tyr Asp Val Phe Gly Gly Gly
1               5

<210> SEQ ID NO 135
<211> LENGTH: 8
<212> TYPE: PRT
<213> ORGANISM: Artificial
<220> FEATURE:
<223> OTHER INFORMATION: sequence motif

<400> SEQUENCE: 135

Tyr Asp Val Phe Gly Gly Gly Thr
1               5

<210> SEQ ID NO 136
<211> LENGTH: 9
<212> TYPE: PRT
<213> ORGANISM: Artificial
<220> FEATURE:
<223> OTHER INFORMATION: sequence motif

<400> SEQUENCE: 136

Asp Tyr Asp Val Phe Gly Gly Gly Thr
1               5

<210> SEQ ID NO 137
<211> LENGTH: 124
<212> TYPE: PRT
<213> ORGANISM: Lama glama

<400> SEQUENCE: 137

Glu Val Gln Leu Val Glu Ser Gly Gly Ser Leu Val Gln Pro Gly Gly
1               5                   10                  15

Ser Leu Arg Leu Ser Cys Ala Ala Ser Gly Phe Thr Phe Asp Asp Tyr
                20                  25                  30

Ala Met Ser Trp Val Arg Gln Val Pro Gly Lys Gly Leu Glu Trp Val
            35                  40                  45

Ser Ser Ile Asn Trp Ser Gly Thr His Thr Asp Tyr Ala Asp Ser Val
        50                  55                  60

Lys Gly Arg Phe Thr Ile Ser Arg Asn Asn Ala Asn Asn Thr Leu Tyr
65                  70                  75                  80

Leu Gln Met Asn Ser Leu Lys Ser Glu Asp Thr Ala Val Tyr Tyr Cys
                85                  90                  95

```
Ala Lys Asn Trp Arg Asp Ala Gly Thr Thr Trp Phe Glu Lys Ser Gly
                100                 105                 110

Ser Ala Gly Gln Gly Thr Gln Val Thr Val Ser Ser
            115                 120

<210> SEQ ID NO 138
<211> LENGTH: 175
<212> TYPE: PRT
<213> ORGANISM: Artificial
<220> FEATURE:
<223> OTHER INFORMATION: fusion protein

<400> SEQUENCE: 138

Glu Val Gln Leu Val Glu Ser Gly Gly Ser Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Val Pro Gly Lys Gly Leu Glu Trp Val
        35                  40                  45

Ser Ser Ile Asn Trp Ser Gly Thr His Thr Asp Tyr Ala Asp Ser Val
    50                  55                  60

Lys Gly Arg Phe Thr Ile Ser Arg Asn Asn Ala Asn Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asn Trp Arg Asp Ala Gly Thr Thr Trp Phe Glu Lys Ser Gly
                100                 105                 110

Ser Ala Gly Gln Gly Thr Gln Val Thr Val Ser Ser Gly Gly Gly Gly
            115                 120                 125

Ser Gly Gly Gly Ser Ala Ala Ala Ser Tyr Ser Asp Tyr Asp Val Phe
        130                 135                 140

Gly Gly Gly Thr Asp Phe Gly Pro Ala Ala Glu Gln Lys Leu Ile
145                 150                 155                 160

Ser Glu Glu Asp Leu Asn Gly Ala Ala His His His His His
                165                 170                 175

<210> SEQ ID NO 139
<211> LENGTH: 175
<212> TYPE: PRT
<213> ORGANISM: Artificial
<220> FEATURE:
<223> OTHER INFORMATION: fusion protein

<400> SEQUENCE: 139

Glu Val Gln Leu Val Glu Ser Gly Gly Ser Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Val Pro Gly Lys Gly Leu Glu Trp Val
        35                  40                  45

Ser Ser Ile Asn Trp Ser Gly Thr His Thr Asp Tyr Ala Asp Ser Val
    50                  55                  60

Lys Gly Arg Phe Thr Ile Ser Arg Asn Asn Ala Asn Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asn Trp Arg Asp Ala Gly Thr Thr Trp Phe Glu Lys Ser Gly
                100                 105                 110
```

Ser Ala Gly Gln Gly Thr Gln Val Thr Val Ser Ser Gly Gly Gly Gly
        115                 120                 125
Ser Gly Gly Gly Ser Ala Ala Ala Phe Tyr Asp Asp Tyr Asp Val Phe
        130                 135                 140
Gly Gly Gly Thr Pro Ala Gly Gly Ala Ala Glu Gln Lys Leu Ile
145                 150                 155                 160
Ser Glu Glu Asp Leu Asn Gly Ala Ala His His His His His His
                165                 170                 175

<210> SEQ ID NO 140
<211> LENGTH: 10
<212> TYPE: PRT
<213> ORGANISM: Artificial
<220> FEATURE:
<223> OTHER INFORMATION: synthetic amino acid sequence

<400> SEQUENCE: 140

Gly Gly Gly Gly Ser Gly Gly Gly Ser Ala
1               5                   10

<210> SEQ ID NO 141
<211> LENGTH: 23
<212> TYPE: PRT
<213> ORGANISM: Artificial
<220> FEATURE:
<223> OTHER INFORMATION: synthetic amino acid sequence

<400> SEQUENCE: 141

Ala Ala Ala Glu Gln Lys Leu Ile Ser Glu Glu Asp Leu Asn Gly Ala
1               5                   10                  15

Ala His His His His His His
                20

<210> SEQ ID NO 142
<211> LENGTH: 149
<212> TYPE: PRT
<213> ORGANISM: Artificial
<220> FEATURE:
<223> OTHER INFORMATION: synthetic amino acid sequence

<400> SEQUENCE: 142

Glu Val Gln Leu Val Glu Ser Gly Gly Ser Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Val Pro Gly Lys Gly Leu Glu Trp Val
        35                  40                  45

Ser Ser Ile Asn Trp Ser Gly Thr His Thr Asp Tyr Ala Asp Ser Val
    50                  55                  60

Lys Gly Arg Phe Thr Ile Ser Arg Asn Asn Ala Asn Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asn Trp Arg Asp Ala Gly Thr Thr Trp Phe Glu Lys Ser Gly
            100                 105                 110

Ser Ala Gly Gln Gly Thr Gln Val Thr Val Ser Ser Gly Gly Gly Gly
        115                 120                 125

Ser Gly Gly Gly Ser Arg Tyr Trp Asp Tyr Asp Val Phe Gly Gly Gly
        130                 135                 140

Thr Pro Val Gly Gly
145

<210> SEQ ID NO 143
<211> LENGTH: 22
<212> TYPE: PRT
<213> ORGANISM: Artificial
<220> FEATURE:
<223> OTHER INFORMATION: synthetic amino acid sequence

<400> SEQUENCE: 143

```
Ala Ala Ala Arg Tyr Trp Asp Tyr Asp Val Phe Gly Gly Gly Thr Pro
1               5                   10                  15

Val Gly Gly Ala Ala Ala
            20
```

<210> SEQ ID NO 144
<211> LENGTH: 609
<212> TYPE: PRT
<213> ORGANISM: Homo sapiens

<400> SEQUENCE: 144

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285
```

```
Cys Glu Asn Gln Asp Ser Ile Ser Ser Lys Leu Lys Glu Cys Cys Glu
    290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                325                 330                 335
Lys Asp Val Cys Lys Asn Tyr Ala Glu Ala Lys Asp Val Phe Leu Gly
                340                 345                 350
Met Phe Leu Tyr Glu Tyr Ala Arg Arg His Pro Asp Tyr Ser Val Val
                355                 360                 365
Leu Leu Leu Arg Leu Ala Lys Thr Tyr Glu Thr Thr Leu Glu Lys Cys
    370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Glu Gln Leu Gly Glu Tyr Lys Phe Gln Asn Ala Leu Leu
                420                 425                 430
Val Arg Tyr Thr Lys Lys Val Pro Gln Val Ser Thr Pro Thr Leu Val
                435                 440                 445
Glu Val Ser Arg Asn Leu Gly Lys Val Gly Ser Lys Cys Cys Lys His
    450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
                500                 505                 510
Ser Ala Leu Glu Val Asp Glu Thr Tyr Val Pro Lys Glu Phe Asn Ala
                515                 520                 525
Glu Thr Phe Thr Phe His Ala Asp Ile Cys Thr Leu Ser Glu Lys Glu
    530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                565                 570                 575
Ala Phe Val Glu Lys Cys Cys Lys Ala Asp Asp Lys Glu Thr Cys Phe
                580                 585                 590
Ala Glu Glu Gly Lys Lys Leu Val Ala Ala Ser Gln Ala Ala Leu Gly
    595                 600                 605
Leu

<210> SEQ ID NO 145
<211> LENGTH: 24
<212> TYPE: PRT
<213> ORGANISM: Homo sapiens

<400> SEQUENCE: 145

Met Lys Trp Val Thr Phe Ile Ser Leu Leu Phe Leu Phe Ser Ser Ala
1               5                   10                  15
Tyr Ser Arg Gly Val Phe Arg Arg
            20

<210> SEQ ID NO 146
<211> LENGTH: 585
<212> TYPE: PRT
```

<213> ORGANISM: Homo sapiens

<400> SEQUENCE: 146

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
```

```
                    405                 410                 415
Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
            580                 585

<210> SEQ ID NO 147
<211> LENGTH: 18
<212> TYPE: PRT
<213> ORGANISM: Artificial
<220> FEATURE:
<223> OTHER INFORMATION: synthetic amino acid sequence

<400> SEQUENCE: 147

Ala Ala Arg Trp Trp Asp Tyr Asp Val Phe Gly Gly Gly Thr Pro Val
1               5                   10                  15

Gly Gly

<210> SEQ ID NO 148
<211> LENGTH: 18
<212> TYPE: PRT
<213> ORGANISM: Artificial
<220> FEATURE:
<223> OTHER INFORMATION: synthetic amino acid sequence

<400> SEQUENCE: 148

Ala Ala Arg Tyr Trp Asp Trp Asp Val Phe Gly Gly Gly Thr Pro Val
1               5                   10                  15

Gly Gly

<210> SEQ ID NO 149
<211> LENGTH: 18
<212> TYPE: PRT
<213> ORGANISM: Artificial
<220> FEATURE:
<223> OTHER INFORMATION: synthetic amino acid sequence

<400> SEQUENCE: 149

Ala Ala Arg Tyr Trp Asp Phe Asp Val Phe Gly Gly Gly Thr Pro Val
1               5                   10                  15

Gly Gly
```

```
<210> SEQ ID NO 150
<211> LENGTH: 18
<212> TYPE: PRT
<213> ORGANISM: Artificial
<220> FEATURE:
<223> OTHER INFORMATION: synthetic amino acid sequence

<400> SEQUENCE: 150

Ala Ala Arg Tyr Trp Asp Phe Asp Ala Phe Gly Gly Gly Thr Pro Val
1               5                   10                  15

Gly Gly

<210> SEQ ID NO 151
<211> LENGTH: 18
<212> TYPE: PRT
<213> ORGANISM: Artificial
<220> FEATURE:
<223> OTHER INFORMATION: synthetic amino acid sequence

<400> SEQUENCE: 151

Ala Ala Arg Phe Trp Asp Tyr Asp Val Phe Gly Gly Gly Thr Pro Val
1               5                   10                  15

Gly Gly

<210> SEQ ID NO 152
<211> LENGTH: 18
<212> TYPE: PRT
<213> ORGANISM: Artificial
<220> FEATURE:
<223> OTHER INFORMATION: synthetic amino acid sequence

<400> SEQUENCE: 152

Ala Ala Arg Tyr Trp Asp Tyr Asp Val Phe Gly Gly Gly Thr Pro Val
1               5                   10                  15

Asp Gly

<210> SEQ ID NO 153
<211> LENGTH: 18
<212> TYPE: PRT
<213> ORGANISM: Artificial
<220> FEATURE:
<223> OTHER INFORMATION: synthetic amino acid sequence

<400> SEQUENCE: 153

Ala Ala Arg Tyr Trp Asp Tyr Asp Val Phe Gly Gly Gly Ser Gln Val
1               5                   10                  15

Gly Gly

<210> SEQ ID NO 154
<211> LENGTH: 18
<212> TYPE: PRT
<213> ORGANISM: Artificial
<220> FEATURE:
<223> OTHER INFORMATION: synthetic amino acid sequence

<400> SEQUENCE: 154

Ala Ala Arg Tyr Trp Asp Tyr Asp Val Phe Gly Gly Gly Ser Pro Val
1               5                   10                  15

Gly Gly

<210> SEQ ID NO 155
<211> LENGTH: 18
<212> TYPE: PRT
<213> ORGANISM: Artificial
```

<220> FEATURE:
<223> OTHER INFORMATION: synthetic amino acid sequence

<400> SEQUENCE: 155

Ala Ala Arg Ser Trp Asp Phe Asp Val Phe Gly Gly Gly Thr Pro Val
1               5                   10                  15

Gly Gly

<210> SEQ ID NO 156
<211> LENGTH: 18
<212> TYPE: PRT
<213> ORGANISM: Artificial
<220> FEATURE:
<223> OTHER INFORMATION: synthetic amino acid sequence

<400> SEQUENCE: 156

Ala Ala Arg Asp Trp Asp Phe Asp Val Phe Gly Gly Gly Thr Pro Val
1               5                   10                  15

Gly Gly

<210> SEQ ID NO 157
<211> LENGTH: 18
<212> TYPE: PRT
<213> ORGANISM: Artificial
<220> FEATURE:
<223> OTHER INFORMATION: synthetic amino acid sequence

<400> SEQUENCE: 157

Ala Ala Arg Tyr Trp Asp Phe Asp Val Phe Gly Gly Gly Ser Pro Val
1               5                   10                  15

Gly Gly

<210> SEQ ID NO 158
<211> LENGTH: 175
<212> TYPE: PRT
<213> ORGANISM: Artificial
<220> FEATURE:
<223> OTHER INFORMATION: synthetic amino acid sequence

<400> SEQUENCE: 158

Glu Val Gln Leu Val Glu Ser Gly Gly Ser Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Val Pro Gly Lys Gly Leu Glu Trp Val
        35                  40                  45

Ser Ser Ile Asn Trp Ser Gly Thr His Thr Asp Tyr Ala Asp Ser Val
    50                  55                  60

Lys Gly Arg Phe Thr Ile Ser Arg Asn Asn Ala Asn Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asn Trp Arg Asp Ala Gly Thr Thr Trp Phe Glu Lys Ser Gly
            100                 105                 110

Ser Ala Gly Gln Gly Thr Gln Val Thr Val Ser Ser Gly Gly Gly Gly
        115                 120                 125

Ser Gly Gly Gly Ser Ala Ala Arg Tyr Trp Asp Tyr Asp Val Phe
    130                 135                 140

Gly Gly Gly Thr Pro Val Gly Gly Ala Ala Glu Gln Lys Leu Ile
145                 150                 155                 160

```
Ser Glu Glu Asp Leu Asn Gly Ala Ala His His His His His
            165                 170                 175
```

<210> SEQ ID NO 159
<211> LENGTH: 175
<212> TYPE: PRT
<213> ORGANISM: Artificial
<220> FEATURE:
<223> OTHER INFORMATION: synthetic amino acid sequence

<400> SEQUENCE: 159

```
Glu Val Gln Leu Val Glu Ser Gly Gly Ser Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Val Pro Gly Lys Gly Leu Glu Trp Val
        35                  40                  45

Ser Ser Ile Asn Trp Ser Gly Thr His Thr Asp Tyr Ala Asp Ser Val
    50                  55                  60

Lys Gly Arg Phe Thr Ile Ser Arg Asn Asn Ala Asn Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asn Trp Arg Asp Ala Gly Thr Thr Trp Phe Glu Lys Ser Gly
            100                 105                 110

Ser Ala Gly Gln Gly Thr Gln Val Thr Val Ser Ser Gly Gly Gly Gly
        115                 120                 125

Ser Gly Gly Gly Ser Ala Ala Ala Arg Tyr Trp Asp Phe Asp Val Phe
    130                 135                 140

Gly Gly Gly Thr Pro Val Gly Ala Ala Ala Glu Gln Lys Leu Ile
145                 150                 155                 160

Ser Glu Glu Asp Leu Asn Gly Ala Ala His His His His His
            165                 170                 175
```

<210> SEQ ID NO 160
<211> LENGTH: 175
<212> TYPE: PRT
<213> ORGANISM: Artificial
<220> FEATURE:
<223> OTHER INFORMATION: synthetic amino acid sequence

<400> SEQUENCE: 160

```
Glu Val Gln Leu Val Glu Ser Gly Gly Ser Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Val Pro Gly Lys Gly Leu Glu Trp Val
        35                  40                  45

Ser Ser Ile Asn Trp Ser Gly Thr His Thr Asp Tyr Ala Asp Ser Val
    50                  55                  60

Lys Gly Arg Phe Thr Ile Ser Arg Asn Asn Ala Asn Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asn Trp Arg Asp Ala Gly Thr Thr Trp Phe Glu Lys Ser Gly
            100                 105                 110

Ser Ala Gly Gln Gly Thr Gln Val Thr Val Ser Ser Gly Gly Gly Gly
        115                 120                 125
```

```
Ser Gly Gly Gly Ser Ala Ala Ala Arg Asp Trp Asp Phe Asp Val Phe
        130                 135                 140
Gly Gly Gly Thr Pro Val Gly Ala Ala Ala Glu Gln Lys Leu Ile
145                 150                 155                 160
Ser Glu Glu Asp Leu Asn Gly Ala Ala His His His His His His
                165                 170                 175
```

<210> SEQ ID NO 161
<211> LENGTH: 175
<212> TYPE: PRT
<213> ORGANISM: Artificial
<220> FEATURE:
<223> OTHER INFORMATION: synthetic amino acid sequence

<400> SEQUENCE: 161

```
Glu Val Gln Leu Val Glu Ser Gly Gly Ser Leu Val Gln Pro Gly Gly
1               5                   10                  15
Ser Leu Arg Leu Ser Cys Ala Ala Ser Gly Phe Thr Phe Asp Asp Tyr
            20                  25                  30
Ala Met Ser Trp Val Arg Gln Val Pro Gly Lys Gly Leu Glu Trp Val
        35                  40                  45
Ser Ser Ile Asn Trp Ser Gly Thr His Thr Asp Tyr Ala Asp Ser Val
    50                  55                  60
Lys Gly Arg Phe Thr Ile Ser Arg Asn Asn Ala Asn Asn Thr Leu Tyr
65                  70                  75                  80
Leu Gln Met Asn Ser Leu Lys Ser Glu Asp Thr Ala Val Tyr Tyr Cys
                85                  90                  95
Ala Lys Asn Trp Arg Asp Ala Gly Thr Thr Trp Phe Glu Lys Ser Gly
            100                 105                 110
Ser Ala Gly Gln Gly Thr Gln Val Thr Val Ser Ser Gly Gly Gly Gly
        115                 120                 125
Ser Gly Gly Gly Ser Ala Ala Ala Arg Ser Trp Asp Phe Asp Val Phe
    130                 135                 140
Gly Gly Gly Thr Pro Val Gly Ala Ala Ala Glu Gln Lys Leu Ile
145                 150                 155                 160
Ser Glu Glu Asp Leu Asn Gly Ala Ala His His His His His His
                165                 170                 175
```

<210> SEQ ID NO 162
<211> LENGTH: 16
<212> TYPE: PRT
<213> ORGANISM: Artificial
<220> FEATURE:
<223> OTHER INFORMATION: synthetic amino acid sequence

<400> SEQUENCE: 162

```
Arg Asp Trp Asp Phe Asp Val Phe Gly Gly Gly Thr Pro Val Gly Gly
1               5                   10                  15
```

<210> SEQ ID NO 163
<211> LENGTH: 9
<212> TYPE: PRT
<213> ORGANISM: Artificial
<220> FEATURE:
<223> OTHER INFORMATION: synthetic amino acid sequence

<400> SEQUENCE: 163

```
Gly Gly Gly Gly Ser Gly Gly Gly Ser
1               5
```

<210> SEQ ID NO 164

```
<211> LENGTH: 149
<212> TYPE: PRT
<213> ORGANISM: Artificial
<220> FEATURE:
<223> OTHER INFORMATION: synthetic amino acid sequence

<400> SEQUENCE: 164

Glu Val Gln Leu Val Glu Ser Gly Gly Ser Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Val Pro Gly Lys Gly Leu Glu Trp Val
        35                  40                  45

Ser Ser Ile Asn Trp Ser Gly Thr His Thr Asp Tyr Ala Asp Ser Val
    50                  55                  60

Lys Gly Arg Phe Thr Ile Ser Arg Asn Asn Ala Asn Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asn Trp Arg Asp Ala Gly Thr Thr Trp Phe Glu Lys Ser Gly
            100                 105                 110

Ser Ala Gly Gln Gly Thr Gln Val Thr Val Ser Ser Gly Gly Gly Gly
        115                 120                 125

Ser Gly Gly Gly Ser Arg Asp Trp Asp Phe Asp Val Phe Gly Gly Gly
    130                 135                 140

Thr Pro Val Gly Gly
145

<210> SEQ ID NO 165
<211> LENGTH: 259
<212> TYPE: PRT
<213> ORGANISM: Artificial
<220> FEATURE:
<223> OTHER INFORMATION: synthetic amino acid sequence

<400> SEQUENCE: 165

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Glu Ser Val
    50                  55                  60

Glu Gly Arg Phe Thr Ile Ser Arg Asp Asn Ala Lys Arg Thr Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Gln Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175
```

```
Glu Leu Val Ala Ala Ile Ser Arg Thr Gly Gly Ser Thr Tyr Tyr Pro
            180                 185                 190

Glu Ser Val Glu Gly Arg Phe Thr Ile Ser Arg Asp Asn Ala Lys Arg
            195                 200                 205

Thr Val Tyr Leu Gln Met Asn Ser Leu Arg Ala Glu Asp Thr Ala Val
            210                 215                 220

Tyr Tyr Cys Ala Ala Gly Val Arg Ala Glu Gln Gly Arg Val Arg
225                 230                 235                 240

Thr Leu Pro Ser Glu Tyr Thr Phe Trp Gly Gln Gly Thr Gln Val Thr
            245                 250                 255

Val Ser Ser

<210> SEQ ID NO 166
<211> LENGTH: 41
<212> TYPE: PRT
<213> ORGANISM: Artificial
<220> FEATURE:
<223> OTHER INFORMATION: synthetic amino acid sequence

<400> SEQUENCE: 166

Arg Asp Trp Asp Phe Asp Val Phe Gly Gly Gly Thr Pro Val Gly Gly
1               5                   10                  15

Gly Gly Gly Gly Ser Gly Gly Gly Ser Arg Asp Trp Asp Phe Asp Val
            20                  25                  30

Phe Gly Gly Gly Thr Pro Val Gly Gly
            35                  40

<210> SEQ ID NO 167
<211> LENGTH: 290
<212> TYPE: PRT
<213> ORGANISM: Artificial
<220> FEATURE:
<223> OTHER INFORMATION: synthetic amino acid sequence

<400> SEQUENCE: 167

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
            35                  40                  45

Ala Ala Ile Ser Arg Thr Gly Gly Ser Thr Tyr Tyr Pro Glu Ser Val
50                  55                  60

Glu Gly Arg Phe Thr Ile Ser Arg Asp Asn Ala Lys Arg Thr Val Tyr
65                  70                  75                  80

Leu Gln Met Asn Ser Leu Arg Ala Glu Asp Thr Ala Val Tyr Tyr Cys
            85                  90                  95

Ala Ala Ala Gly Val Arg Ala Glu Gln Gly Arg Val Arg Thr Leu Pro
            100                 105                 110

Ser Glu Tyr Thr Phe Trp Gly Gln Gly Thr Gln Val Thr Val Ser Ser
            115                 120                 125

Gly Gly Gly Gly Ser Gly Gly Gly Ser Arg Asp Trp Asp Phe Asp Val
            130                 135                 140

Phe Gly Gly Gly Thr Pro Val Gly Gly Gly Gly Ser Gly Gly
145                 150                 155                 160

Gly Ser Glu Val Gln Leu Val Glu Ser Gly Gly Leu Val Gln Pro
            165                 170                 175
```

```
Gly Gly Ser Leu Arg Leu Ser Cys Ala Ala Ser Gly Arg Thr Phe Ser
            180                 185                 190

Tyr Asn Pro Met Gly Trp Phe Arg Gln Ala Pro Gly Lys Gly Arg Glu
            195                 200                 205

Leu Val Ala Ala Ile Ser Arg Thr Gly Gly Ser Thr Tyr Tyr Pro Glu
            210                 215                 220

Ser Val Glu Gly Arg Phe Thr Ile Ser Arg Asp Asn Ala Lys Arg Thr
225                 230                 235                 240

Val Tyr Leu Gln Met Asn Ser Leu Arg Ala Glu Asp Thr Ala Val Tyr
                245                 250                 255

Tyr Cys Ala Ala Ala Gly Val Arg Ala Glu Gln Gly Arg Val Arg Thr
            260                 265                 270

Leu Pro Ser Glu Tyr Thr Phe Trp Gly Gln Gly Thr Gln Val Thr Val
            275                 280                 285

Ser Ser
    290

<210> SEQ ID NO 168
<211> LENGTH: 315
<212> TYPE: PRT
<213> ORGANISM: Artificial
<220> FEATURE:
<223> OTHER INFORMATION: synthetic amino acid sequence

<400> SEQUENCE: 168

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
            35                  40                  45

Ala Ala Ile Ser Arg Thr Gly Gly Ser Thr Tyr Tyr Pro Glu Ser Val
        50                  55                  60

Glu Gly Arg Phe Thr Ile Ser Arg Asp Asn Ala Lys Arg Thr Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Gln Gly Arg Val Arg Thr Leu Pro
            100                 105                 110

Ser Glu Tyr Thr Phe Trp Gly Gln Gly Thr Gln Val Thr Val Ser Ser
            115                 120                 125

Gly Gly Gly Gly Ser Gly Gly Gly Ser Arg Asp Trp Asp Phe Asp Val
        130                 135                 140

Phe Gly Gly Gly Thr Pro Val Gly Gly Gly Gly Ser Gly Gly Gly Gly
145                 150                 155                 160

Gly Ser Arg Asp Trp Asp Phe Asp Val Phe Gly Gly Gly Thr Pro Val
                165                 170                 175

Gly Gly Gly Gly Gly Gly Ser Gly Gly Gly Ser Glu Val Gln Leu Val
            180                 185                 190

Glu Ser Gly Gly Gly Leu Val Gln Pro Gly Gly Ser Leu Arg Leu Ser
            195                 200                 205

Cys Ala Ala Ser Gly Arg Thr Phe Ser Tyr Asn Pro Met Gly Trp Phe
        210                 215                 220

Arg Gln Ala Pro Gly Lys Gly Arg Glu Leu Val Ala Ala Ile Ser Arg
225                 230                 235                 240

Thr Gly Gly Ser Thr Tyr Tyr Pro Glu Ser Val Glu Gly Arg Phe Thr
```

```
                    245                 250                 255
Ile Ser Arg Asp Asn Ala Lys Arg Thr Val Tyr Leu Gln Met Asn Ser
                260                 265                 270

Leu Arg Ala Glu Asp Thr Ala Val Tyr Tyr Cys Ala Ala Gly Val
            275                 280                 285

Arg Ala Glu Gln Gly Arg Val Arg Thr Leu Pro Ser Glu Tyr Thr Phe
        290                 295                 300

Trp Gly Gln Gly Thr Gln Val Thr Val Ser Ser
305                 310                 315

<210> SEQ ID NO 169
<211> LENGTH: 284
<212> TYPE: PRT
<213> ORGANISM: Artificial
<220> FEATURE:
<223> OTHER INFORMATION: synthetic amino acid sequence

<400> SEQUENCE: 169

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Glu Ser Val
    50                  55                  60

Glu Gly Arg Phe Thr Ile Ser Arg Asp Asn Ala Lys Thr Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Gln Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Glu Ser Val Glu Gly Arg Phe Thr Ile Ser Arg Asp Asn Ala Lys Arg
        195                 200                 205

Thr Val Tyr Leu Gln Met Asn Ser Leu Arg Ala Glu Asp Thr Ala Val
    210                 215                 220

Tyr Tyr Cys Ala Ala Ala Gly Val Arg Ala Glu Gln Gly Arg Val Arg
225                 230                 235                 240

Thr Leu Pro Ser Glu Tyr Thr Phe Trp Gly Gln Gly Thr Gln Val Thr
                245                 250                 255

Val Ser Ser Gly Gly Gly Gly Ser Gly Gly Ser Arg Asp Trp Asp
            260                 265                 270

Phe Asp Val Phe Gly Gly Gly Thr Pro Val Gly Gly
        275                 280

<210> SEQ ID NO 170
```

<211> LENGTH: 309
<212> TYPE: PRT
<213> ORGANISM: Artificial
<220> FEATURE:
<223> OTHER INFORMATION: synthetic amino acid sequence

<400> SEQUENCE: 170

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Tyr Asn
            20                  25                  30

Pro Met Gly Trp Phe Arg Gln Ala Pro Gly Lys Gly Arg Glu Leu Val
        35                  40                  45

Ala Ala Ile Ser Arg Thr Gly Gly Ser Thr Tyr Tyr Pro Glu Ser Val
    50                  55                  60

Glu Gly Arg Phe Thr Ile Ser Arg Asp Asn Ala Lys Arg Thr Val Tyr
65                  70                  75                  80

Leu Gln Met Asn Ser Leu Arg Ala Glu Asp Thr Ala Val Tyr Tyr Cys
                85                  90                  95

Ala Ala Ala Gly Val Arg Ala Glu Gln Gly Arg Val Arg Thr Leu Pro
            100                 105                 110

Ser Glu Tyr Thr Phe Trp Gly Gln Gly Thr Gln Val Thr Val Ser Ser
        115                 120                 125

Ala Ala Ala Glu Val Gln Leu Val Glu Ser Gly Gly Gly Leu Val Gln
    130                 135                 140

Pro Gly Gly Ser Leu Arg Leu Ser Cys Ala Ala Ser Gly Arg Thr Phe
145                 150                 155                 160

Ser Tyr Asn Pro Met Gly Trp Phe Arg Gln Ala Pro Gly Lys Gly Arg
                165                 170                 175

Glu Leu Val Ala Ala Ile Ser Arg Thr Gly Gly Ser Thr Tyr Tyr Pro
            180                 185                 190

Glu Ser Val Glu Gly Arg Phe Thr Ile Ser Arg Asp Asn Ala Lys Arg
        195                 200                 205

Thr Val Tyr Leu Gln Met Asn Ser Leu Arg Ala Glu Asp Thr Ala Val
    210                 215                 220

Tyr Tyr Cys Ala Ala Ala Gly Val Arg Ala Glu Gln Gly Arg Val Arg
225                 230                 235                 240

Thr Leu Pro Ser Glu Tyr Thr Phe Trp Gly Gln Gly Thr Gln Val Thr
                245                 250                 255

Val Ser Ser Gly Gly Gly Gly Ser Gly Gly Gly Ser Arg Asp Trp Asp
            260                 265                 270

Phe Asp Val Phe Gly Gly Gly Thr Pro Val Gly Gly Gly Gly Gly Gly
        275                 280                 285

Ser Gly Gly Gly Ser Arg Asp Trp Asp Phe Asp Val Phe Gly Gly Gly
    290                 295                 300

Thr Pro Val Gly Gly
305
```

<210> SEQ ID NO 171
<211> LENGTH: 11
<212> TYPE: PRT
<213> ORGANISM: Artificial
<220> FEATURE:
<223> OTHER INFORMATION: sequence motif
<220> FEATURE:
<221> NAME/KEY: misc_feature
<222> LOCATION: (2)..(2)
<223> OTHER INFORMATION: X = Y, F, W, S or D
<220> FEATURE:

```
<221> NAME/KEY: misc_feature
<222> LOCATION: (5)..(5)
<223> OTHER INFORMATION: X = Y, F or W; of which an F preferred

<400> SEQUENCE: 171

Arg Xaa Trp Asp Xaa Asp Val Phe Gly Gly Gly
1               5                   10

<210> SEQ ID NO 172
<211> LENGTH: 12
<212> TYPE: PRT
<213> ORGANISM: Artificial
<220> FEATURE:
<223> OTHER INFORMATION: sequence motif
<220> FEATURE:
<221> NAME/KEY: misc_feature
<222> LOCATION: (2)..(2)
<223> OTHER INFORMATION: X = Y, F, W, S or D
<220> FEATURE:
<221> NAME/KEY: misc_feature
<222> LOCATION: (5)..(5)
<223> OTHER INFORMATION: X = Y, F or W; of which an F preferred

<400> SEQUENCE: 172

Arg Xaa Trp Asp Xaa Asp Val Phe Gly Gly Gly Thr
1               5                   10

<210> SEQ ID NO 173
<211> LENGTH: 13
<212> TYPE: PRT
<213> ORGANISM: Artificial
<220> FEATURE:
<223> OTHER INFORMATION: sequence motif
<220> FEATURE:
<221> NAME/KEY: misc_feature
<222> LOCATION: (2)..(2)
<223> OTHER INFORMATION: X = Y, F, W, S or D
<220> FEATURE:
<221> NAME/KEY: misc_feature
<222> LOCATION: (5)..(5)
<223> OTHER INFORMATION: X = Y, F or W; of which an F preferred

<400> SEQUENCE: 173

Arg Xaa Trp Asp Xaa Asp Val Phe Gly Gly Gly Thr Pro
1               5                   10

<210> SEQ ID NO 174
<211> LENGTH: 14
<212> TYPE: PRT
<213> ORGANISM: Artificial
<220> FEATURE:
<223> OTHER INFORMATION: sequence motif
<220> FEATURE:
<221> NAME/KEY: misc_feature
<222> LOCATION: (2)..(2)
<223> OTHER INFORMATION: X = Y, F, W, S or D
<220> FEATURE:
<221> NAME/KEY: misc_feature
<222> LOCATION: (5)..(5)
<223> OTHER INFORMATION: X = Y, F or W; of which an F preferred

<400> SEQUENCE: 174

Arg Xaa Trp Asp Xaa Asp Val Phe Gly Gly Gly Thr Pro Gly
1               5                   10

<210> SEQ ID NO 175
<211> LENGTH: 15
<212> TYPE: PRT
<213> ORGANISM: Artificial
<220> FEATURE:
<223> OTHER INFORMATION: sequence motif
<220> FEATURE:
```

```
<221> NAME/KEY: misc_feature
<222> LOCATION: (2)..(2)
<223> OTHER INFORMATION: X = Y, F, W, S or D
<220> FEATURE:
<221> NAME/KEY: misc_feature
<222> LOCATION: (5)..(5)
<223> OTHER INFORMATION: X =  Y, F or W; of which an F preferred

<400> SEQUENCE: 175

Arg Xaa Trp Asp Xaa Asp Val Phe Gly Gly Gly Thr Pro Gly Gly
1               5                   10                  15

<210> SEQ ID NO 176
<211> LENGTH: 11
<212> TYPE: PRT
<213> ORGANISM: Artificial
<220> FEATURE:
<223> OTHER INFORMATION: sequence motif

<400> SEQUENCE: 176

Arg Tyr Trp Asp Tyr Asp Val Phe Gly Gly Gly
1               5                   10

<210> SEQ ID NO 177
<211> LENGTH: 11
<212> TYPE: PRT
<213> ORGANISM: Artificial
<220> FEATURE:
<223> OTHER INFORMATION: sequence motif

<400> SEQUENCE: 177

Arg Asp Trp Asp Phe Asp Val Phe Gly Gly Gly
1               5                   10

<210> SEQ ID NO 178
<211> LENGTH: 11
<212> TYPE: PRT
<213> ORGANISM: Artificial
<220> FEATURE:
<223> OTHER INFORMATION: sequence motif

<400> SEQUENCE: 178

Arg Ser Trp Asp Phe Asp Val Phe Gly Gly Gly
1               5                   10

<210> SEQ ID NO 179
<211> LENGTH: 11
<212> TYPE: PRT
<213> ORGANISM: Artificial
<220> FEATURE:
<223> OTHER INFORMATION: sequence motif

<400> SEQUENCE: 179

Arg Tyr Trp Asp Phe Asp Val Phe Gly Gly Gly
1               5                   10

<210> SEQ ID NO 180
<211> LENGTH: 12
<212> TYPE: PRT
<213> ORGANISM: Artificial
<220> FEATURE:
<223> OTHER INFORMATION: sequence motif

<400> SEQUENCE: 180

Arg Tyr Trp Asp Tyr Asp Val Phe Gly Gly Gly Thr
1               5                   10

<210> SEQ ID NO 181
```

```
<211> LENGTH: 12
<212> TYPE: PRT
<213> ORGANISM: Artificial
<220> FEATURE:
<223> OTHER INFORMATION: sequence motif

<400> SEQUENCE: 181

Arg Asp Trp Asp Phe Asp Val Phe Gly Gly Gly Thr
1               5                   10

<210> SEQ ID NO 182
<211> LENGTH: 12
<212> TYPE: PRT
<213> ORGANISM: Artificial
<220> FEATURE:
<223> OTHER INFORMATION: sequence motif

<400> SEQUENCE: 182

Arg Ser Trp Asp Phe Asp Val Phe Gly Gly Gly Thr
1               5                   10

<210> SEQ ID NO 183
<211> LENGTH: 12
<212> TYPE: PRT
<213> ORGANISM: Artificial
<220> FEATURE:
<223> OTHER INFORMATION: sequence motif

<400> SEQUENCE: 183

Arg Tyr Trp Asp Phe Asp Val Phe Gly Gly Gly Thr
1               5                   10

<210> SEQ ID NO 184
<211> LENGTH: 13
<212> TYPE: PRT
<213> ORGANISM: Artificial
<220> FEATURE:
<223> OTHER INFORMATION: sequence motif

<400> SEQUENCE: 184

Arg Tyr Trp Asp Tyr Asp Val Phe Gly Gly Gly Thr Pro
1               5                   10

<210> SEQ ID NO 185
<211> LENGTH: 13
<212> TYPE: PRT
<213> ORGANISM: Artificial
<220> FEATURE:
<223> OTHER INFORMATION: sequence motif

<400> SEQUENCE: 185

Arg Asp Trp Asp Phe Asp Val Phe Gly Gly Gly Thr Pro
1               5                   10

<210> SEQ ID NO 186
<211> LENGTH: 13
<212> TYPE: PRT
<213> ORGANISM: Artificial
<220> FEATURE:
<223> OTHER INFORMATION: sequence motif

<400> SEQUENCE: 186

Arg Ser Trp Asp Phe Asp Val Phe Gly Gly Gly Thr Pro
1               5                   10

<210> SEQ ID NO 187
<211> LENGTH: 13
<212> TYPE: PRT
```

<213> ORGANISM: Artificial
<220> FEATURE:
<223> OTHER INFORMATION: sequence motif

<400> SEQUENCE: 187

Arg Tyr Trp Asp Phe Asp Val Phe Gly Gly Gly Thr Pro
1               5                   10

<210> SEQ ID NO 188
<211> LENGTH: 14
<212> TYPE: PRT
<213> ORGANISM: Artificial
<220> FEATURE:
<223> OTHER INFORMATION: sequence motif

<400> SEQUENCE: 188

Arg Tyr Trp Asp Tyr Asp Val Phe Gly Gly Gly Thr Pro Val
1               5                   10

<210> SEQ ID NO 189
<211> LENGTH: 14
<212> TYPE: PRT
<213> ORGANISM: Artificial
<220> FEATURE:
<223> OTHER INFORMATION: sequence motif

<400> SEQUENCE: 189

Arg Asp Trp Asp Phe Asp Val Phe Gly Gly Gly Thr Pro Val
1               5                   10

<210> SEQ ID NO 190
<211> LENGTH: 14
<212> TYPE: PRT
<213> ORGANISM: Artificial
<220> FEATURE:
<223> OTHER INFORMATION: sequence motif

<400> SEQUENCE: 190

Arg Ser Trp Asp Phe Asp Val Phe Gly Gly Gly Thr Pro Val
1               5                   10

<210> SEQ ID NO 191
<211> LENGTH: 14
<212> TYPE: PRT
<213> ORGANISM: Artificial
<220> FEATURE:
<223> OTHER INFORMATION: sequence motif

<400> SEQUENCE: 191

Arg Tyr Trp Asp Phe Asp Val Phe Gly Gly Gly Thr Pro Val
1               5                   10

<210> SEQ ID NO 192
<211> LENGTH: 6
<212> TYPE: PRT
<213> ORGANISM: Artificial
<220> FEATURE:
<223> OTHER INFORMATION: sequence motif

<400> SEQUENCE: 192

Asp Ala Phe Gly Gly Gly
1               5

<210> SEQ ID NO 193
<211> LENGTH: 7
<212> TYPE: PRT
<213> ORGANISM: Artificial
<220> FEATURE:

```
<223> OTHER INFORMATION: sequence motif

<400> SEQUENCE: 193

Asp Val Phe Gly Gly Gly Ser
1               5

<210> SEQ ID NO 194
<211> LENGTH: 7
<212> TYPE: PRT
<213> ORGANISM: Artificial
<220> FEATURE:
<223> OTHER INFORMATION: sequence motif

<400> SEQUENCE: 194

Asp Ala Phe Gly Gly Gly Thr
1               5
```

PEPTIDES CAPABLE OF BINDING TO SERUM PROTEINS AND COMPOUNDS, CONSTRUCTS AND POLYPEPTIDES COMPRISING THE SAME

RELATED APPLICATIONS

This application claims the benefit under 35 U.S.C. §119 (e) of U.S. provisional application Ser. No. 61/045,690 filed on Apr. 17, 2008; of U.S. provisional application Ser. No. 61/050,385 filed on May 5, 2008; and of U.S. provisional application Ser. No. 61/119,803 filed on Dec. 4, 2008, the entire disclosures of which are incorporated herein by reference.

FIELD OF THE INVENTION

The present invention relates to amino acid sequences that are capable of binding to serum proteins; to peptides that comprise or essentially consist of such amino acid sequences; to compounds and constructs (such as fusion proteins and polypeptides) that comprise such amino acid sequences; to nucleic acids that encode such amino acid sequences, peptides, fusion proteins or polypeptides; to compositions, and in particular pharmaceutical compositions, that comprise such amino acid sequences, peptides constructs, compounds, fusion proteins or polypeptides; and to uses of such amino acid sequences, peptides constructs, compounds, fusion proteins or polypeptides.

Other aspects, embodiments, advantages and applications of the invention will become clear from the further description herein.

BACKGROUND OF THE INVENTION

The non-prepublished International application PCT/EP2007/063348 entitled "Peptides capable of binding to serum proteins" describes methods for generating peptides that are capable of binding to serum proteins, which peptides can be linked or fused to a therapeutic moiety, compound, protein or other therapeutic entity in order to increase the half-life thereof.

PCT/EP2007/063348 also describes a number of specific amino acid sequences that are capable of binding to human serum albumin and that can be linked or fused to a therapeutic moiety, compound, protein or other therapeutic entity in order to increase the half-life thereof. These amino acid sequences include the amino acid sequence AASYSDYDVFGGGTD-FGP (SEQ ID NO:1), which is called "17D12" in PCT/EP2007/063348 and which is listed in PCT/EP2007/063348 as SEQ ID NO:3.

It is an object of the present invention to provide amino acid sequences with improved binding to serum albumin, compared to the amino acid sequence AASYSDYDVFGGGTD-FGP (SEQ ID NO:1). In particular, it is an object of the invention to provide amino acid sequences that:

bind better (as defined herein) to human serum albumin than the amino acid sequence

AASYSDYDVFGGGTDFGP,    (SEQ ID NO: 1)

and/or can specifically bind (as defined herein) to human serum albumin and that can also specifically bind serum albumin from at least one other species of mammal (such as serum albumin from a mouse, rat, rabbit, dog or a species of primate such as baboon or rhesus monkey), and in particular can specifically bind to human serum albumin and to serum albumin from cynomolgus monkey;

and/or can bind to (human) serum albumin and that have other improved properties for pharmaceutical use compared to the amino acid sequence AASYSDYDVFGGGTD-FGP (SEQ ID NO:1), such as improved stability, improved protease resistance, etc.;

and/or when linked or fused to a therapeutic moiety, compound, protein or other therapeutic entity provide a greater increase of the serum half-life or other pharmacologically relevant properties than the amino acid sequence of SEQ ID NO:1 (when linked or fused to the same therapeutic).

It is also an object of the invention to provide amino acid sequences that can be linked or fused to a therapeutic moiety, compound, protein or other therapeutic entity, such that the resulting compound or construct has an improved half-life compared to a corresponding compound or construct that contains the amino acid sequence AASYSDYDVFGGGTD-FGP (SEQ ID NO:1).

SUMMARY OF THE INVENTION

It is an object of the present invention to provide amino acid sequences that are an alternative, and in particular an improved alternative, to the serum protein-binding amino acid sequences described in PCT/EP2007/063348.

Generally, the invention achieves this objective by providing the amino acid sequences described herein. These amino acid sequences can bind to (and in particular, specifically bind to, as defined herein) serum albumin (and in particular to human serum albumin) and can be used as small peptides or as peptide moieties for linking or fusing to a therapeutic compound (such as a therapeutic protein or polypeptide) in order to increase the half-life thereof. These amino acid sequences (which are also referred to herein as "amino acid sequences of the invention") are as further defined herein.

Thus, according to a first aspect, the invention relates to an amino acid sequence that:

a) has at least 50%, preferably at least 65%, more preferably at least 70%, even more preferably at least 75%, such as at least 80%, such as at least 90%, but not 100%, sequence identity (as defined herein) with the amino acid sequence

AASYSDYDVFGGGTDFGP;    (SEQ ID NO: 1)

and that:

b) binds better to human serum albumin than the amino acid sequence

AASYSDYDVFGGGTDFGP.    (SEQ ID NO: 1)

Another aspect of the invention relates to an amino acid sequence that:

a) that has no more than 9, preferably no more than 8, in particular no more than 7, such as 6, 5, 4, 3, 2 or 1 amino acid difference(s) (as defined herein) with the amino acid sequence AASYSDYDVFGGGTDFGP (SEQ ID NO:1);

and that:
b) binds better to human serum albumin than the amino acid sequence

```
AASYSDYDVFGGGTDFGP.        (SEQ ID NO: 1)
```

In yet another aspect, the invention relates to an amino acid sequence that
a) contains one or more of the following sequence motifs: DYDV (SEQ ID NO:116), YDVF (SEQ ID NO:117), DVFG (SEQ ID NO:118), VFGG (SEQ ID NO:119), FGGG (SEQ ID NO:120) and/or GGGT (SEQ ID NO:121);
b) has a total length of between 5 and 50, preferably between 7 and 40, more preferably between 10 and 35, such as about 15, 20, 25 or 30 amino acid residues;
and that
c) binds better to human serum albumin than the amino acid sequence

```
AASYSDYDVFGGGTDFGP;        (SEQ ID NO: 1)
``` which amino acid sequence is not the sequence AASYSDY-DVFGGGTDFGP (SEQ ID NO:1).

In yet another aspect, the invention relates to an amino acid sequence that
a) contains one or more of the following sequence motifs: DYDVF (SEQ ID NO:122), YDVFG (SEQ ID NO:123), DVFGG (SEQ ID NO:124), VFGGG (SEQ ID NO:125) and/or FGGGT (SEQ ID NO:126);
b) has a total length of between 5 and 50, preferably between 7 and 40, more preferably between 10 and 35, such as about 15, 20, 25 or 30 amino acid residues;
and that
c) binds better to human serum albumin than the amino acid sequence

```
AASYSDYDVFGGGTDFGP;        (SEQ ID NO: 1)
``` which amino acid sequence is not the sequence AASYSDY-DVFGGGTDFGP (SEQ ID NO:1). Preferably, such an amino acid sequence is as further described herein.

In yet another aspect, the invention relates to an amino acid sequence that
a) contains one or more of the following sequence motifs: DYDVFG (SEQ ID NO:127), YDVFGG (SEQ ID NO:128), DVFGGG (SEQ ID NO:129) and/or VFGGGT (SEQ ID NO:130);
b) has a total length of between 6 and 50, preferably between 7 and 40, more preferably between 10 and 35, such as about 15, 20, 25 or 30 amino acid residues;
and that
c) binds better to human serum albumin than the amino acid sequence

```
AASYSDYDVFGGGTDFGP;        (SEQ ID NO: 1)
``` which amino acid sequence is not the sequence AASYSDY-DVFGGGTDFGP (SEQ ID NO:1). Preferably, such an amino acid sequence is as further described herein.

In yet another aspect, the invention relates to an amino acid sequence that
a) contains one or more of the following sequence motifs: DYDVFGG (SEQ ID NO:131), DVFGGGT (SEQ ID NO:133);

b) has a total length of between 7 and 50, preferably between 8 and 40, more preferably between 10 and 35, such as about 15, 20, 25 or 30 amino acid residues;
and that
c) binds better to human serum albumin than the amino acid sequence

```
AASYSDYDVFGGGTDFGP;        (SEQ ID NO: 1)
``` which amino acid sequence is not the sequence AASYSDY-DVFGGGTDFGP (SEQ ID NO:1). Preferably, such an amino acid sequence is as further described herein.

In yet another aspect, the invention relates to an amino acid sequence that
a) contains one or more of the following sequence motifs: DYDVFGGG (SEQ ID NO:134) and/or YDVFGGGT (SEQ ID NO:135);
b) has a total length of between 8 and 50, preferably between 9 and 40, more preferably between 10 and 35, such as about 15, 20, 25 or 30 amino acid residues;
and that
c) binds better to human serum albumin than the amino acid sequence

```
AASYSDYDVFGGGTDFGP;        (SEQ ID NO: 1)
``` which amino acid sequence is not the sequence AASYSDY-DVFGGGTDFGP (SEQ ID NO:1). Preferably, such an amino acid sequence is as further described herein.

In yet another aspect, the invention relates to an amino acid sequence that
a) contains the following sequence motif: DYDVFGGGT (SEQ ID NO:136);
b) has a total length of between 9 and 50, preferably between 9 and 40, more preferably between 10 and 35, such as about 15, 20, 25 or 30 amino acid residues;
and that
c) binds better to human serum albumin than the amino acid sequence

```
AASYSDYDVFGGGTDFGP;        (SEQ ID NO: 1)
``` which amino acid sequence is not the sequence AASYSDY-DVFGGGTDFGP (SEQ ID NO:1). Preferably, such an amino acid sequence is as further described herein.

The amino acid sequences of the invention (as further described herein) preferably (at least) contain:
(i) an Arg (R) residue, in particular an Arg (R) residue that is capable of forming a hydrogen bond with the amino acid residues Asn (N) 133 & Asn (N) 135 of human serum albumin and/or capable of forming electrostatic interactions with the main-chain oxygen atoms of the Pro (P) 134 and Leu (L) 136 residues of human serum albumin; and/or
(ii) a Trp (W) residue, in particular a Trp (W) residue that is capable of forming electrostatic interactions with the Arg (R) 138 residue of human serum albumin; and/or
(iii) the sequence motif GGG;
and preferably at least any two and more preferably all three of (i), (ii) and (iii).

The amino acid sequences of the invention (as further described herein) preferably (at least) contain:
(i) the sequence motif RXWD, in which X may be any amino acid sequence but is preferably W, Y, F, S or D; and/or (ii) the sequence motif GGG, preferably the sequence motif FGGG, more preferably the sequence motif DVFGGG (SEQ ID NO:129), and in particular the sequence motif

```
    DVFGGGT;           (SEQ ID NO: 133)
``` and most preferably both these sequence motifs (i) and (ii).

Instead of the sequence motif DVFGGG (SEQ ID NO:129), an preferred amino acid sequence of the invention may for example also contain the sequence motif DAFGGG (SEQ ID NO:192). Also, instead of the sequence motif DVFGGGT (SEQ ID NO:133), a preferred amino acid sequence of the invention may for example also contain the sequence motifs DVFGGGS (SEQ ID NO:193) or DAFGGGT (SEQ ID NO:194). Other similar sequence motifs that may be present in the amino acid sequences of the invention will be clear to the skilled person based on the disclosure herein (such as the sequences mentioned in Table II and in Table V).

Thus, in another aspect, the invention relates to an amino acid sequence that:
a) has at least 50%, preferably at least 65%, more preferably at least 70%, even more preferably at least 75%, such as at least 80%, such as at least 90%, but not 100%, sequence identity (as defined herein) with the amino acid sequence

```
    AASYSDYDVFGGGTDFGP;    (SEQ ID NO: 1)
``` and that:
b) binds better to human serum albumin than the amino acid sequence

```
    AASYSDYDVFGGGTDFGP;    (SEQ ID NO: 1)
``` and that:
c) comprises an Arg (R) residue, in particular an Arg (R) residue that is capable of forming a hydrogen bond with the amino acid residues Asn (N) 133 & Asn (N) 135 of human serum albumin and/or capable of forming electrostatic interactions with the main-chain oxygen atoms of the Pro (P) 134 and Leu (L) 136 residues of human serum albumin.

This amino acid sequence preferably also comprises (i) the sequence motif RXWD, in which X may be any amino acid sequence but is preferably W, Y, F, S or D; and/or (ii) the sequence motif GGG, preferably the sequence motif FGGG, more preferably the sequence motif DVFGGG (SEQ ID NO:129), and in particular the sequence motif DVFGGGT (SEQ ID NO:133); and most preferably both these sequence motifs.

The above amino acid sequence is also preferably as further described herein.

In another aspect, the invention relates to an amino acid sequence that:
a) has at least 50%, preferably at least 65%, more preferably at least 70%, even more preferably at least 75%, such as at least 80%, such as at least 90%, but not 100%, sequence identity (as defined herein) with the amino acid sequence

```
    AASYSDYDVFGGGTDFGP;    (SEQ ID NO: 1)
``` and that:
b) binds better to human serum albumin than the amino acid sequence

```
    AASYSDYDVFGGGTDFGP;    (SEQ ID NO: 1)
``` and that:
c) comprises a Trp (W) residue, in particular a Trp (W) residue that is capable of forming electrostatic interactions with the Arg (R) 138 residue of human serum albumin.

This amino acid sequence preferably also comprises (i) the sequence motif RXWD, in which X may be any amino acid sequence but is preferably W, Y, F, S or D; and/or (ii) the sequence motif GGG, preferably the sequence motif FGGG, more preferably the sequence motif DVFGGG (SEQ ID NO:129), and in particular the sequence motif DVFGGGT (SEQ ID NO:133); and most preferably both these sequence motifs.

The above amino acid sequence is also preferably as further described herein.

In another aspect, the invention relates to an amino acid sequence that:
a) has at least 50%, preferably at least 65%, more preferably at least 70%, even more preferably at least 75%, such as at least 80%, such as at least 90%, but not 100%, sequence identity (as defined herein) with the amino acid sequence

```
    AASYSDYDVFGGGTDFGP;    (SEQ ID NO: 1)
``` and that:
b) binds better to human serum albumin than the amino acid sequence

```
    AASYSDYDVFGGGTDFGP;    (SEQ ID NO: 1)
``` and that:
c) comprises an Arg (R) residue, in particular an Arg (R) residue that is capable of forming a hydrogen bond with the amino acid residues Asn (N) 133 & Asn (N) 135 of human serum albumin and/or capable of forming electrostatic interactions with the main-chain oxygen atoms of the Pro (P) 134 and Leu (L) 136 residues of human serum albumin;
and that
d) comprises a Trp (W) residue, in particular a Trp (W) residue that is capable of forming electrostatic interactions with the Arg (R) 138 residue of human serum albumin.

This amino acid sequence preferably also comprises (i) the sequence motif RXWD, in which X may be any amino acid sequence but is preferably W, Y, F, S or D; and/or (ii) the sequence motif GGG, preferably the sequence motif FGGG, more preferably the sequence motif DVFGGG (SEQ ID NO:129), and in particular the sequence motif DVFGGGT (SEQ ID NO:133); and most preferably both these sequence motifs.

The above amino acid sequences are also preferably as further described herein.

Some preferred, but non-limiting sequence motifs that may be present in the amino acid sequences of the invention are:
the amino acid sequence RXWDXDVFGGG (SEQ ID NO: 171), in which the first (from the N-terminal end) amino acid residue indicated by X is chosen from Y, S or D; and the second amino acid residue indicated by X is chosen from Y or F.

the amino acid sequence RXWDXDVFGGGT (SEQ ID NO: 172), in which the first (from the N-terminal end) amino acid residue indicated by X is chosen from Y, S or D; and the second amino acid residue indicated by X is chosen from Y or F.

the amino acid sequence RXWDXDVFGGGTP (SEQ ID NO: 173), in which the first (from the N-terminal end) amino acid residue indicated by X is chosen from Y, S or D; and the second amino acid residue indicated by X is chosen from Y or F.

the amino acid sequence RXWDXDVFGGGTPG (SEQ ID NO: 174), in which the first (from the N-terminal end) amino acid residue indicated by X is chosen from Y, S or D; and the second amino acid residue indicated by X is chosen from Y or F.

the amino acid sequence RXWDXDVFGGGTPGG (SEQ ID NO: 175), in which the first (from the N-terminal end) amino acid residue indicated by X is chosen from Y, S or D; and the second amino acid residue indicated by X is chosen from Y or F.

an amino acid sequence chosen from RYWDYDVFGGG (SEQ ID NO: 176); RDWDFDVFGGG (SEQ ID NO: 177); RSWDFDVFGGG (SEQ ID NO: 178) or RYWD-FDVFGGG (SEQ ID NO: 179); and in particular chosen from

```
RDWDFDVFGGG;        (SEQ ID NO: 177)
RSWDFDVFGGG         (SEQ ID NO: 178)
or
RYWDFDVFGGG.        (SEQ ID NO: 179)
``` an amino acid sequence chosen from RYWDYDVFGGGT (SEQ ID NO: 180); RDWDFDVFGGGT (SEQ ID NO: 181); RSWDFDVFGGGT (SEQ ID NO: 182) or RYWDFDVFGGGT (SEQ ID NO: 183); and in particular chosen from

```
RDWDFDVFGGGT;       (SEQ ID NO: 181)
RSWDFDVFGGGT        (SEQ ID NO: 182)
or
RYWDFDVFGGGT.       (SEQ ID NO: 183)
``` an amino acid sequence chosen from RYWDYD-VFGGGTP (SEQ ID NO: 184); RDWDFDVFGGGTP (SEQ ID NO: 185); RSWDFDVFGGGTP (SEQ ID NO: 186) or RYWDFDVFGGGTP (SEQ ID NO: 187); and in particular chosen from

```
RDWDFDVFGGGTP;      (SEQ ID NO: 185)
RSWDFDVFGGGTP       (SEQ ID NO: 186)
or
RYWDFDVFGGGTP       (SEQ ID NO: 187)
``` an amino acid sequence chosen from RYWDYD-VFGGGTPV (SEQ ID NO: 188); RDWDFD-VFGGGTPV (SEQ ID NO: 189); RSWDFD-VFGGGTPV (SEQ ID NO: 190) or RYWDFDVFGGGTPV (SEQ ID NO: 191); and in particular chosen from

```
RDWDFDVFGGGTPV;     (SEQ ID NO: 189)
RSWDFDVFGGGTPV      (SEQ ID NO: 190)
or
RYWDFDVFGGGTPV.     (SEQ ID NO: 191)
```

In the context of the present invention, an amino acid sequence of the invention is deemed to "bind better" to serum albumin (such as human serum albumin or serum albumin from another species of mammal, such as serum albumin of cynomolgus monkey) than the amino acid sequence of SEQ ID NO:1:

when it binds to said serum albumin with a higher specificity than the amino acid sequence of SEQ ID NO:1; and/or when it binds to said serum albumin with a higher affinity (as defined herein, and expressed as a $K_D$, $K_A$, $k_{on}$ or $k_{off}$ rate, and determined using one of the methods described herein) than the amino acid sequence of SEQ ID NO:1; and/or when it binds stronger to said serum albumin than the amino acid sequence of SEQ ID NO:1 in the phage-ELISA assay described in Example 2 below; and/or when it binds better to said serum albumin than the amino acid sequence of SEQ ID NO:1 in the solution binding competition ELISA described in Example 3 below;

when it binds better to said serum albumin than the amino acid sequence of SEQ ID NO:1 in the solution binding competition ELISA described in Example 5 below;

when it binds to said serum albumin with a higher avidity (i.e. when the amino acid sequence of the invention is used as a concatamer) than the amino acid sequence of SEQ ID NO:1 (i.e. when it is used in the form of a comparable concatamer); and/or when a compound of the invention (as defined herein) that comprises one or more of said amino acid sequences of the invention binds to said serum albumin with a higher specificity, affinity and/or avidity than a corresponding compound of the invention that comprises one or more amino acid sequences of SEQ ID NO:1 (for example as determined using the BIAcore™ measurement used in Example 6). For example, and without limitation, an amino acid sequence of the invention is said to bind better to serum albumin when a fusion protein in which the relevant amino acid sequence is fused (optionally via a suitable linker) to the Nanobody 2D3 (SEQ ID NO: 137) binds with a higher specificity, affinity and/or avidity to serum albumin than a corresponding fusion protein in which the Nanobody 2D3 is fused (optionally via the same suitable linker) to the amino acid sequence AASYSDYDVFGGGTDFGP (SEQ ID NO:1) (for example as determined using the BIAcore™ measurement used in Example 6). For the purposes of this comparison, the relevant amino acid sequence and amino acid sequence AASYSDYDVFGGGTDFGP (SEQ ID NO:1) may for example (but without limitation) be linked to the C-terminus of 2D3 (optionally via the same suitable linker). As a specific but non-limiting example thereof, the specificity, affinity and/or avidity for serum albumin of a fusion protein that corresponds to the 2D3-56H5 fusion protein given in SEQ ID NO: 139 (in which the amino acid sequence 56H5 has been replaced by the relevant amino acid sequence) may be compared to the specificity, affinity and/or avidity for serum albumin of the corresponding fusion protein 2D3-17D12 given in SEQ ID NO: 138 (for example as determined using the BIAcore™ measurement used in Example 6).

In particular, "binding" as described herein may be determined using the solution binding competition assay described in Example 3 or Example 9; or, when the amino acid sequences is expressed as a fusion with the Nanobody 2D3 as described in Example 7 or 10, in the Biacore assays described in these Examples.

Preferably, the amino acid sequences of the invention are such that they bind equally well or preferably better to human serum albumin than the amino acid sequence 56E4 of the invention (SEQ ID NO:14). For this purpose, such an amino acid sequence of the invention may for example be the amino acid sequence 56E4 of the invention (SEQ ID NO:14) or an variant of the amino acid sequence 56E4 that is such that it binds equally well or preferably better to human serum albumin than the amino acid sequence 56E4, such as an affinity matured version of the amino acid sequence 56E4. Some preferred, but non-limiting examples of such amino acid sequences of the invention are given in Example 9 and Table V, and comprise the amino acid sequences 59E4 (SEQ ID NO:14); 59A5 (SEQ ID NO: 147); 59C8 (SEQ ID NO: 148); 59F2 (SEQ ID NO: 149); 59B3 (SEQ ID NO: 150); 59B2 (SEQ ID NO: 151); 60E6 (SEQ ID NO: 152); 60F1 (SEQ ID NO: 153); 60G5 (SEQ ID NO: 154); 59H12 (SEQ ID NO: 155); 59C2 (SEQ ID NO: 156); and 59H10 (SEQ ID NO: 157); of which 59F2 (SEQ ID NO: 149); 59C2 (SEQ ID NO: 156) and 59H12 (SEQ ID NO: 155) are particularly preferred.

Thus, in another aspect, the invention relates to an amino acid sequence that
a) is the sequence AARYWDYDVFGGGTPVGG (56E4; SEQ ID NO:14); or
b) has at least 65%, more preferably at least 70%, even more preferably at least 75%, such as at least 80%, for example at least 85% or at least 90% with the amino acid sequence AARYWDYDVFGGGTPVGG (56E4; SEQ ID NO:14); and/or
c) that has no more than 6, preferably no more than 5, in particular no more than 4, such as 3, 2 or 1 amino acid difference(s) (as defined herein) with the amino acid sequence

```
AARYWDYDVFGGGTPVGG      (56E4; SEQ ID NO: 14)
``` and that preferably:
d) binds equally well and preferably better to human serum albumin than the amino acid sequence AARYWDYDVFGGGTPVGG (56E4; SEQ ID NO:14).

Again, such amino acid sequences are incorporated into the meaning of the term "amino acid sequences of the invention" as used in its broadest sense herein; and they are preferably as further described herein. Thus, for example, such amino acid sequences preferably comprise (i) an Arg (R) residue, in particular an Arg (R) residue that is capable of forming a hydrogen bond with the amino acid residues Asn (N) 133 & Asn (N) 135 of human serum albumin and/or capable of forming electrostatic interactions with the main-chain oxygen atoms of the Pro (P) 134 and Leu (L) 136 residues of human serum albumin; and/or (ii) a Trp (W) residue, in particular a Trp (W) residue that is capable of forming electrostatic interactions with the Arg (R) 138 residue of human serum albumin; and/or (iii) the sequence motif GGG; and preferably at least any two and more preferably all three of (i), (ii) and (iii). In particular, such amino acid sequences of the invention preferably (at least) contain (i) the sequence motif RXWD, in which X may be any amino acid sequence but is preferably W, Y, F, S or D; and/or (ii) the sequence motif GGG, preferably the sequence motif FGGG, more preferably the sequence motif DVFGGG (SEQ ID NO:129), and in particular the sequence motif DVFGGGT (SEQ ID NO:133); and most preferably both these sequence motifs (i) and (ii).

In another aspect, the invention relates to an amino acid sequence that
a) is one of the amino acid sequences 59A5 (SEQ ID NO: 147); 59C8 (SEQ ID NO: 148); 59F2 (SEQ ID NO: 149); 59B3 (SEQ ID NO: 150); 59B2 (SEQ ID NO: 151); 60E6 (SEQ ID NO: 152); 60F1 (SEQ ID NO: 153); 60G5 (SEQ ID NO: 154); 59H12 (SEQ ID NO: 155); 59C2 (SEQ ID NO: 156); or 59H10 (SEQ ID NO: 157); or
b) has at least 65%, more preferably at least 70%, even more preferably at least 75%, such as at least 80%, for example at least 85% or at least 90% with at least one of the amino acid sequences 59A5 (SEQ ID NO: 147); 59C8 (SEQ ID NO: 148); 59F2 (SEQ ID NO: 149); 59B3 (SEQ ID NO: 150); 59B2 (SEQ ID NO: 151); 60E6 (SEQ ID NO: 152); 60F1 (SEQ ID NO: 153); 60G5 (SEQ ID NO: 154); 59H12 (SEQ ID NO: 155); 59C2 (SEQ ID NO: 156); and/or 59H10 (SEQ ID NO: 157); and/or
c) that has no more than 6, preferably no more than 5, in particular no more than 4, such as 3, 2 or 1 amino acid difference(s) (as defined herein) with at least one of the amino acid sequences 59A5 (SEQ ID NO: 147); 59C8 (SEQ ID NO: 148); 59F2 (SEQ ID NO: 149); 59B3 (SEQ ID NO: 150); 59B2 (SEQ ID NO: 151); 60E6 (SEQ ID NO: 152); 60F1 (SEQ ID NO: 153); 60G5 (SEQ ID NO: 154); 59H12 (SEQ ID NO: 155); 59C2 (SEQ ID NO: 156); and/or 59H10 (SEQ ID NO: 157);
and that preferably:
d) binds equally well and preferably better to human serum albumin than the amino acid sequence AARYWDYDVFGGGTPVGG (56E4; SEQ ID NO:14).

Again, such amino acid sequences are incorporated into the meaning of the term "amino acid sequences of the invention" as used in its broadest sense herein; and they are preferably as further described herein.

In another aspect, the invention relates to an amino acid sequence that
a) is one of the amino acid sequences 59F2 (SEQ ID NO: 149); 59H12 (SEQ ID NO: 155); or 59C2 (SEQ ID NO: 156); or
b) has at least 65%, more preferably at least 70%, even more preferably at least 75%, such as at least 80%, for example at least 85% or at least 90% with at least one of the amino acid sequences 59F2 (SEQ ID NO: 149); 59H12 (SEQ ID NO: 155); and/or 59C2 (SEQ ID NO: 156); and/or
c) that has no more than 6, preferably no more than 5, in particular no more than 4, such as 3, 2 or 1 amino acid difference(s) (as defined herein) with at least one of the amino acid sequences 59F2 (SEQ ID NO: 149); 59H12 (SEQ ID NO: 155); and/or 59C2 (SEQ ID NO: 156);
and that preferably:
d) binds equally well and preferably better to human serum albumin than the amino acid sequence AARYWDYDVFGGGTPVGG (56E4; SEQ ID NO:14).

Again, such amino acid sequences are incorporated into the meaning of the term "amino acid sequences of the invention" as used in its broadest sense herein; and they are preferably as further described herein.

According to another aspect, the invention relates to an amino acid sequence that has at least 50%, preferably at least 65%, more preferably at least 70%, even more preferably at least 75%, such as at least 80%, such as at least 90%, but not 100%, sequence identity (as defined herein) with the amino acid sequence AASYSDYDVFGGGTDFGP (SEQ ID NO:1); wherein said amino acid sequence is such that, when it is linked or fused to a therapeutic moiety, compound, protein or other therapeutic entity, the compound of the invention (as defined herein) thus obtained has a longer half-life (as defined herein) than a corresponding compound or construct in which said therapeutic moiety, compound, protein or other therapeutic entity is linked or fused to the amino acid sequence of SEQ ID NO:1 (i.e. instead of the amino acid sequence of the invention).

According to yet another aspect, the invention relates to an amino acid sequence that has no more than 9, preferably no more than 8, in particular no more than 7, such as 6, 5, 4, 3, 2 or 1 amino acid difference(s) (as defined herein) with the amino acid sequence AASYSDYDVFGGGTDFGP (SEQ ID NO:1); wherein said amino acid sequence is such that, when it is linked or fused to a therapeutic moiety, compound, protein or other therapeutic entity, the compound of the invention (as defined herein) thus obtained has a longer half-life (as defined herein) than a corresponding compound or construct in which said therapeutic moiety, compound, protein or other therapeutic entity is linked or fused to the amino acid sequence SEQ ID NO:1 (i.e. instead of the amino acid sequence of the invention).

Other aspects, embodiments, uses and advantages of the present invention will become clear from the further description herein.

Some representative, but non-limiting examples of amino acid sequences of the invention are listed as SEQ ID NO's: 2 to 115 in Table II and in SEQ ID NO's: 147 to 157 in Table V below (with some preferred representative examples being marked in bold typeface and underlined).

Some particularly preferred representative examples of amino acid sequences of the invention are the amino acid sequences PMP56G11 (SEQ ID NO:68); PMP56E4 (SEQ ID NO: 14); PMP54H4 (SEQ ID NO: 106); PMP54H5 (SEQ ID NO: 33); PMP56H1 (SEQ ID NO: 31); PMP56E2 (SEQ ID NO:47); PMP56G3 (SEQ ID NO: 35); PMP54G1 (SEQ ID NO:38); PMP56F1 (SEQ ID NO: 30); PMP54H2 (SEQ ID NO: 40); PMP56H9 (SEQ ID NO: 100); PMP56F2 (SEQ ID NO: 51); PMP26A3 (SEQ ID NO:26) and 01B3 (SEQ ID NO:115); and in particular 59E4 (SEQ ID NO:14); 59A5 (SEQ ID NO: 147); 59C8 (SEQ ID NO: 148); 59F2 (SEQ ID NO: 149); 59B3 (SEQ ID NO: 150); 59B2 (SEQ ID NO: 151); 60E6 (SEQ ID NO: 152); 60F1 (SEQ ID NO: 153); 60G5 (SEQ ID NO: 154); 59H12 (SEQ ID NO: 155); 59C2 (SEQ ID NO: 156); and 59H10 (SEQ ID NO: 157); of which 59F2 (SEQ ID NO: 149); 59C2 (SEQ ID NO: 156) and 59H12 (SEQ ID NO: 155) are particularly preferred.

Generally, the amino acid sequences of the invention will contain (within the overall limitations set out herein) one or more "amino acid differences" (as defined herein) with the amino acid sequence AASYSDYDVFGGGTDFGP (SEQ ID NO:1), such that the resulting amino acid sequence of the invention binds better (as defined herein) to human serum albumin than the amino acid sequence AASYSDYDVFGGGTDFGP (SEQ ID NO:1).

Generally, and within the overall limitations set out herein, such an amino acid difference may comprise an insertion, deletion or substitution or one or more amino acid residues at one or more positions, compared to the sequence of SEQ ID NO:1. Usually, compared to the sequence of SEQ ID NO:1, an amino acid sequence of the invention contains at least one amino acid substitution (such as those mentioned herein); and optionally also one or more amino acid insertions and/or one or more amino acid deletions.

Suitable substitutions, insertions and/or deletions (and combinations thereof) will be clear to the skilled person based on the disclosure herein, and for example include one or more of the substitutions, insertions and/or deletions that are present in the amino acid sequences of SEQ ID NOs: 2 to 115 and in SEQ ID NO's: 147 to 157 (and in particular in the amino acid sequences that are preferred among the amino acid sequences of SEQ ID NOs: 2 to 115 and/or and in the amino acid sequences of SEQ ID NO's: 147 to 157), or any suitable combination of these substitutions, insertions and/or deletions. For this purpose, an alignment of the sequence of SEQ ID NO:1 and the sequences of SEQ ID NOs: 2 to 115 are given in FIG. 1) and in Table V, the sequences of SEQ ID NO's: 147 to 157 are compared to the sequence of SEQ ID NO: 14.

Some preferred, but non-limiting, examples of possible substitutions that can be present in an amino acid sequence of the invention (compared to the amino acid sequence of SEQ ID NO:1) are listed in Table I below (it being understood that an amino acid sequence of the invention can, within the limits set out herein, contain one or more further suitable amino acid substitutions, insertions or deletions).

It should be noted that in the most preferred amino acid sequences of the invention, position 3 is most preferably R, position 5 is W (preferably in combination with a D on position 6); position 7 is preferably F (but may also be Y or W); position 15 is P and position 16 is V.

By comparison, in the sequence of SEQ ID NO:1, position 3 is S; position 5 is S; position 7 is Y; position 15 is D, position 15 is D; and position 16 is F.

The most preferred amino acid sequences of the invention share the following residues with the sequence of SEQ ID NO:1: the Y at position 4 (although, in the sequences of the invention, this may also be F, W, S or D); the D at position 6; the DVFGGG motif at positions 8-13 (although this may also be DAFGGG in the preferred sequences of the invention), and the T at position 14; as well as the G at position 17.

TABLE I

Examples of possible substitutions that can be present in an amino acid sequence of the invention.

| Position | a.a. in SEQ ID NO: 1 | Examples of possible substitutions in an amino acid sequence of the invention | position in SEQ ID NO: 143 and Example 8 |
|---|---|---|---|
| 1 | A | A (preferred) or V | 2 |
| 2 | A | A (preferred), G or V | 3 |
| 3 | S | R (preferred), L, F, Y, W, P, T, S, M, A, D, I, K, Q or V; | 4 |
| 4 | Y | Y, F, W, S or D | 5 |
| 5 | S | Y, R, W, F, L, D, P, G, H, K, M, S, T; of which W is much preferred in combination with a D on position 6 | 6 |
| 7 | Y | Y, F or W; of which an F preferred | 8 |
| 11 | G | G (preferred) or A | 12 |
| 15 | D | P (preferred), A, D, S, V, E, G, Q, R, W or Y | 16 |
| 16 | F | V, L, E, G, S, R, K, A, P, Q, D, M, F, I, T | 17 |
| 18 | P | G, E, A, V, S, D, T, N, I, Q, R or W | 19 |

Optionally, based on the disclosure herein (such as Table II below), the skilled person will also be able to determine other (or additional) suitable substitutions, insertions and/or deletions (or combinations thereof) by means of limited trail-anderror, for example by testing a candidate amino acid sequence that comprises the intended substitutions, insertions and/or deletions for binding to human serum albumin, for example using the assay of Example 2 and/or Example 3 below (in which said candidate amino acid sequence may then optionally be compared to the amino acid sequence of SEQ ID NO:1 and/or to one or more of the amino acid sequences of SEQ ID NOs: 2 to 115 and/or SEQ ID NO's: 147 to 157).

Again, such amino acid sequences are preferably as further described herein. Thus, for example, such amino acid sequences preferably comprise (i) an Arg (R) residue, in particular an Arg (R) residue that is capable of forming a hydrogen bond with the amino acid residues Asn (N) 133 & Asn (N) 135 of human serum albumin and/or capable of forming electrostatic interactions with the main-chain oxygen atoms of the Pro (P) 134 and Leu (L) 136 residues of human serum albumin; and/or (ii) a Trp (W) residue, in particular a Trp (W) residue that is capable of forming electrostatic interactions with the Arg (R) 138 residue of human serum albumin; and/or (iii) the sequence motif GGG; and preferably at least any two and more preferably all three of (i), (ii) and (iii). In particular, such amino acid sequences of preferably (at least) contain (i) the sequence motif RXWD, in which X may be any amino acid sequence but is preferably W, Y, F, S or D; and/or (ii) the sequence motif GGG, preferably the sequence motif FGGG, more preferably the sequence motif DVFGGG (SEQ ID NO: 129), and in particular the sequence motif DVFGGGT (SEQ ID NO:133); and most preferably both these sequence motifs (i) and (ii).

Generally, when an amino acid sequence of the invention contains one or more amino acid substitutions compared to the amino acid sequence AASYSDYDVFGGGTDFGP (SEQ ID NO:1), these may be conservative amino acid substitutions (as defined herein) or non-conservative amino acid substitutions (it being understood by the skilled person that suitable non-conservative amino acid substitutions will generally be more likely to improve, or further improve, the binding to human serum albumin).

Other amino acid sequences of the invention may be provided by introducing suitable amino acid substitutions, insertions and/or deletions (or combinations thereof) in one of the amino acid sequences of SEQ ID NOs: 2 to 115 and/or SEQ ID NO's: 147 to 157, such that the resulting amino acid sequence of the invention binds better (as defined herein) to human serum albumin than the amino acid sequence AASYS-DYDVFGGGTDFGP (SEQ ID NO:1). Again, these may be conservative amino acid substitutions (as defined herein) or non-conservative amino acid substitutions (it being understood by the skilled person that suitable conservative amino acid substitutions will generally be more likely to ensure that the favourable binding to human serum albumin is retained, or even improved).

From the disclosure herein, it will be clear that the amino acid sequences of the invention preferably either contain, compared to the sequence of SEQ ID NO:1, no amino acid substitutions or deletions (and preferably also no insertions) at the positions 4, 6, 7, 8, 9, 10, 12, 13, 14 or 17; or only a limited number (i.e. 3, 2 or preferably only 1) amino acid substitutions or deletions compared to the sequence of SEQ ID NO:1 (which then preferably are conservative substitutions as defined herein). The reason for this is that, from the alanine scanning experiment described in Example 4, it has become clear that introducing amino acid substitutions or deletions, although not excluded from the scope of the invention, may carry an increased risk of reducing the binding to human serum albumin.

In another preferred, but non-limiting aspect, the amino acid sequences of the invention preferably contain a least one proline residue, such as 1, 2, 3 or 4 proline residues. In particular, the amino acid sequences of the invention may contain (a) proline residue(s) at one or more (such as any one, two, three or four) of the positions 1, 2, 3, 5, 11, 15, 16 or 18 (and in particular 3, 5, 15, 16 and/or 18). Proline residues may also be inserted next to or near these positions.

According to one preferred, but non-limiting aspect, an amino acid sequence of the invention may comprise one or more (such as any two, any three, any four or all five) of the following amino acid substitutions compared to the amino acid sequence of SEQ ID NO. 1:

the serine residue (S) at position 3 of SEQ ID NO: 1 is replaced by an amino acid residue chosen from arginine (R), proline (P), an aromatic amino acid residue (F, Y, W or H; in particular F, Y or W) or a hydrophobic amino acid residue (L, I, V or M);

and/or the serine residue (S) at position 5 of SEQ ID NO: 1 is replaced by an amino acid residue chosen from arginine (R), proline (P), or an aromatic amino acid residue (F, Y, W or H; in particular F, Y or W);

and/or the aspartate residue (D) at position 15 of SEQ ID NO:1 is replaced by an amino acid residue chosen from proline (P) or a small amino acid residue (A, G, S or T);

and/or the phenylalanine residue (F) at position 16 of SEQ ID NO:1 is replaced by proline (P), a hydrophobic amino acid residue (L, I, V or M), or a or a small amino acid residue (A, G, S or T);

and/or the proline residue (P) at position 18 of SEQ ID NO:1 is maintained or replaced by a (partially) negative amino acid residue (D, E, Q or N) or a small amino acid residue (A, G, S or T);

and optionally one or more further suitable amino acid insertions, deletions and/or substitutions (as further described herein).

In a particularly preferred subclass of amino acid sequences of the invention, the serine residue (S) at position 3 of SEQ ID NO:1 is replaced by arginine (R). These amino acid sequences may comprise one or more further amino acid insertions, deletions and/or substitutions as described herein.

In particular, in amino acid sequences of the invention with an R at position 3:

the serine residue (S) at position 5 of SEQ ID NO:1 is replaced by an amino acid residue chosen from proline (P) or an aromatic amino acid residue (F, Y, W or H; in particular F, Y or W);

and/or the aspartate residue (D) at position 15 of SEQ ID NO:1 is replaced by an amino acid residue chosen from proline (P) or a small amino acid residue (A, G, S or T);

and/or the phenylalanine residue (F) at position 16 of SEQ ID NO:1 is replaced by proline (P), a hydrophobic amino acid residue (L, I, V or M), or a or a small amino acid residue (A, G, S or T);

and/or the proline residue (P) at position 18 of SEQ ID NO:1 is maintained or replaced by a (partially) negative amino acid residue (D, E, Q or N) or a small amino acid residue (A, G, S or T);

and optionally one or more further suitable amino acid insertions, deletions and/or substitutions (as further described herein).

Some preferred amino acid sequences within the amino acid sequences of the invention are the amino acid sequences of SEQ ID NO: 2 to 115 and/or SEQ ID NO's: 147 to 157, or amino acid sequences that have not more than 3, such as 3, 2, or 1 amino acid differences with one of the amino acid sequences of SEQ ID NO: 2 to 115 and/or SEQ ID NO's: 147 to 157 (in which said amino acid differences are preferably as generally described herein for the amino acid sequences of the invention).

Some more preferred amino acid sequences within the amino acid sequences of the invention are the amino acid sequences of SEQ ID NOs: 5, 7, 9, 14, 25, 26, 30, 31, 33, 34, 35, 36, 38, 40, 42, 47, 51, 55, 66, 68, 86, 94, 97, 100, 103, 106, 111; 115 and in particular 147, 148, 149, 150, 151, 152, 153, 154, 155, 156 and/or 147; or amino acid sequences that have not more than 3, such as 3, 2, or 1 amino acid differences with one of these amino acid sequences (in which said amino acid differences are preferably as generally described herein for the amino acid sequences of the invention).

Some particularly preferred amino acid sequences within the amino acid sequences of the invention are the amino acid sequences PMP56G11 (SEQ ID NO:68); PMP56E4 (SEQ ID NO: 14); PMP54H4 (SEQ ID NO: 106); PMP54H5 (SEQ ID NO: 33); PMP56H1 (SEQ ID NO: 31); PMP56E2 (SEQ ID NO:47); PMP56G3 (SEQ ID NO: 35); PMP54G1 (SEQ ID NO:38); PMP56F1 (SEQ ID NO: 30); PMP54H2 (SEQ ID NO: 40); PMP56H9 (SEQ ID NO: 100); PMP56F2 (SEQ ID NO: 51); PMP26A3 (SEQ ID NO:26) or 01B3 (SEQ ID NO:115); and in particular 59E4 (SEQ ID NO:14); 59A5 (SEQ ID NO: 147); 59C8 (SEQ ID NO: 148); 59F2 (SEQ ID NO: 149); 59B3 (SEQ ID NO: 150); 59B2 (SEQ ID NO: 151); 60E6 (SEQ ID NO: 152); 60F1 (SEQ ID NO: 153); 60G5 (SEQ ID NO: 154); 59H12 (SEQ ID NO: 155); 59C2 (SEQ ID NO: 156); and 59H10 (SEQ ID NO: 157) (of which 59F2 (SEQ ID NO: 149); 59C2 (SEQ ID NO: 156) and 59H12 (SEQ ID NO: 155) are particularly preferred); or amino acid sequences that have not more than 3, such as 3, 2, or 1 amino acid differences with one of these amino acid sequences (in which said amino acid differences are preferably as generally described herein for the amino acid sequences of the invention).

Preferably, an amino acid sequence of the invention has a total size of between 9 and 27 amino acid residues, such as between 12 and 24 amino acid residues, for example between 15 and 21 amino acid residues, such as 16, 17, 18, 19 or 20 amino acid residues).

The amino acid sequences of the invention can also be provided and/or used in the form of a peptide in which the amino acid sequence is linked to a small flanking sequence (e.g. of no more than 10, preferably of no more than 5 amino acid residues) at the C-terminus, the N-terminus, or both. These may for example be present because the amino acid sequence of the invention (or a compound of the invention in which said amino acid sequence is present) has been obtained by expression of a corresponding nucleotide sequence, in which the nucleotide sequence that encodes the amino acid sequence of the invention is either preceded by (i.e. at the 5'-end) and/or followed by (i.e. at the 3'-end) by a small nucleotide sequence that encodes a restriction site or that forms part of a cloning site (and that leads to the presence of the flanking sequence(s) in the expressed peptide). Examples of such flanking sequences are the amino acid sequences GSA and AAA.

The amino acid sequences described herein can bind to serum albumin in a "non-constrained" format (i.e. not comprising any disulphide bridges), and can advantageously be used in such a non-constrained format. It is however included in the scope of the invention that the amino acid sequences described herein are provided in, and/or are used in, a "constrained" format, for example in the form of a peptide in which an amino acid sequence of the invention is flanked by two flanking sequences that can form a disulphide bridge between them (for a further description hereof, reference is made to PCT/EP2007/063348).

The amino acid sequence of the invention is preferably such that it binds to serum albumin (and in particular to human serum albumin) in such a way that the half-life of the serum albumin molecule is not (significantly) reduced.

Preferably, the amino acid sequence of the invention binds to serum albumin or at least one part, fragment, epitope or domain thereof; and in particular to human serum albumin or at least one part, fragment, epitope or domain thereof. When the amino acid sequence of the invention binds to (human) serum albumin, it preferably is capable of binding to amino acid residues on serum albumin that are not involved in binding of (human) serum albumin to FcRn; and/or of binding to amino acid residues on serum albumin that do not form part of domain III of (human) serum albumin. Reference is made to WO 06/0122787.

Generally, the amino acid sequences of the invention are such that they bind better to human serum albumin than the amino acid sequence of SEQ ID NO:1. Preferably, the amino acid sequences of the invention are such that they bind equally well or better to human serum albumin than the amino acid sequence of SEQ ID NO:14. As mentioned, "binding" as described herein may in particular be determined using the solution binding competition assay described in Example 3 or Example 9; or, when the amino acid sequences is expressed as a fusion with the Nanobody 2D3 as described in Example 7 or 10, in the Biacore assays described in these Examples.

Preferably, any amino acid sequence of the invention as described herein has a total length of between 5 and 50, preferably between 7 and 40, more preferably between 10 and 35, such as about 15, 20, 25 or 30 amino acid residues.

Also, preferably, amino acid sequences of the invention are such that, when they are linked or fused to a therapeutic moiety, compound, protein or other therapeutic entity, the compound of the invention (as defined herein) thus obtained has a longer half-life (as defined herein) than a corresponding compound or construct in which said therapeutic moiety, compound, protein or other therapeutic entity is linked or fused to the amino acid sequence of SEQ ID NO:1 (i.e. instead of the amino acid sequence of the invention). This may in particular be determined by fusing the amino acid sequence of the invention to the Nanobody 2D3 in the manner described in Example 6 or Example 10, and then by determining the pharmacokinetic profile as described in Example 7 or Example 13.

In particular, in a preferred aspect, the amino acid sequences of the invention are such that, when they are linked or fused to a therapeutic moiety, compound, protein or other therapeutic entity, the compound of the invention (as defined herein) thus obtained has a similar or longer half-life (as defined herein) than a corresponding compound or construct in which said therapeutic moiety, compound, protein or other therapeutic entity is linked or fused to the amino acid sequence of SEQ ID NO:14 (56E4).

The amino acid sequences of the invention are preferably also cross-reactive (as defined herein) with the serum albumin from at least one species of mammal other than man; an in particular cross-reactive with serum albumin from cynomolgus monkey.

Generally, the amino acid sequences of the invention are also preferably such that they compete with the peptide of SEQ ID NO:1 and/or with the peptide of SEQ ID NO:14 for binding to human serum albumin, and/or such that they cross-block (as defined herein) the binding of the peptide of SEQ ID NO:1 and/or the binding of the peptide of SEQ ID NO:14 to human serum albumin.

The amino acid sequences of the invention are preferably such that they can bind to one or more of the following amino acid residues of human serum albumin (numbering as indicated in Example 8): Asn (N) 133; Pro (P) 134; Asn (N) 135; Leu (L) 136; Leu (L) 139; Arg (R) 141; Tyr (Y) 162; Glu (E) 165; Ile (I) 166; His (H) 170; Phe (F) 173; Phe (F) 181; Gly (G) 213; Lys (K) 214; Ser (S) 217; Gln (Q) 483; and/or Lys (K) 543; and/or such that they can compete with the amino acid sequence of SEQ ID NO:1 and/or the amino acid sequence of SEQ ID NO:14 for binding to one or more of these amino acid residues; and/or such that they can cross-block the binding of the amino acid sequence of SEQ ID NO:1 and/or the binding of the amino acid sequence of SEQ ID NO:14 to one or more of these amino acid residues.

More in particular, the amino acid sequences of the invention are preferably such that they can bind to an epitope on human serum albumin that comprises either (i) the stretch of amino acid residues that comprises the residues Asn (N) 133; Pro (P) 134; Asn (N) 135; Leu (L) 136; Leu (L) 139 and Arg (R) 141; and/or (ii) the stretch of amino acid residues that comprises the residues Tyr (Y) 162; Glu (E) 165; Ile (I) 166; His (H) 170; Phe (F) 173; Phe (F) 181; and/or (iii) the stretch of amino acid residues that comprises the residues Gly (G) 213; Lys (K) 214 and Ser (S) 217; and/or such that they can compete with the amino acid sequence of SEQ ID NO:1 and/or the amino acid sequence of SEQ ID NO:14 for binding to one of these stretches of amino acid residues; and/or such that they can cross-block the binding of the amino acid sequence of SEQ ID NO:1 and/or the binding of the amino acid sequence of SEQ ID NO:14 to one or more of these stretches of amino acid residues.

Even more in particular; the amino acid sequences of the invention are preferably such that they can bind to a hydrophobic subpocket on human serum albumin that is comprises (amongst others) residues the residues Leu (L) 139, Glu (E) 165, Ile (I) 166, His (H) 170, Phe (F) 173, Phe (F) 181, Gly (G) 213, Lys (K) 214, Ser (S) 217 and Gln (Q) 483; and/or such that they can compete with the amino acid sequence of SEQ ID NO:1 and/or the amino acid sequence of SEQ ID NO:14 for binding to this subpocket; and/or such that they can cross-block the binding of the amino acid sequence of SEQ ID NO:1 and/or the binding of the amino acid sequence of SEQ ID NO:14 to this subpocket.

The above peptides may be as further described herein; and may for example be affinity matured variants of the peptide of SEQ ID NO:1, and may in particular be affinity matured variants of the peptide of SEQ ID NO:14.

In one specific aspect, the invention does not comprise the amino acid sequences that are mentioned in FIG. 4 or FIG. 8 of PCT/EP2007/063348.

The amino acid sequences of the invention (or a compound of the invention comprising at least one such amino acid sequence, as further described herein) are preferably such that they can bind to a serum albumin, and in particular to human serum albumin:

with a dissociation constant ($K_D$) in the range of $10^{-5}$ to $10^{-12}$ moles/liter or less, and preferably in the range of $10^{-7}$ to $10^{-12}$ moles/liter or less and more preferably in the range of $10^{-8}$ to $10^{-12}$ moles/liter (i.e. with an association constant ($K_A$) of in the range of $10^5$ to $10^{12}$ liter/moles or more, and preferably in the range of $10^7$ to $10^{12}$ liter/moles or more, and more preferably in the range of $10^8$ to $10^{12}$ liter/moles), such that said dissociation constant is better (i.e. smaller/lower) than the dissociation constant with which the amino acid sequence AASYSDYDVFGGGTDFGP (SEQ ID NO:1) binds to human serum albumin;

and/or with a $k_{on}$-rate in the range of between $10^2$ $M^{-1}s^{-1}$ to about $10^7$ $M^{-1}s^{-1}$, preferably in the range between $10^3$ $M^{-1}s^{-1}$ and $10^7$ $M^{-1}s^{-1}$, more preferably in the range between $10^4$ $M^{-1}s^{-1}$ and $10^7$ $M^{-1}s^{-1}$, such as between $10^5$ $M^{-1}s^{-1}$ and $10^7$ $M^{-1}s^{-1}$ such that said $k_{on}$-rate is better (i.e. higher) than the $k_{on}$-rate with which the amino acid sequence AASYSDYDVFGGGTDFGP (SEQ ID NO:1) binds to human serum albumin;

and/or with a $k_{off}$-rate in the range between 1 $s^{-1}$ ($t_{1/2}$=0.69 s) and $10^{-6}$ $s^{-1}$ (providing a near irreversible complex with a $t_{1/2}$ of multiple days), preferably in the range between $10^{-2}$ $s^{-1}$ and $10^{-6}$ $s^{-1}$, more preferably in the range between $10^{-3}$ $s^{-1}$ and $10^{-4}$ $s^{-1}$, such as in the range between $10^{-4}$ $s^{-1}$ and $10^{-6}$ $s^{-1}$, such that said $k_{off}$-rate is better (i.e. higher) than the $k_{off}$-rate with which the amino acid sequence AASYSDYDVFGGGTDFGP (SEQ ID NO:1) binds to human serum albumin.

Preferably, an amino acid sequence of the invention (or a compound of the invention comprising one such amino acid sequence, as further described herein) is such that it will bind to human serum albumin with an affinity less than 1000 nM, preferably less than 500 nM, preferably less than 200 nM, more preferably less than 10 nM, such as less than 500 pM; such that said affinity is better (i.e. smaller/lower) than the affinity with which the amino acid sequence AASYSDYDVFGGGTDFGP (SEQ ID NO:1) binds to human serum albumin.

The amino acid sequences of the invention (as well as compounds of the invention comprising the same, as defined herein) are preferably such that they bind to or otherwise associate with human serum albumin in such a way that, when the amino acid sequence (or compound) is bound to or otherwise associated with a human serum albumin in man, it exhibits a serum half-life of at least about 50% (such as about 50% to 70%), preferably at least 60% (such as about 60% to 80%), or preferably at least 70% (such as about 70% to 90%), more preferably at least 80% (such as about 80% to 90%), or preferably at least about 90% of the natural half-life of the human serum albumin in man.

The amino acid sequences of the invention may bind to serum albumin (such as human serum albumin) in a conditional manner (as described in the International application PCT/EP2007/060850 of Ablynx N.V.), i.e. such that:

a) they bind to human serum albumin molecule under a first biological condition with a dissociation constant ($K_D$) of $10^{-5}$ moles/liter or less; and b) they bind to human serum albumin under a second biological condition with a dissociation constant ($K_D$) that is at least 10 fold different from (and in particular more than) the dissociation constant with which said amino acid sequence binds to said desired molecule under said first biological condition.

in which the first and second biological conditions may be as described in the International application PCT/EP2007/060850 of Ablynx N.V. In particular, as described in the International application PCT/EP2007/060850, the first biological condition and the second biological condition may differ in respect of pH, in which said first biological condition may comprise a physiological pH of more than 7.0, for example a pH of more than 7.1 or a pH of more than 7.2, such as a pH in the range of 7.2 to 7.4; and the second biological condition may comprise a physiological pH of less than 7.0, for example a pH of less than 6.7 or a pH of less than 6.5, such as a pH in the range of 6.5 to 6.0 (or visa versa).

Preferably, however, amino acid sequences of the invention may bind to serum albumin (such as human serum albumin) in a manner that is "essentially independent of the pH" (as described in the International application PCT/EP2007/060849 of Ablynx N.V., and as further defined herein).

In one non-limiting aspect, the amino acid sequences of the invention are preferably cross-reactive (as defined herein) with serum albumin from at least one other species of mammal, for example from mouse, rabbit, rat, or a primate. In particular, the amino acid sequences of the invention may be cross-reactive with serum albumin from a primate chosen from the group consisting of monkeys from the genus *Macaca* (such as, and in particular, cynomolgus monkeys (*Macaca fascicularis*) and/or rhesus monkeys (*Macaca mulatta*) and baboon (*Papio ursinus*), and preferably at least with cyno serum albumin. Also, when an amino acid sequence of the invention is cross-reactive with serum albumin from such a species of primate, it is preferably such that, when it is bound to or associated with a serum albumin molecule in said primate, it exhibits a serum half-life of at least about 50% (such as about 50% to 70%), preferably at least about 60% (such as about 60% to 80%), or preferably at least about 70% (such as about 70% to 90%), more preferably at least about 80% (such as about 80% to 90%), or preferably at least about 90% of the natural half-life of said serum albumin in said primate.

The invention also relates to a compound or construct which comprises at least one amino acid sequence of the invention and at least one therapeutic moiety (also referred to herein as "compounds of the invention"). These compounds or constructs may be as further described herein, and may for example be polypeptide or protein constructs that comprise or essentially consist of at least one amino acid sequence of the invention that is linked to at least one therapeutic moiety, optionally via one or more suitable linkers or spacers. Such polypeptide or protein constructs may for example (without limitation) be a fusion protein, as further described herein.

Such compounds of the invention may contain one, two, three or more amino acid sequences of the invention, suitably linked to the at least one therapeutic moiety (and optionally to each other), optionally via one or more suitable linkers (as described herein). Also, when a compound of the invention comprises two, three or more amino acid sequences of the invention, these may be the same or different.

In one specific aspect, such compounds of the invention may comprise one amino acid sequence of the invention, suitably linked to the at least one therapeutic moiety, optionally via one or more suitable linkers (as described herein). For example, in such a case, when the therapeutic moiety is a protein or polypeptide (such that the resulting compound of the invention is a fusion protein), the amino acid sequence of the invention may either be linked to the C-terminus of the therapeutic moiety or to the N-terminus of the therapeutic moiety (again, optionally via a suitable linker).

In another specific aspect, such compounds of the invention may comprise two amino acid sequence of the invention, suitably linked to the at least one therapeutic moiety (and optionally to each other), optionally via one or more suitable linkers (as described herein).

More specifically, such compounds of the invention may comprise two amino acid sequence of the invention, that are each suitably linked to the at least one therapeutic moiety (i.e. on different attachment sites of the therapeutic moiety), again optionally via suitable linkers. For example, in such a case, when the therapeutic moiety is a protein or polypeptide (such that the resulting compound of the invention is a fusion protein), one amino acid sequence of the invention may for example be linked to the C-terminus of the therapeutic moiety (again, optionally via a suitable linker) and one amino acid sequence of the invention may for example be linked to the N-terminus of the therapeutic moiety (again, optionally via a suitable linker).

Alternatively, such compounds of the invention may comprise two (or more) amino acid sequences of the invention that are linked to each other (again, optionally via a suitable linker) so as to form a "tandem repeat", which tandem repeat may then be suitably linked to the at least one therapeutic moiety (again optionally via a suitable linker). For example, in such a case, when the therapeutic moiety is a protein or polypeptide (such that the resulting compound of the invention is a fusion protein), the tandem repeat of the two or more amino acid sequences of the invention may either be linked to the C-terminus of the therapeutic moiety or to the N-terminus of the therapeutic moiety (again, optionally via a suitable linker).

Other suitable combinations of two or more amino acid sequences of the invention and one or more therapeutic moieties (again, optionally linked via suitable linkers) will be clear to the skilled person based on the disclosure herein.

In another aspect, the compounds of the invention comprise two or more (such as two, three or four) therapeutic moieties (which may be the same or different), and one or more (such as two, three, four or more) amino acid sequences of the invention (which may also be the same or different), in which the two or more (such as two, three or four) therapeutic moieties and/or the one or more (such as two, three, four or more) amino acid sequences of the invention may be suitably linked to each other (again optionally via one or more suitable linkers) so as to form a compound of the invention. For example, in such compounds of the invention, the two or more therapeutic moieties may be suitably linked to each other (again optionally via one or more suitable linkers), and one or more of the amino acid sequences of the invention (and/or one or more tandem repeats of two or more amino acid sequences of the invention, as described herein) may be linked (again, optionally via one or more suitable linkers) to any (or all) of the therapeutic moieties.

Also, in a further aspect, one or more of the linker(s) used to link the two or more therapeutic moieties to each other may comprise one or more of the amino acid sequences of the invention, and such linkers comprising one or more amino acid sequences of the invention (optionally comprising one or more further linking amino acid sequences to link the acid sequences of the invention to each other and/or to one or more therapeutic moieties) form a further aspect of the invention.

For example, when a compound of the invention comprises two therapeutic moieties (which may be the same or different), some examples of possible but non-limiting configurations of the above compounds of the invention are:

[TM]-[L]-[AA]-[L]-[TM]
[AA]-[L]-[TM]-[L]-[TM]
[TM]-[L]-[TM]-[L]-[AA]
[TM]-[L]-[AA]-[L]-[AA]-[TM]

[AA]-[L]-[TM]-[L]-[TM]-[L]-[AA]
[AA]-[L]-[AA]-[TM]-[L]-[TM]
[TM]-[L]-[TM]-[L]-[AA]-[AA]
[AA]-[L]-[TM]-[L]-[AA]-[L]-[TM]-[L]-[AA]
[AA]-[L]-[TM]-[L]-[AA]-[L]-[AA]-[L]-[TM]-[L]-[AA]
in which "[TM]" refers to the therapeutic moiety, "[L]" refers to a linker (which in each case is optional), and "[AA]" refers to an amino acid sequence of the invention. Other suitable configuration will be clear to the skilled person based on the disclosure herein. Again, in these constructs, when there are two or more linkers and/or amino acid sequences of the invention present, these may be the same or different. Again, when the therapeutic moieties and the linkers are proteins or (polypeptides), the above constructs may be fusion proteins or fusion constructs (which may for example be suitably obtained by suitable expression of a corresponding nucleic acid or nucleotide sequence).

In another aspect, the invention relates to a polypeptide construct that comprises two or more (and in particular two or three, and preferably two) amino acid sequences of the invention, in which the two or more amino acid sequences of the invention present in said polypeptide may be the same or different; and in which the two or more amino acid sequences of the invention may be either linked directly to each other, or linked to each other via a suitable linker (as further described herein). Such a "tandem repeat" construct of the invention may again be linked to one or more therapeutic moieties, in the same way as a single amino acid sequence of the invention. In some cases, the use of a tandem repeat may provide for an (even further) improved affinity to human serum albumin (compared to the use of a single amino acid sequence of the invention) and/or for an (even further) improved half-life for the compounds of the invention that contain such a tandem repeat (compared to a compound of the invention that comprises a single amino acid sequence of the invention). A non-limiting example of the use of such a tandem repeat and of a compound of the invention that comprises such a tandem repeat is given in Example 14. Also, as described herein, such a tandem repeat construct may be used as a linker.

Such tandem repeats preferably contain two or more of the preferred amino acid sequences of the invention (which may be the same or different), and in particular the particularly preferred amino acid sequences of the invention, such as (for example) 56E4 and affinity matured variants of 56E4 such as 59H12, 59F2 and/or 59C2, all as described herein. The invention also relates to compounds and constructs that comprise such tandem repeats (which may again be fusion proteins); to nucleotide sequences or nucleic acids encoding such tandem repeats of such fusion proteins, and to uses of such tandem repeats (e.g. to extend half-life and/or as linkers).

Thus, in another aspect, the invention relates to a polypeptide construct that comprises two or more (and in particular two or three, and preferably two) amino acid sequences of the invention, in which the two or more amino acid sequences of the invention present in said polypeptide may be the same or different; and in which the two or more amino acid sequences of the invention may be either linked directly to each other, or linked to each other via a suitable linker (as further described herein); and in which each amino acid sequence present therein:
a) is one of the amino acid sequences 59A5 (SEQ ID NO: 147); 59C8 (SEQ ID NO: 148); 59F2 (SEQ ID NO: 149); 59B3 (SEQ ID NO: 150); 59B2 (SEQ ID NO: 151); 60E6 (SEQ ID NO: 152); 60F1 (SEQ ID NO: 153); 60G5 (SEQ ID NO: 154); 59H12 (SEQ ID NO: 155); 59C2 (SEQ ID NO: 156); or 59H10 (SEQ ID NO: 157); or
b) has at least 65%, more preferably at least 70%, even more preferably at least 75%, such as at least 80%, for example at least 85% or at least 90% with at least one of the amino acid sequences 59A5 (SEQ ID NO: 147); 59C8 (SEQ ID NO: 148); 59F2 (SEQ ID NO: 149); 59B3 (SEQ ID NO: 150); 59B2 (SEQ ID NO: 151); 60E6 (SEQ ID NO: 152); 60F1 (SEQ ID NO: 153); 60G5 (SEQ ID NO: 154); 59H12 (SEQ ID NO: 155); 59C2 (SEQ ID NO: 156); and/or 59H10 (SEQ ID NO: 157); and/or
c) has no more than 6, preferably no more than 5, in particular no more than 4, such as 3, 2 or 1 amino acid difference(s) (as defined herein) with at least one of the amino acid sequences 59A5 (SEQ ID NO: 147); 59C8 (SEQ ID NO: 148); 59F2 (SEQ ID NO: 149); 59B3 (SEQ ID NO: 150); 59B2 (SEQ ID NO: 151); 60E6 (SEQ ID NO: 152); 60F1 (SEQ ID NO: 153); 60G5 (SEQ ID NO: 154); 59H12 (SEQ ID NO: 155); 59C2 (SEQ ID NO: 156); and/or 59H10 (SEQ ID NO: 157);
and preferably:
d) binds equally well and preferably better to human serum albumin than the amino acid sequence AARYWDYD-VFGGGTPVGG (56E4; SEQ ID NO:14).

Again, the amino acid sequences present in such a tandem repeat may be as further described herein, and the tandem repeat may be linked to one or more therapeutic moieties, in the manner described herein.

Thus, in another aspect, the invention relates to a polypeptide construct that comprises two or more (and in particular two or three, and preferably two) amino acid sequences of the invention, in which the two or more amino acid sequences of the invention present in said polypeptide may be the same or different; and in which the two or more amino acid sequences of the invention may be either linked directly to each other, or linked to each other via a suitable linker (as further described herein); and in which each amino acid sequence present therein:
a) is one of the amino acid sequences 59F2 (SEQ ID NO: 149); 59H12 (SEQ ID NO: 155); or 59C2 (SEQ ID NO: 156); or
b) has at least 65%, more preferably at least 70%, even more preferably at least 75%, such as at least 80%, for example at least 85% or at least 90% with at least one of the amino acid sequences 59F2 (SEQ ID NO: 149); 59H12 (SEQ ID NO: 155); and/or 59C2 (SEQ ID NO: 156); and/or
c) has no more than 6, preferably no more than 5, in particular no more than 4, such as 3, 2 or 1 amino acid difference(s) (as defined herein) with at least one of the amino acid sequences 59F2 (SEQ ID NO: 149); 59H12 (SEQ ID NO: 155); and/or 59C2 (SEQ ID NO: 156);
and preferably:
d) binds equally well and preferably better to human serum albumin than the amino acid sequence AARYWDYD-VFGGGTPVGG (56E4; SEQ ID NO:14).

Again, the amino acid sequences present in such a tandem repeat may be as further described herein, and the tandem repeat may be linked to one or more therapeutic moieties, in the manner described herein.

The at least one therapeutic moiety present in the compounds of the invention preferably comprises or essentially consists of an amino acid sequence, and may in particular comprise or essentially consist of an immunoglobulin sequence or an antigen-binding fragment thereof (for example, an antibody or an antigen-binding fragment thereof), such as an immunoglobulin variable domain or an antigen-binding fragment thereof (for example, a $V_H$-domain, a $V_L$-domain, a $V_{HH}$-domain or an antigen-binding fragment thereof); or a protein or polypeptide comprising the same (for example, an scFv construct). For such constructs, reference is for example made to the review by Holliger and Hudson, Nat. Biotechnol. 2005 September; 23(9): 1126-36 and the further prior art cited therein.

According to one specific, but non-limiting aspect, the therapeutic moiety comprises or essentially consists of a (single) domain antibody, a "dAb", or a Nanobody®.

When the one or more therapeutic moieties are directed against one or more pharmaceutically relevant targets, they may be directed against any suitable target known per se. For example, when the therapeutic moiety comprises or essentially consists of a (single) domain antibody, a "dAb", or a Nanobody®, it may for example be a dAb or Nanobody, IGN-gamma (see for example WO 04/041863), IgE (see for example WO 04/041867), EGFR (see for example WO 05/044858; WO 07/066,106 or WO 07/080,392); vWF (see for example WO 04/062551 or WO 06/1222825); IGF-IR (see for example WO 07/042,289); IL-6 (see for example WO 07/110,219); IL-6R (see for example WO 08/020,079); GPCR's (see for example WO 08/074,839); chemokines (see for example WO 08/077,945); VEGF or its receptors (see for example WO 07/080,392; WO 08/101,985; WO 08/149,147; WO 08/149,146; or WO 08/149,150); RANK-L (see for example WO 08/142,164); IL-R1 (see for example WO 06/059108; WO 07/063,311; WO 07/063,308; or WO 08/149,149); TNF-R1 (see for example WO o6/038027; WO 07/049,017; WO 08/149,148 or WO 08/149,144); IL-4 or IL-13 (see for example WO 07/085,815); CD40L (see for example WO 06/030220).

The therapeutic moieties may also be other proteins or peptides with a known therapeutical and/or pharmacological actions, such as, for example and without limitation, GLP-1; insulin; EPO; somatropin; interferons, interleukins and (other) cytokines and/or protein drugs used in cancer therapy.

In a compound of the invention the one or more amino acid sequences of the invention may be either directly linked to the at least one therapeutic moiety or linked to the at least one therapeutic moiety via one or more suitable linkers or spacers. Suitable linkers will be clear to the skilled person, for example based on the further disclosure herein. Some preferred, but non-limiting linkers are those mentioned on pages 127 and 128 of the International application WO 08/020,079 of Ablynx N.V., and include the "gly-ser linkers" mentioned therein.

When the one or more therapeutic moieties are amino acid sequences, the linkers or spacers preferably comprise or essentially consist of amino acid sequences, so that the resulting compound or construct essentially consists of a (fusion) protein or (fusion) polypeptide (also referred to herein as a "polypeptide of the invention").

In a further aspect, the invention relates to a compound of the invention (as further defined herein) that comprises at least one amino acid sequence that has at least 50%, preferably at least 60%, more preferably at least 70%, even more preferably at least 75%, such as at least 80%, at least 85%, at least 90% or at least 95%, but not 100%, sequence identity (as defined herein) with the amino acid sequence AASYSDYDVFGGGTDFGP (SEQ ID NO:1), wherein said compound of the invention has a longer half-life (as defined herein) than a corresponding compound that, instead of said amino acid sequence(s), contains the amino acid sequence AASYSDYDVFGGGTDFGP (SEQ ID NO:1). Preferably, such a compound has a half-life that is essentially the same or longer than a corresponding compound that, instead of said amino acid sequence(s), contains the amino acid sequence 56E4 (SEQ ID NO:14). Again, the amino acid sequence(s) present in such a compound may be as further described herein; and are preferably amino acid sequences of the invention that are described herein as being preferred.

In a further aspect, the invention relates to a compound of the invention (as further defined herein) that comprises at least one amino acid sequence that that has no more than 10, preferably no more than 9, more preferably no more than 8, even more preferably no more than 7, such as 6, 5, 4, 3, 2 or 1 amino acid difference(s) (as defined herein) with the amino acid sequence AASYSDYDVFGGGTDFGP (SEQ ID NO:1), wherein said compound of the invention has a longer half-life (as defined herein) than a corresponding compound that, instead of said amino acid sequence(s), contains the amino acid sequence AASYSDYDVFGGGTDFGP (SEQ ID NO:1). Preferably, such a compound has a half-life that is essentially the same or longer than a corresponding compound that, instead of said amino acid sequence(s), contains the amino acid sequence 56E4 (SEQ ID NO: 14). Again, the amino acid sequence(s) present in such a compound may be as further described herein; and are preferably amino acid sequences of the invention that are described herein as being preferred.

In a further aspect, the invention relates to a compound of the invention that comprises at least two amino acid sequences of the invention. In another aspect, the invention relates to a compound of the invention that comprises at least one tandem repeat (as defined herein) of at least two amino acid sequences of the invention. Preferably, said compound of the invention has a longer half-life (as defined herein) than a corresponding compound that, instead of said amino acid sequences, contains the same number of copies of the amino acid sequence AASYSDYDVFGGGTDFGP (SEQ ID NO:1). More preferably, such a compound has a half-life that is essentially the same or longer than a corresponding compound that, instead of said amino acid sequence(s), contains the same number of copies of the amino acid sequence 56E4 (SEQ ID NO:14). Again, the amino acid sequence(s) present in such a compound may be as further described herein; and are preferably amino acid sequences of the invention that are described herein as being preferred.

Some other aspects of the invention relate to the following peptides. Again, such peptides are incorporated into the meaning of the term "amino acid sequences of the invention" as used in its broadest sense herein; and these peptides are preferably as further described herein for the amino acid sequences of the invention.

Thus, in another aspect, the invention relates to a peptide that is specific for (as defined herein) for human serum albumin and that binds better (as defined herein) to HSA than the amino acid sequence 56E4 (SEQ ID NO: 14).

In another aspect, the invention relates to a peptide that is specific for (as defined herein) for human serum albumin and that is an affinity matured variant of the amino acid sequence 56E4 (SEQ ID NO:14)

In another aspect, the invention relates to a peptide that is specific for (as defined herein) for human serum albumin and that comprises an Arg (R) residue; and the sequence motif DVFGGG (SEQ ID NO:129), in particular the sequence motif DVFGGGT (SEQ ID NO:133).

In another aspect, the invention relates to a peptide that is specific for (as defined herein) for human serum albumin and that comprises an Arg (R) residue that is capable of forming a hydrogen bond with the amino acid residues Asn (N) 133 & Asn (N) 135 of human serum albumin and/or capable of forming electrostatic interactions with the main-chain oxygen atoms of the Pro (P) 134 and Leu (L) 136 residues of human serum albumin; and the sequence motif DVFGGG (SEQ ID NO: 129), in particular the sequence motif DVFGGGT (SEQ ID NO:133).

In another aspect, the invention relates to a peptide that is specific for (as defined herein) for human serum albumin and that comprises a Trp (W) residue; and the sequence motif DVFGGG (SEQ ID NO:129), in particular the sequence motif DVFGGGT (SEQ ID NO:133).

In another aspect, the invention relates to a peptide that is specific for (as defined herein) for human serum albumin and that comprises a Trp (W) residue that is capable of forming electrostatic interactions with the Arg (R) 138 residue of human serum albumin; and the sequence motif DVFGGG (SEQ ID NO:129), in particular the sequence motif

```
DVFGGGT;          (SEQ ID NO: 133)
```

In another aspect, the invention relates to a peptide that is specific for (as defined herein) for human serum albumin and that comprises an Arg (R) residue; a Trp (W) residue; and the sequence motif DVFGGG (SEQ ID NO:129), in particular the sequence motif

```
DVFGGGT.          (SEQ ID NO: 133)
```

In another aspect, the invention relates to a peptide that is specific for (as defined herein) for human serum albumin and that comprises an Arg (R) residue; an aromatic amino acid residue that is capable of forming electrostatic interactions with the Arg (R) 138 residue of human serum albumin; and the sequence motif DVFGGG (SEQ ID NO:129), in particular the sequence motif DVFGGGT (SEQ ID NO:133).

In another aspect, the invention relates to a peptide that is specific for (as defined herein) for human serum albumin and that comprises an Arg (R) residue that is capable of forming a hydrogen bond with the amino acid residues Asn (N) 133 & Asn (N) 135 of human serum albumin and/or capable of forming electrostatic interactions with the main-chain oxygen atoms of the Pro (P) 134 and Leu (L) 136 residues of human serum albumin; a Trp (W) residue that is capable of forming electrostatic interactions with the Arg (R) 138 residue of human serum albumin; and the sequence motif DVFGGG (SEQ ID NO:129), in particular the sequence motif DVFGGGT (SEQ ID NO:133).

In another aspect, the invention relates to a peptide that is specific for (as defined herein) for human serum albumin and that comprises the amino acid sequence RXWDXDVFGGG (SEQ ID NO: 171), in which the first (from the N-terminal end) amino acid residue indicated by X is chosen from Y, S or D; and the second amino acid residue indicated by X is chosen from Y or F.

In another aspect, the invention relates to a peptide that is specific for (as defined herein) for human serum albumin and that comprises the amino acid sequence RXWDXDVFGGGT (SEQ ID NO: 172), in which the first (from the N-terminal end) amino acid residue indicated by X is chosen from Y, S or D; and the second amino acid residue indicated by X is chosen from Y or F.

In another aspect, the invention relates to a peptide that is specific for (as defined herein) for human serum albumin and that comprises the amino acid sequence RXWDXDVFGGGTP (SEQ ID NO: 173), in which the first (from the N-terminal end) amino acid residue indicated by X is chosen from Y, S or D; and the second amino acid residue indicated by X is chosen from Y or F.

In another aspect, the invention relates to a peptide that is specific for (as defined herein) for human serum albumin and that comprises the amino acid sequence RXWDXDVFGGGTPG (SEQ ID NO: 174), in which the first (from the N-terminal end) amino acid residue indicated by X is chosen from Y, S or D; and the second amino acid residue indicated by X is chosen from Y or F.

In another aspect, the invention relates to a peptide that is specific for (as defined herein) for human serum albumin and that comprises the amino acid sequence RXWDXDVFGGGTPGG (SEQ ID NO: 175), in which the first (from the N-terminal end) amino acid residue indicated by X is chosen from Y, S or D; and the second amino acid residue indicated by X is chosen from Y or F.

In another aspect, the invention relates to a peptide that is specific for (as defined herein) for human serum albumin and that comprises an amino acid sequence chosen from RYWDYDVFGGG (SEQ ID NO: 176); RDWDFDVFGGG (SEQ ID NO: 177); RSWDFDVFGGG (SEQ ID NO: 178) or RYWDFDVFGGG (SEQ ID NO: 179); and in particular chosen from RDWDFDVFGGG (SEQ ID NO: 177); RSWDFDVFGGG (SEQ ID NO: 178) or RYWDFDVFGGG (SEQ ID NO: 179).

In another aspect, the invention relates to a peptide that is specific for (as defined herein) for human serum albumin and that comprises an amino acid sequence chosen from RYWDYDVFGGGT (SEQ ID NO: 180); RDWDFDVFGGGT (SEQ ID NO: 181); RSWDFDVFGGGT (SEQ ID NO: 182) or RYWDFDVFGGGT (SEQ ID NO: 183); and in particular chosen from RDWDFDVFGGGT (SEQ ID NO: 181); RSWDFDVFGGGT (SEQ ID NO: 182) or RYWDFDVFGGGT (SEQ ID NO: 183).

In another aspect, the invention relates to a peptide that is specific for (as defined herein) for human serum albumin and that comprises an amino acid sequence chosen from RYWDYDVFGGGTP (SEQ ID NO: 184); RDWDFDVFGGGTP (SEQ ID NO: 185); RSWDFDVFGGGTP (SEQ ID NO: 186) or RYWDFDVFGGGTP (SEQ ID NO: 187); and in particular chosen from RDWDFDVFGGGTP (SEQ ID NO: 185); RSWDFDVFGGGTP (SEQ ID NO: 186) or RYWDFDVFGGGTP (SEQ ID NO: 187).

In another aspect, the invention relates to a peptide that is specific for (as defined herein) for human serum albumin and that comprises an amino acid sequence chosen from

```
RYWDYDVFGGGTPV;     (SEQ ID NO: 188)

RDWDFDVFGGGTPV;     (SEQ ID NO: 189)

RSWDFDVFGGGTPV      (SEQ ID NO: 190)
or

RYWDFDVFGGGTPV;     (SEQ ID NO: 191)
``` and in particular chosen from RDWDFDVFGGGTPV (SEQ ID NO: 189); RSWDFDVFGGGTPV (SEQ ID NO: 190) or RYWDFDVFGGGTPV (SEQ ID NO: 191).

In another aspect, the invention relates to a peptide that is specific for (as defined herein) for human serum albumin and that comprises the sequence motif RXWD (in which X is chosen from W, Y, F, S or D) and the sequence motif FGGG.

In another aspect, the invention relates to a peptide that is specific for (as defined herein) for human serum albumin and that comprises the sequence motif RXWD (in which X is preferably chosen from W, Y, F, S or D) and the sequence motif DVFGGG (SEQ ID NO: 129) or DAFGGG (SEQ ID NO: 192)

In another aspect, the invention relates to a peptide that is specific for (as defined herein) for human serum albumin and that comprises the sequence motif RXWD (in which X is preferably chosen from W, Y, F, S or D) and the sequence motif DVFGGGT (SEQ ID NO:133), DVFGGGS (SEQ ID NO: 193) of DAFGGGT (SEQ ID NO:194).

In preferred aspects, all the above peptides are preferably further such that they bind better to human serum albumin than the amino acid sequence of SEQ ID NO:1 and more preferably such that they bind equally good and more preferably better (as defined herein) to HSA than the amino acid sequence 56E4 (SEQ ID NO: 14).

In another aspect, the above peptides may be affinity matured variants of the amino acid sequence 56E4 (SEQ ID NO:14).

Also, where the above peptides are said to contain the sequence motif RXWD, either (i) the Arg (R) residue in this motif is capable of forming a hydrogen bond with the amino acid residues Asn (N) 133 & Asn (N) 135 of human serum albumin and/or capable of forming electrostatic interactions with the main-chain oxygen atoms of the Pro (P) 134 and Leu (L) 136 residues of human serum albumin; and/or (ii) the Trp (W) residue in this motif is capable of forming electrostatic interactions with the Arg (R) 138 residue of human serum albumin; and preferably both (i) and (ii) apply.

As mentioned, all these peptides may be as further described herein for the amino acid sequences of the invention.

In another aspect, the invention relates to a peptide that is specific for (as defined herein) for human serum albumin that comprises the sequence motif RXWD (in which X may be any amino acid, but is most preferably chosen from W, Y, F, S or D), in which (i) the Arg (R) residue in this motif is capable of forming a hydrogen bond with the amino acid residues Asn (N) 133 & Asn (N) 135 of human serum albumin and/or capable of forming electrostatic interactions with the main-chain oxygen atoms of the Pro (P) 134 and Leu (L) 136 residues of human serum albumin; and/or (ii) the Trp (W) residue in this motif is capable of forming electrostatic interactions with the Arg (R) 138 residue of human serum albumin; and preferably both (i) and (ii) apply. This peptide preferably further contains the sequence motif FGGG, more preferably the sequence motif DVFGGG (SEQ ID NO:129), and even more preferably the sequence motif DVGGGGT (SEQ ID NO:133).

Again, such peptides are preferably further such that they bind better to human serum albumin than the amino acid sequence of SEQ ID NO:1 and more preferably such that they bind equally good and more preferably better (as defined herein) to HSA than the amino acid sequence 56E4 (SEQ ID NO: 14); and/or may be affinity matured variants of the amino acid sequence 56E4 (SEQ ID NO:14); and may further generally be as further described herein.

In another aspect, the invention relates to a peptide that competes with the peptide of SEQ ID NO:1 for binding to human serum albumin, and/or that cross-blocks (as defined herein) the binding of the peptide of SEQ ID NO:1 to human serum albumin; and that binds better (as defined herein) to human serum albumin than the peptide of SEQ ID NO:1.

In another aspect, the invention relates to a peptide that competes with the peptide of SEQ ID NO:1 for binding to human serum albumin, and/or that cross-blocks (as defined herein) the binding of the peptide of SEQ ID NO:1 to human serum albumin; and that binds better (as defined herein) to human serum albumin than the peptide of SEQ ID NO:14. Such a peptide may be as further described herein.

In another aspect, the invention relates to a peptide that competes with the peptide of SEQ ID NO:14 for binding to human serum albumin, and/or that cross-blocks (as defined herein) the binding of the peptide of SEQ ID NO:14 to human serum albumin; and that binds better (as defined herein) to human serum albumin than the peptide of SEQ ID NO:1. Such a peptide may be as further described herein.

In another aspect, the invention relates to a peptide that competes with the peptide of SEQ ID NO:14 for binding to human serum albumin, and/or that cross-blocks (as defined herein) the binding of the peptide of SEQ ID NO:14 to human serum albumin; and that binds better (as defined herein) to human serum albumin than the peptide of SEQ ID NO:14. Such a peptide may be as further described herein.

The above peptides may be as further described herein; and may for example be affinity matured variants of the peptide of SEQ ID NO:1, and may in particular be affinity matured variants of the peptide of SEQ ID NO: 14. Also, and in particular, the above peptides may compete with the peptide of SEQ ID NO:1 or SEQ ID NO:14, respectively, for binding to one or more of the following amino acid residues of human serum albumin (numbering as indicated in Example 8): Asn (N) 133; Pro (P) 134; Asn (N) 135; Leu (L) 136; Leu (L) 139; Arg (R) 141; Tyr (Y) 162; Glu (E) 165; Ile (I) 166; His (H) 170; Phe (F) 173; Phe (F) 181; Gly (G) 213; Lys (K) 214; Ser (S) 217; Gln (Q) 483; and/or Lys (K) 543; more in particular to an epitope on human serum albumin that comprises either (i) the stretch of amino acid residues that comprises the residues Asn (N) 133; Pro (P) 134; Asn (N) 135; Leu (L) 136; Leu (L) 139 and Arg (R) 141; and/or (ii) the stretch of amino acid residues that comprises the residues Tyr (Y) 162; Glu (E) 165; Ile (I) 166; His (H) 170; Phe (F) 173; Phe (F) 181; and/or (iii) the stretch of amino acid residues that comprises the residues Gly (G) 213; Lys (K) 214 and Ser (S) 217; and even more in particular with a hydrophobic subpocket on human serum albumin that is comprises (amongst others) residues the residues Leu (L) 139, Glu (E) 165, Ile (I) 166, His (H) 170, Phe (F) 173, Phe (F) 181, Gly (G) 213, Lys (K) 214, Ser (S) 217 and Gln (Q) 483.

In one specific aspect, the invention relates to compounds of the invention that comprise at least one amino acid sequence of the invention (which may be as further described herein), and at least one single domain antibody (and in particular a Nanobody) against vWF, such as one of the Nanobodies described in WO 04/062551 or WO 06/1222825).

In particular, such a compound of the invention may comprise two single domain antibodies (and in particular two Nanobodies) against vWF (such as two of the Nanobodies described in WO 04/062551 or WO 06/1222825), and at least one amino acid sequence of the invention. Such a compound may have one of the configurations exemplified above. For example, in such a compound, the two single domain against vWF may be directly linked to each other, or may be linked to each other via a linker that comprises at least one, and preferably two, amino acid sequences of the invention.

Preferably, however, such a compound comprises two single domain antibodies (and in particular Nanobodies) against vWF that are linked to each other via a suitable linker (that does not contain an amino acid sequence of the invention) so as to form a bivalent anti-vWF construct (for which again reference is made to WO 04/062551 or WO 06/1222825), in which one or more amino acid sequences of the invention (which may be in the form of a tandem repeat as described herein) are linked to either the C-terminus, to the N-terminus or to both the C-terminus and the N-terminus of the bivalent anti-vWF construct (again, optionally via a suitable linker).

More preferably, such a compound comprises two single domain antibodies (and in particular Nanobodies) against vWF (that may be different but are preferably the same) that are linked to each other via a suitable linker (that does not contain an amino acid sequence of the invention) so as to form a bivalent anti-vWF construct, which is linked (at the C-terminus, the N-terminus or both the C-terminus and the N-terminus optionally via a suitable linker) to a tandem repeat of amino acid sequences of the invention as described herein (in particular, comprising two amino acid sequences of the invention, linked via a suitable linker). Most preferably, such a tandem repeat is linked to the C-terminus of the bivalent anti-vWF construct.

The (preferably two) single domain antibodies (and in particular Nanobodies) against vWF present in these compounds are preferably directed against the activated confirmation of the A1 domain of vWF (see again WO 04/062551 and in particular WO 06/1222825). In particular, the (preferably two) single domain antibodies (and in particular Nanobodies) against vWF present in these compounds may be one of the Nanobodies described in WO 06/1222825; and more in particular humanized versions of the Nanobody 12A2 (SEQ ID NO: 71 of WO 06/1222825), such as the humanized versions of 12A2 described in WO 06/1222825 (see for example SEQ ID NO's: 90 to 94 of WO 06/1222825, with the humanized variant of 12A2H1/SEQ ID NO:90 being particularly preferred).

Some preferred, but non-limiting examples of such anti-vWF compounds of the invention are described and used in Examples 12-15 below. Other preferred Examples are as described in Example 12, but comprise a humanized variant of 12A2 instead of 12A2 (as present in the constructs of Example 12), and in particular 12A2H1 (SEQ ID NO:90 of WO 06/1222825). Another preferred example of such a compound would comprise the anti-vWF construct of SEQ ID NO:90 of WO 06/1222825, linked at its N-terminus (less preferred) or its C-terminus (preferred) to an amino acid sequence of the invention, and preferably to a tandem repeat of amino acid sequences of the invention as described herein.

A most preferred example is a compound that comprises the anti-vWF construct of SEQ ID NO:90 of WO 06/1222825, linked at its N-terminus (less preferred) or its C-terminus (preferred) to an amino acid sequence of the invention, and preferably to a tandem repeat (as described herein) that comprises two of the amino acid sequence 59C2, 59F2 and/or 59H2 of the invention.

The invention also relates to a nucleotide sequence or nucleic acid that encodes an amino acid sequence of the invention or a polypeptide of the invention (also referred to herein as a "nucleotide sequence of the invention" or a "nucleic acid of the invention").

The invention also relates to a host or host cell that contains a nucleotide sequence or nucleic acid of the invention and/or that expresses (or is capable of expressing) an amino acid sequence of the invention or a polypeptide of the invention.

The invention also relates to methods for preparing the amino acid sequences and compounds of the invention, which methods are as further described herein.

The invention further relates to a composition that comprises at least one amino acid sequence of the invention or compound of the invention; and optionally one or more further suitable components or constituents. In particular, the invention relates to a pharmaceutical composition that comprises at least one amino acid sequence of the invention, compound of the invention, or nucleic acid of the invention; and optionally at least one pharmaceutically acceptable carrier, diluent or excipient.

The invention also encompasses some other methods for preparing the constructs and compounds of the invention, which generally comprise the step of linking at least one amino acid sequence of the invention to at least one therapeutic moiety, optionally via one or more suitable linkers or spacers. This may be performed in any suitable manner known per se, for example depending on the linker(s) used (if any), and may for example comprise techniques for chemical linking known per se in the art, for example by formation of one or more covalent bonds. The one or more amino acid sequences of the invention and the one or more therapeutic moieties may be as further described herein. Again, the one or more amino acid sequences of the invention preferably comprise a disulphide bridge as described herein.

The invention also relates to compound or construct that is obtained via any of the above methods; and also to a pharmaceutical composition that comprises at least one such compound or construct and optionally at least one pharmaceutically acceptable carrier, diluent or excipient.

The invention also relates to uses of the amino acid sequences of the invention. Generally, these uses comprise any use known per se for binding units, binding domains or amino acid sequences that can bind to serum proteins in general, and serum albumin in particular. Such uses will be clear to the skilled person, and not only include increasing the half-life to therapeutic moieties, entities or drugs; but also (or in addition) directing therapeutic moieties, entities or drugs to parts of the body or tissues where serum albumin is present and/or accumulates in the body, such as inflammation sites or joints.

The invention further relates to therapeutic uses of polypeptide or protein constructs or fusion proteins and to pharmaceutical compositions comprising such polypeptide or protein constructs or fusion proteins.

DETAILED DESCRIPTION OF THE INVENTION

In the present description, examples and claims:
a) Unless indicated otherwise herein (for example, in Example 8), amino acid residues and positions in the amino acid sequences of the invention will be numbered with reference to the corresponding amino acid residues and positions in the

```
AASYSDYDVFGGGTDFGP.        (SEQ ID NO: 1)
``` b) Unless indicated otherwise herein (for example, in Example 8), amino acid substitutions will be mentioned with reference to the amino acid residue present at the corresponding position in the amino acid sequence AASYSDYDVFGGGTDFGP (SEQ ID NO:1). For example, S3R refers to a substitution, compared to the amino acid sequence AASYSDYDVFGGGTDFGP (SEQ ID NO:1), of the serine residue S at position 3 into arginine (R).

c) Unless indicated or defined otherwise, all terms used have their usual meaning in the art, which will be clear to the skilled person. Reference is for example made to the standard handbooks mentioned in paragraph a) on page 46 of WO 08/020,079 of Ablynx N.V. entitled "Amino acid sequences directed against IL-6R and polypeptides comprising the same for the treatment of diseases and disorders associated with Il-6 mediated signalling".

d) Unless indicated otherwise, the terms "immunoglobulin sequence", "sequence", "nucleotide sequence" and "nucleic acid" are as described in paragraph b) on page 46 of WO 08/020,079.

e) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

f) Amino acid residues will be indicated according to the standard three-letter or one-letter amino acid code, as mentioned in Table A;

TABLE A

| one-letter and three-letter amino acid code | | | |
|---|---|---|---|
| Nonpolar, uncharged (at pH 6.0-7.0)[3] | Alanine | Ala | A |
| | Valine | Val | V |
| | Leucine | Leu | L |
| | Isoleucine | Ile | I |
| | Phenylalanine | Phe | F |
| | Methionine[1] | Met | M |
| | Tryptophan | Trp | W |
| | Proline | Pro | P |
| Polar, uncharged (at pH 6.0-7.0) | Glycine[2] | Gly | G |
| | Serine | Ser | S |
| | Threonine | Thr | T |
| | Cysteine | Cys | C |
| | Asparagine | Asn | N |
| | Glutamine | Gln | Q |
| | Tyrosine | Tyr | Y |
| Polar, charged (at pH 6.0-7.0) | Lysine | Lys | K |
| | Arginine | Arg | R |
| | Histidine[4] | His | H |
| | Aspartate | Asp | D |
| | Glutamate | Glu | E |

Notes:
[1] Sometimes also considered to be a polar uncharged amino acid.
[2] Sometimes also considered to be a nonpolar uncharged amino acid.
[3] As will be clear to the skilled person, the fact that an amino acid residue is referred to in this Table as being either charged or uncharged at pH 6.0 to 7.0 does not reflect in any way on the charge said amino acid residue may have at a pH lower than 6.0 and/or at a pH higher than 7.0; the amino acid residues mentioned in the Table can be either charged and/or uncharged at such a higher or lower pH, as will be clear to the skilled person.
[4] As is known in the art, the charge of a His residue is greatly dependant upon even small shifts in pH, but a His residue can generally be considered essentially uncharged at a pH of about 6.5.

g) For the purposes of comparing two or more nucleotide sequences, the percentage of "sequence identity" between a first nucleotide sequence and a second nucleotide sequence may be calculated or determined as described in paragraph c) on page 49 of WO 08/020,079 (incorporated herein by reference), such as by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position); or using a suitable computer algorithm or technique, again as described in paragraph c) on pages 49 of WO 08/020,079 (incorporated herein by reference).

h) For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein.

Alternatively, the degree of sequence identity between two amino acid sequences may be calculated using a known computer algorithm, such as those mentioned above for determining the degree of sequence identity for nucleotide sequences, again using standard settings.

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-3 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81:

140-144, 1984; Kyte & Doolittle; J. Molec. Biol. 157: 105-132, 1981, and Goldman et al., Ann. Rev. Biophys. Chem. 15: 321-353, 1986, all incorporated herein in their entirety by reference. Information on the primary, secondary and tertiary structure of Nanobodies® is given in the description herein and in the general background art cited above. Also, for this purpose, the crystal structure of a VHH domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

i) Amino acid sequences and nucleic acid sequences are said to be "exactly the same" if they have 100% sequence identity (as defined herein) over their entire length;

j) When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences;

k) When a nucleotide sequence or amino acid sequence is said to "comprise" another nucleotide sequence or amino acid sequence, respectively, or to "essentially consist of" another nucleotide sequence or amino acid sequence, this has the meaning given in paragraph i) on pages 51-52 of WO 08/020,079.

l) The term "in essentially isolated form" has the meaning given to it in paragraph j) on pages 52 and 53 of WO 08/020,079.

m) The terms "domain" and "binding domain" have the meanings given to it in paragraph k) on page 53 of WO 08/020,079.

n) The terms "antigenic determinant" and "epitope", which may also be used interchangeably herein. have the meanings given to it in paragraph 1) on page 53 of WO 08/020, 079.

o) As further described in paragraph m) on page 53 of WO 08/020,079, an amino acid sequence (such as a Nanobody®, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" or "specific for" said antigenic determinant, epitope, antigen or protein.

p) The terms "specificity" and "specific for" have the meaning given to it in paragraph n) on pages 53-56 of WO 08/020,079; and as mentioned therein refers to the number of different types of antigens or antigenic determinants to which a particular antigen-binding molecule or antigen-binding protein (such as a Nanobody® or a polypeptide of the invention) molecule can bind. The specificity of an antigen-binding protein can be determined based on affinity and/or avidity, as described on pages 53-56 of WO 08/020,079 (incorporated herein by reference), which also describes some preferred techniques for measuring binding between an antigen-binding molecule (such as a Nanobody® or polypeptide of the invention) and the pertinent antigen. Typically, antigen-binding proteins (such as the amino acid sequences and/or compounds of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than 104 mol/liter (or any $K_A$ value lower than $10^4$ $M^{-1}$) liters/mol is generally considered to indicate non-specific binding. Preferably, an amino acid sequence or compound of the invention will bind to the desired serum protein with an affinity less than 1000 nM, preferably less than 500 nM, preferably less than 200 nM, more preferably less than 10 nM, such as less than 500 µM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein. As will be clear to the skilled person, and as described on pages 53-56 of WO 08/020, 079, the dissociation constant may be the actual or apparent dissociation constant. Methods for determining the dissociation constant will be clear to the skilled person, and for example include the techniques mentioned on pages 53-56 of WO 08/020,079 q) The half-life of an amino acid sequence, compound or polypeptide of the invention can generally be defined as the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally involve the steps of suitably administering to a warm-blooded animal (i.e. to a human or to another suitable mammal, such as a mouse, rabbit, rat, pig, dog or a primate, for example monkeys from the genus *Macaca* (such as, and in particular, cynomolgus monkeys (*Macaca fascicularis*) and/or rhesus monkeys (*Macaca mulatta*)) and baboon (*Papio ursinus*)) a suitable dose of the amino acid sequence, compound or polypeptide of the invention; collecting blood samples or other samples from said animal; determining the level or concentration of the amino acid sequence, compound or polypeptide of the invention in said blood sample; and calculating, from (a plot of) the data thus obtained, the time until the level or concentration of the amino acid sequence, compound or polypeptide of the invention has been reduced by 50% compared to the initial level upon dosing. Reference is for example made to the Experimental Part below, as well as Dennis et al., J. Biol. Chem. 277:35035-42 (2002) to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982).

As will also be clear to the skilled person (see for example pages 6 and 7 of WO 04/003019 and in the further references cited therein), the half-life can be expressed using parameters such as the t½-alpha, t½-beta and the area under the curve (AUC). In the present specification, an "increase in half-life" refers to an increase in any one of these parameters, such as any two of these parameters, or essentially all three these parameters. As used herein "increase in half-life" or "increased half-life" in particular refers to an increase in the t½-beta, either with or without an increase in the t½-alpha and/or the AUC or both.

r) In the context of the present invention, "modulating" or "to modulate" generally means either reducing or inhibiting the activity of, or alternatively increasing the activity of, a target or antigen, as measured using a suitable in vitro, cellular or in vivo assay. In particular, "modulating" or "to modulate" may mean either reducing or inhibiting the activity of, or alternatively increasing a (relevant or intended) biological activity of, a target or antigen, as measured using a suitable in vitro, cellular or in vivo assay (which will usually depend on the target or antigen involved), by at least 1%, preferably at least 5%, such as at least 10% or at least 25%, for example by at least 50%, at least 60%, at least 70%, at least 80%, or 90% or more, compared to activity of the target or antigen in the same assay under the same conditions but without the presence of the construct of the invention.

As will be clear to the skilled person, "modulating" may also involve effecting a change (which may either be an increase or a decrease) in affinity, avidity, specificity and/or selectivity of a target or antigen for one or more of its ligands, binding partners, partners for association into a homomultimeric or heteromultimeric form, or substrates; and/or effecting a change (which may either be an increase or a decrease) in the sensitivity of the target or antigen for one or more conditions in the medium or surroundings in which the target or antigen is present (such as pH, ion strength, the presence of co-factors, etc.), compared to the same conditions but without the presence of the construct of the invention. As will be clear to the skilled person, this may again be determined in any suitable manner and/or using any suitable assay known per se, depending on the target or antigen involved.

"Modulating" may also mean effecting a change (i.e. an activity as an agonist, as an antagonist or as a reverse agonist, respectively, depending on the target or antigen and the desired biological or physiological effect) with respect to one or more biological or physiological mechanisms, effects, responses, functions, pathways or activities in which the target or antigen (or in which its substrate(s), ligand(s) or pathway(s) are involved, such as its signalling pathway or metabolic pathway and their associated biological or physiological effects) is involved. Again, as will be clear to the skilled person, such an action as an agonist or an antagonist may be determined in any suitable manner and/or using any suitable (in vitro and usually cellular or in assay) assay known per se, depending on the target or antigen involved. In particular, an action as an agonist or antagonist may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the construct of the invention.

Modulating may for example also involve allosteric modulation of the target or antigen; and/or reducing or inhibiting the binding of the target or antigen to one of its substrates or ligands and/or competing with a natural ligand, substrate for binding to the target or antigen. Modulating may also involve activating the target or antigen or the mechanism or pathway in which it is involved. Modulating may for example also involve effecting a change in respect of the folding or confirmation of the target or antigen, or in respect of the ability of the target or antigen to fold, to change its confirmation (for example, upon binding of a ligand), to associate with other (sub)units, or to disassociate.

Modulating may for example also involve effecting a change in the ability of the target or antigen to transport other compounds or to serve as a channel for other compounds (such as ions).

Modulating may be reversible or irreversible, but for pharmaceutical and pharmacological purposes will usually be in a reversible manner.

s) In respect of a target or antigen, the term "interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerization (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signalling, biological mechanism or biological effect in which the target or antigen is involved) is modulated (as defined herein).

t) An amino acid sequence or polypeptide is said to be "specific for" a first target or antigen compared to a second target or antigen when is binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10,000 times or more better than the affinity with which said amino acid sequence or polypeptide binds to the second target or polypeptide. For example, the first antigen may bind to the target or antigen with a $K_D$ value that is at least 10 times less, such as at least 100 times less, and preferably at least 1000 times less, such as 10,000 times less or even less than that, than the $K_D$ with which said amino acid sequence or polypeptide binds to the second target or polypeptide. Preferably, when an amino acid sequence or polypeptide is "specific for" a first target or antigen compared to a second target or antigen, it is directed against (as defined herein) said first target or antigen, but not directed against said second target or antigen.

u) An amino acid sequence is said to be "cross-reactive" for two different antigens or antigenic determinants (such as serum albumin from two different species of mammal, such as human serum albumin and cyno serum albumin) if it is specific for (as defined herein) both these different antigens or antigenic determinants.

v) By binding that is "essentially independent of the pH" is generally meant herein that the association constant ($K_A$) of the amino acid sequence with respect to the serum protein (such as serum albumin) at the pH value(s) that occur in a cell of an animal or human body (as further described herein) is at least 5%, such as at least 10%, preferably at least 25%, more preferably at least 50%, even more preferably at least 60%, such as even more preferably at least 70%, such as at least 80% or 90% or more (or even more than 100%, such as more than 110%, more than 120% or even 130% or more, or even more than 150%, or even more than 200%) of the association constant ($K_A$) of the amino acid sequence with respect to the same serum protein at the pH value(s) that occur outside said cell. Alternatively, by binding that is "essentially independent of the pH" is generally meant herein that the $k_{off}$ rate (measured by Biacore—see e.g. Experiment 2) of the amino acid sequence with respect to the serum protein (such as serum albumin) at the pH value(s) that occur in a cell of an animal or human body (as e.g. further described herein, e.g. pH around 5.5, e.g. 5.3 to 5.7) is at least 5%, such as at least 10%, preferably at least 25%, more preferably at least 50%, even more preferably at least 60%, such as even more preferably at least 70%, such as at least 80% or 90% or more (or even more than 100%, such as more than 110%, more than 120% or even 130% or more, or even more than 150%, or even more than 200%) of the $k_{off}$ rate of the amino acid sequence with respect to the same serum protein at the pH value(s) that occur outside said cell, e.g. pH 7.2 to 7.4. By "the pH value(s) that occur in a cell of an animal or human body" is meant the pH value(s) that may occur inside a cell, and in particular inside a cell that is involved in the recycling of the serum protein. In particular, by "the pH value(s) that occur in a cell of an animal or human body" is meant the pH value(s) that may occur inside a (sub)cellular compartment or vesicle that is involved in recycling of the serum protein (e.g. as a result of pinocytosis, endocytosis, transcytosis, exocytosis and phagocytosis or a similar mechanism of uptake or internalization into said cell), such as an endosome, lysosome or pinosome.

w) The terms "cross-block", "cross-blocked" and "cross-blocking" are used interchangeably herein to mean the ability of an amino acid sequence or other binding agents (such as a Nanobody, polypeptide or compound or construct of the invention) to interfere with the binding of other amino acid sequences or binding agents of the invention to a given target. The extend to which an amino acid sequence or other binding agents of the invention is able to interfere with the binding of another to the relevant, and therefore whether it can be said to cross-block according to the invention, can be determined using competition binding assays. One particularly suitable quantitative cross-blocking assay uses a Biacore machine which can measure the extent of interactions using surface plasmon resonance technology. Another suitable quantitative cross-blocking assay uses an ELISA-based approach to measure competition between amino acid sequences or other binding agents in terms of their binding to the target.

The following generally describes a suitable Biacore assay for determining whether an amino acid sequence or other binding agent cross-blocks or is capable of cross-blocking according to the invention. It will be appreciated that the assay can be used with any of the amino acid sequences or other binding agents described herein. The Biacore machine (for example the Biacore 3000) is operated in line with the manufacturer's recommendations. Thus in one cross-blocking assay, the target protein is coupled to a CM5 Biacore chip using standard amine coupling chemistry to generate a surface that is coated with the target. Typically 200-800 resonance units of the target would be coupled to the chip (an amount that gives easily measurable levels of binding but that is readily saturable by the concentrations of test reagent being used). Two test amino acid sequences (termed A* and B*) to be assessed for their ability to cross-block each other are mixed at a one to one molar ratio of binding sites in a suitable buffer to create the test mixture. When calculating the concentrations on a binding site basis the molecular weight of an amino acid sequence is assumed to be the total molecular weight of the amino acid sequence divided by the number of target binding sites on that amino acid sequence. The concentration of each amino acid sequence in the test mix should be high enough to readily saturate the binding sites for that amino acid sequence on the target molecules captured on the Biacore chip. The amino acid sequences in the mixture are at the same molar concentration (on a binding basis) and that concentration would typically be between 1.00 and 1.5 micromolar (on a binding site basis). Separate solutions containing A* alone and B* alone are also prepared. A* and B* in these solutions should be in the same buffer and at the same concentration as in the test mix. The test mixture is passed over the target-coated Biacore chip and the total amount of binding recorded. The chip is then treated in such a way as to remove the bound amino acid sequences without damaging the chip-bound target. Typically this is done by treating the chip with 30 mM HCl for 60 seconds. The solution of A* alone is then passed over the target-coated surface and the amount of binding recorded. The chip is again treated to remove all of the bound amino acid sequences without damaging the chip-bound target. The solution of B* alone is then passed over the target-coated surface and the amount of binding recorded. The maximum theoretical binding of the mixture of A* and B* is next calculated, and is the sum of the binding of each amino acid sequence when passed over the target surface alone. If the actual recorded binding of the mixture is less than this theoretical maximum then the two amino acid sequences are cross-blocking each other. Thus, in general, a cross-blocking amino acid sequence or other binding agent according to the invention is one which will bind to the target in the above Biacore cross-blocking assay such that, during the assay and in the presence of a second amino acid sequence or other binding agent of the invention, the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two amino acid sequences or binding agents in combination. The Biacore assay described above is a primary assay used to determine if amino acid sequences or other binding agents cross-block each other according to the invention. On rare occasions particular amino acid sequences or other binding agents may not bind to target coupled via amine chemistry to a CM5 Biacore chip (this usually occurs when the relevant binding site on target is masked or destroyed by the coupling to the chip). In such cases cross-blocking can be determined using a tagged version of the target, for example a N-terminal His-tagged version. In this particular format, an anti-His amino acid sequence would be coupled to the Biacore chip and then the His-tagged target would be passed over the surface of the chip and captured by the anti-His amino acid sequence. The cross blocking analysis would be carried out essentially as described above, except that after each chip regeneration cycle, new His-tagged target would be loaded back onto the anti-His amino acid sequence coated surface. In addition to the example given using N-terminal His-tagged target, C-terminal His-tagged target could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

The following generally describes an ELISA assay for determining whether an amino acid sequence or other binding agent directed against a target cross-blocks or is capable of cross-blocking as defined herein. It will be appreciated that the assay can be used with any of the amino acid sequences (or other binding agents such as polypeptides of the invention) described herein. The general principal of the assay is to have an amino acid sequence or binding agent that is directed against the target coated onto the wells of an ELISA plate. An excess amount of a second, potentially cross-blocking, anti-target amino acid sequence is added in solution (i.e. not bound to the ELISA plate). A limited amount of the target is then added to the wells. The coated amino acid sequence and the amino acid sequence in solution compete for binding of the limited number of target molecules. The plate is washed to remove excess target that has not been bound by the coated amino acid sequence and to also remove the second, solution phase amino acid sequence as well as any complexes formed between the second, solution phase amino acid sequence and target. The amount of bound target is then measured using a reagent that is appropriate to detect the target. An amino acid sequence in solution that is able to cross-block the coated amino acid sequence will be able to cause a decrease in the number of target molecules that the coated amino acid sequence can bind relative to the number of target molecules that the coated amino acid sequence can bind in the absence of the second, solution phase, amino acid sequence. In the instance where the first amino acid sequence, e.g. an Ab-X, is chosen to be the immobilized amino acid sequence, it is coated onto the wells of the ELISA plate, after which the plates are blocked with a suitable blocking solution to minimize non-specific binding of reagents that are subsequently added. An excess amount of the second amino acid sequence, i.e. Ab-Y, is then added to the ELISA plate such that the moles of Ab-Y target binding sites per well are at least 10 fold higher than the moles of Ab-X target binding sites that were used, per well, during the coating of the ELISA plate. Target is then added such that the moles of target added per well are at least 25-fold lower than the moles of Ab-X target binding sites that were used for coating each well. Following a suitable incubation period the ELISA plate is washed and a reagent for detecting the target is added to measure the amount of target specifically bound by the coated anti[target amino acid sequence (in this case Ab-X). The background signal for the assay is defined as the signal obtained in wells with the coated amino acid sequence (in this case Ab-X), second solution phase amino acid sequence (in this case Ab-Y), target buffer only (i.e. without target) and target detection reagents. The positive control signal for the assay is defined as the signal obtained in wells with the coated amino acid sequence (in this case Ab-X), second solution phase amino acid sequence buffer only (i.e. without second solution phase amino acid sequence), target and target detection reagents. The ELISA assay may be run in such a manner so as to have the positive control signal be at least 6 times the background signal.

To avoid any artefacts (e.g. significantly different affinities between Ab-X and Ab-Y for the target) resulting from the choice of which amino acid sequence to use as the coating amino acid sequence and which to use as the second (competitor) amino acid sequence, the cross-blocking assay may to be run in two formats: 1) format 1 is where Ab-X is the amino acid sequence that is coated onto the ELISA plate and Ab-Y is the competitor amino acid sequence that is in solution and 2) format 2 is where Ab-Y is the amino acid sequence that is coated onto the ELISA plate and Ab-X is the competitor amino acid sequence that is in solution. Ab-X and Ab-Y are defined as cross-blocking if, either in format 1 or in format 2, the solution phase anti-target amino acid sequence is able to cause a reduction of between 60% and 100%, specifically between 70% and 100%, and more specifically between 80% and 100%, of the target detection signal {i.e. the amount of target bound by the coated amino acid sequence) as compared to the target detection signal obtained in the absence of the solution phase anti-target amino acid sequence (i.e. the positive control wells).

x) Any Figures, Sequence Listing and the Experimental Part/Examples are only given to further illustrate the invention and should not be interpreted or construed as limiting the scope of the invention and/or of the appended claims in any way, unless explicitly indicated otherwise herein.

For a general description of heavy chain antibodies and the variable domains thereof, reference is inter alia made to the prior art cited herein, to the review article by Muyldermans in Reviews in Molecular Biotechnology 74 (2001), 277-302; as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference.

The amino acid sequences of the invention may be prepared in a manner known per se. For example, a desired amino acid sequence may be prepared by peptide synthesis or by suitably expressing a nucleic acid encoding said amino acid sequence. A desired nucleotide sequence may be prepared by techniques of nucleic acid synthesis known per se.

One method for preparing the amino acid sequences or polypeptides of the invention generally comprises at least the step of:

a) expressing a nucleotide sequence or nucleic acid of the invention;

and optionally further comprises:

b) isolating the amino acid sequence of the invention or the polypeptide of the invention, respectively, so expressed.

Another method for preparing the amino acid sequences or polypeptides of the invention generally comprises at least the step of:

a) cultivating or maintaining a host or host cell as described herein under conditions such that said host or host cell produces an amino acid sequence or polypeptide of the invention;

and optionally further comprising:

b) isolating the amino acid sequence of the invention or polypeptide of the invention respectively, thus obtained.

Where an amino acid sequence of the invention is to be used in a constrained format (i.e. comprising a disulphide bridge between the flanking sequences that flank the amino acid sequence of the invention), the above methods may also comprise a further step of forming such a disulphide bridge, as further described in PCT/EP2007/063348.

The invention also relates to the amino acid sequences, compounds, construct or polypeptides obtained via the above methods.

The amino acid sequences disclosed herein can be used with advantage as a fusion partner in order to increase the half-life of therapeutic moieties such as proteins, compounds (including, without limitation, small molecules) or other therapeutic entities.

Thus, in another aspect, the invention provides amino acid sequences that can be used as small peptides or peptide moieties for linking or fusing to a therapeutic compound in order to increase the half-life thereof, and constructs and fusion proteins comprising such peptides or peptide moieties, that can bind to a serum protein in such a way that, when the amino acid sequence, construct, or fusion protein of the invention is bound to a serum protein molecule, the half-life of the serum protein molecule is not (significantly) reduced (i.e. compared to the half-life of the serum protein molecule when the amino acid sequence, construct, or fusion protein is not bound thereto). In this aspect of the invention, by "not significantly reduced" is meant that the half-life of the serum protein molecule (as measured using a suitable technique known per se) is not reduced by more than 50%, preferably not reduced by more than 30%, even more preferably not reduced by more than 10%, such as not reduced by more than 5%, or essentially not reduced at all.

In another preferred, but non-limiting aspect, the amino acid sequences of the invention are preferably such that they bind to or otherwise associate with human serum albumin in such a way that, when the amino acid sequences are bound to or otherwise associated with a human serum albumin, the amino acid sequences exhibit a serum half-life in human of at least about 9 days (such as about 9 to 14 days), preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another aspect, the invention provides polypeptide or protein constructs that comprise or essentially consist of an amino acid sequence as disclosed herein.

The invention also relates to a compound or construct which comprises at least one amino acid sequence of the invention and at least one therapeutic moiety (also referred to herein as "compounds of the invention").

For example, and without limitation, a compound of the invention may comprise the at least one therapeutic moiety, that is linked to one, two, three, four or more amino acid sequences of the invention. For example, when the therapeutic moiety is a protein or polypeptide, the one or more amino acid sequences of the invention may be linked to the C-terminus of the protein or polypeptide (either directly or via a suitable spacer or linker); to the N-terminus of the protein or polypeptide (again either directly or via a suitable spacer or linker); or both to the C-terminus and the N-terminus. When a compound of the invention comprises two or more amino acid sequences of the invention, these may be the same or different.

The therapeutic moiety may also be linked (either at its C-terminus, its N-terminus, or both, and again either directly or via a suitable spacer or linker) to a multimer or concatamer that comprises at least two (such as two, three or four) amino acid sequences of the invention (which may be the same or different), that may either be linked directly to each other, or via a suitable linker or spacer. Such (bivalent, trivalent or multivalent) multimers or concatamers (and nucleotide sequences encoding the same, as well as compounds of the invention comprising the same) form a further aspect of the invention, and may bind to serum albumin with a higher avidity than a monomeric amino acid sequence of the invention.

Also, when a compound of the invention comprises two or more therapeutic moieties, each of these therapeutic moieties (or both) may be linked to one or more amino acid sequences of the invention, as further described herein. Also, the two or more therapeutic moieties may be linked to each other via a linker that comprises or essentially consists of one or more amino acid sequences of the invention (and optionally further linking amino acid sequences), and such a linker (as well as compounds of the invention comprising the same) form a further aspect of the invention.

In one aspect, the therapeutic moiety is directed against a desired antigen or target, is capable of binding to a desired antigen (and in particular capable of specifically binding to a desired antigen), and/or is capable of interacting with a desired target. In another embodiment, the at least one therapeutic moiety comprises or essentially consists of a therapeutic protein or polypeptide. In a further embodiment, the at least one therapeutic moiety comprises or essentially consists of an immunoglobulin or immunoglobulin sequence (including but not limited to a fragment of an immunoglobulin), such as an antibody or an antibody fragment (including but not limited to an ScFv fragment or Fab fragment). In yet another embodiment, the at least one therapeutic moiety comprises or essentially consists of an antibody variable domain, such as a heavy chain variable domain or a light chain variable domain.

In one preferred, but non-limiting aspect, the one or more therapeutic moieties or entities may be one or more binding units (as defined in PCT/EP2007/063348) or binding domains (as defined herein), i.e. binding units or domain that are capable of binding to a desired target, antigen or antigenic determinant (such as a therapeutically relevant target). As such, the compound of the invention may be a monovalent, bivalent, bispecific, multivalent or multispecific construct (as defined in PCT/EP2007/063348). The binding unit may generally comprise a scaffold-based binding unit or domain, such as binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al., Nat. Biotech 2005, Vol 23:1257), and binding moieties based on DNA or RNA including but not limited to DNA or RNA aptamers (Ulrich et al., Comb Chem High Throughput Screen 2006 9(8):619-32).

The amino acid sequences of the invention may also be linked to one of the "polypeptide drugs" referred to in the International application WO 05/118642 (Domantis Ltd.) or the International application 06/059106 (Domantis Ltd.); such as to one of the polypeptide drugs that are mentioned on pages 45 to 50 of WO 05/118642; antagonists of the interleukin 1 receptor (see pages 11-12 of WO 05/118642) including functional variants of IL-1ra; saporins (see pages 12-14 of WO 05/118642); the anticancer peptides listed in Table 8 of WO 05/118642; and insulinotropic agents or analogues thereof such as GLP-1 or GLP-1 analogues (see 06/059106).

In a preferred aspect, the at least one therapeutic moiety comprises or essentially consists of at least one domain antibody or single domain antibody, "dAb" or Nanobody®. Thus, for example, in a compound of the invention, one or more amino acid sequences of the invention may be fused or linked to one or more domain antibodies, single domain antibodies, "dAb's" or Nanobodies®, such that the resulting compound of the invention is a monovalent, bivalent, multivalent, bispecific or multispecific construct (in which the terms "monovalent", "bivalent", "multivalent", "bispecific" and "multispecific" are as described in PCT/EP2007/063348 or in the patent applications of Ablynx N.V. cited above).

Thus, one embodiment of the invention relates to a protein or polypeptide construct or fusion protein that comprises or essentially consists of at least one amino acid sequence of the invention and at least one immunoglobulin sequence, such as a domain antibody, a single domain antibody, a "dAb" or a Nanobody®.

Generally, a compound of the invention preferably has a half-life that is more than 1 hour, preferably more than 2 hours, more preferably of more than 6 hours, such as of more than 12 hours, and for example of about one day, two days, one week, two weeks or three weeks, and preferably no more than 2 months, although the latter may be less critical.

Preferably, the compounds or polypeptides of the invention that comprise at least one amino acid sequence of the invention and at least one therapeutic moiety preferably have a half-life that is at least 1.5 times, preferably at least 2 times, such as at least 5 times, for example at least 10 times or more than 20 times, greater than the half-life of the therapeutic moiety per se. For example, the compounds or polypeptides of the invention may have a half-life that is increased with more than 1 hours, preferably more than 2 hours, more preferably more than 6 hours, such as more than 12 hours, or even more than 24, 48 or 72 hours, compared to the therapeutic moiety per se.

In a preferred, but non-limiting aspect of the invention, such compounds or polypeptides of the invention have a serum half-life that is increased with more than 1 hours, preferably more than 2 hours, more preferably more than 6 hours, such as more than 12 hours, or even more than 24, 48 or 72 hours, compared to the therapeutic moiety per se.

The invention also relates to nucleotide sequences or nucleic acids that encode amino acid sequences, compounds, proteins, polypeptides, fusion proteins, or multivalent or multispecific constructs described herein. The invention further includes genetic constructs that include the foregoing nucleotide sequences or nucleic acids and one or more elements for genetic constructs known per se. The genetic construct may be in the form of a plasmid or vector. Such and other genetic constructs are known by those skilled in the art.

The invention also relates to hosts or host cells that contain such nucleotide sequences or nucleic acids, and/or that express (or are capable of expressing) amino acid sequences, compounds, proteins, polypeptides, fusion proteins, or multivalent or multispecific constructs described herein. Again, such hosts or host cells are known by those skilled in the art.

The invention also generally relates to a method for preparing amino acid sequences, compounds, proteins, polypeptides, fusion proteins, or multivalent or multispecific constructs as described herein, which method comprises cultivating or maintaining a host cell as described herein under conditions such that said host cell produces or expresses an amino acid sequence, compound, protein, polypeptide, fusion protein, or multivalent or multispecific construct as described herein, and optionally further comprises isolating the amino acid sequence, compound, protein, polypeptide, fusion protein, or multivalent or multispecific construct so produced. Again, such methods can be performed as generally described in the co-pending patent applications by Ablynx N.V. described herein, such as WO 04/041862 or WO 06/122825.

The invention also encompasses medical uses and methods of treatment encompassing the amino acid sequence, compound, or multivalent and multi specific compound of the invention, wherein said medical use or method is characterized in that said medicament is suitable for administration at intervals of at least about 50% of the natural half-life of human serum albumin.

The invention also relates to methods for extending or increasing the serum half-life of a therapeutic (i.e. a therapeutic moiety, compound, protein or other therapeutic entity). The methods include contacting the therapeutic with any of the foregoing amino acid sequences, such that the therapeutic is bound to or otherwise associated with the amino acid sequences, compounds, fusion proteins or constructs of the invention. In some embodiments, the therapeutic is a biological therapeutic, preferably a peptide or a polypeptide, in which case the step of contacting the therapeutic can include preparing a fusion protein by linking the peptide or polypeptide with the amino acid sequence, compound, fusion proteins or constructs of the invention.

These methods can further include administering the therapeutic to a subject after the therapeutic is bound to or associated with the amino acid sequence, compound, fusion protein or construct of the invention. In such methods, the serum half-life of the therapeutic is at least 1.5 times the half-life of therapeutic per se, or is increased by at least 1 hour (such as by at least 6 hours, preferably at least 12 hours, more preferably at least 1 day, such as more than 2 days, or even more than 5 days or more) compared to the half-life of therapeutic per se. In some preferred embodiments, the serum half-life of the therapeutic is at least 2 times, at least 5 times, at least 10 times, or more than 20 times greater than the half-life of the corresponding therapeutic moiety per se. In other preferred embodiments, the serum half-life of the therapeutic is increased by more than 2 hours, more than 6 hours or more than 12 hours compared to the half-life of the corresponding therapeutic moiety per se.

In the above methods, the serum half-life of the therapeutic is preferably increased or extended such that said serum half-life (i.e. of the compound of the invention thus obtained) is longer than the serum half-life of a corresponding compound or construct that comprises the therapeutic and the amino acid sequence of SEQ ID NO:1 (i.e. instead of the amino acid sequence of the invention). Preferably, the serum half-life of the compound of the invention is at least 5% longer, preferably at least 10% longer, more preferably at least 25% longer, or even more preferably at least than 50% longer, such as more than 100% longer or even more improved, compared to the serum half-life of a corresponding compound or construct that comprises the therapeutic and the amino acid sequence of SEQ ID NO:1 (i.e. instead of the amino acid sequence of the invention).

For example, in such methods, the serum half-life of the compound of the invention may be at least 1.1, such as at least 1.2 times, more preferably at least 1.5 times the half-life of the corresponding compound or construct that comprises the therapeutic and the amino acid sequence of SEQ ID NO:1 (i.e.

instead of the amino acid sequence of the invention), and/or may be increased by at least 1 hour (such as by at least 6 hours, preferably at least 12 hours, more preferably at least 1 day, such as more than 2 days, or even more than 5 days or more) compared to the half-life of a corresponding compound or construct that comprises the therapeutic and the amino acid sequence of SEQ ID NO:1 (i.e. instead of the amino acid sequence of the invention). In some preferred embodiments, the serum half-life of the compound of the invention is at least 2 times, at least 3 times or at least 5 times greater than the half-life of the corresponding compound or construct that comprises the therapeutic and the amino acid sequence of SEQ ID NO:1 (i.e. instead of the amino acid sequence of the invention).

In another aspect, the invention relates to a method for modifying a therapeutic such that the desired therapeutic level of said therapeutic is, upon suitable administration of said therapeutic so as to achieve said desired therapeutic level, maintained for a prolonged period of time.

The methods include contacting the therapeutic with any of the foregoing amino acid sequences, such that the therapeutic is bound to or otherwise associated with the amino acid sequences, compounds, fusion proteins or constructs of the invention. In some embodiments, the therapeutic is a biological therapeutic, preferably a peptide or polypeptide, in which case the step of contacting the therapeutic can include preparing a fusion protein by linking the peptide or polypeptide with the amino acid sequence, compound, fusion protein, or constructs of the invention.

These methods can further include administering the therapeutic to a subject after the therapeutic is bound to or otherwise associated with the amino acid sequence, compound, fusion protein, or construct of the invention, such that the desired therapeutic level is achieve upon such administration. In such methods, the time that the desired therapeutic level of said therapeutic is maintained upon such administration is at least 1.5 times the half-life of therapeutic per se, or is increased by at least 1 hour compared to the half-life of therapeutic per se. In some preferred embodiments, the time that the desired therapeutic level of said therapeutic is maintained upon such administration is at least 2 times, at least 5 times, at least 10 times or more than 20 times greater than the half-life of the corresponding therapeutic moiety per se. In other preferred embodiments, the time that the desired therapeutic level of said therapeutic is maintained upon such administration is increased by more than 2 hours, more than 6 hours or more than 12 hours compared to the half-life of the corresponding therapeutic moiety per se.

Preferably, the time that the desired therapeutic level of said therapeutic is maintained upon such administration is increased such that the therapeutic can be administered at a frequency that is as defined herein for the compounds of the invention.

In the above methods, the time that the desired therapeutic level of said therapeutic is maintained is preferably increased or extended such that said serum half-life (i.e. of the compound of the invention thus obtained) is longer than the time that the desired therapeutic level of said therapeutic is maintained by a corresponding compound or construct that comprises the therapeutic and the amino acid sequence of SEQ ID NO:1 (i.e. instead of the amino acid sequence of the invention). Preferably, the time that the desired therapeutic level of said therapeutic is maintained is at least 5% longer, preferably at least 10% longer, more preferably at least 25% longer, or even more preferably at least 50% longer, such as more than 100% longer or even more improved, compared to the time that the desired therapeutic level of said therapeutic is maintained by a corresponding compound or construct that comprises the therapeutic and the amino acid sequence of SEQ ID NO:1 (i.e. instead of the amino acid sequence of the invention).

For example, in such methods, the time that the desired therapeutic level of said therapeutic is maintained may be at least 1.1, such as at least 1.2 times, more preferably at least 1.5 times the time that the desired therapeutic level of said therapeutic is maintained by a corresponding compound or construct that comprises the therapeutic and the amino acid sequence of SEQ ID NO:1 (i.e. instead of the amino acid sequence of the invention), and/or may be increased by at least 1 hour (such as by at least 6 hours, preferably at least 12 hours, more preferably at least 1 day, such as more than 2 days, or even more than 5 days or more) compared to the time that the desired therapeutic level of said therapeutic is maintained by a corresponding compound or construct that comprises the therapeutic and the amino acid sequence of SEQ ID NO:1 (i.e. instead of the amino acid sequence of the invention). In some preferred embodiments, the time that the desired therapeutic level of said therapeutic is maintained is at least 2 times, at least 3 times or at least 5 times greater than the time that the desired therapeutic level of said therapeutic is maintained by a corresponding compound or construct that comprises the therapeutic and the amino acid sequence of SEQ ID NO:1 (i.e. instead of the amino acid sequence of the invention).

In another aspect, the invention relates to the use of a compound of the invention (as defined herein) for the production of a medicament that increases and/or extends the level of the therapeutic agent in said compound or construct in the serum of a patient such that said therapeutic agent in said compound or construct is capable of being administered at a lower dose as compared to the therapeutic agent alone (i.e. at essentially the same frequency of administration).

The invention also relates to a pharmaceutical composition that comprises at least one amino acid sequence, compound, protein, polypeptide, fusion protein, or multivalent or multispecific construct as described herein, and optionally at least one pharmaceutically acceptable carrier, diluent or excipient. Such preparations, carriers, excipients and diluents may generally be as described in the co-pending patent applications by Ablynx N.V. described herein, such as WO 04/041862 or WO 06/122825.

However, since the amino acid sequences, compounds, proteins, polypeptides, fusion proteins, or multivalent or multispecific constructs described herein have an increased half-life, they are preferably administered to the circulation. As such, they can be administered in any suitable manner that allows the amino acid sequences, compounds, proteins, polypeptides, fusion proteins, or multivalent or multispecific constructs to enter the circulation, such as intravenously, via injection or infusion, or in any other suitable manner (including oral administration, administration through the skin, intranasal administration, administration via the lungs, etc). Suitable methods and routes of administration will be clear to the skilled person, again for example also from the teaching of WO 04/041862 or WO 06/122825.

Thus, in another aspect, the invention relates to a method for the prevention and/or treatment of at least one disease or disorder that can be prevented or treated by the use of amino acid sequences, compounds, proteins, polypeptides, fusion proteins, or multivalent or multispecific constructs described herein, which method comprises administering, to a subject in need thereof, a pharmaceutically active amount of a amino acid sequences, compounds, proteins, polypeptides, fusion proteins, or multivalent or multispecific constructs of the invention, and/or of a pharmaceutical composition comprising the same. As will be clear to the skilled person, the diseases and disorders that can be prevented or treated by the use of amino acid sequences, compounds, proteins, polypeptides, fusion proteins, or multivalent or multispecific constructs described herein will generally be the same as the diseases and disorders that can be prevented or treated by the use of the therapeutic moiety that is present in the amino acid sequences, compounds, proteins, polypeptides, fusion proteins, or multivalent or multispecific constructs of the invention.

In the context of the present invention, the term "prevention and/or treatment" not only comprises preventing and/or treating a disease, but also generally comprises preventing the onset of a disease, slowing or reversing the progress of a disease, preventing or slowing the onset of one or more symptoms associated with a disease, reducing and/or alleviating one or more symptoms associated with a disease, reducing the severity and/or the duration of a disease and/or of any symptoms associated therewith and/or preventing a further increase in the severity of a disease and/or of any symptoms associated therewith, preventing, reducing or reversing any physiological damage caused by a disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

More specifically, the present invention relates to a method of treatment wherein the frequency of administering the amino acid sequence, compound, fusion protein or construct of the invention is at least 50% of the natural half-life of serum albumin in said mammal (i.e. in the case of man, of human serum albumin), preferably at least 60%, preferably at least 70%, more preferably at least 80%, and most preferably at least 90%.

Specific frequencies of administration to a mammal, which are within the scope of the present invention are at least 50%, 55%, 60%, 65%, 70%, 75%, 80%, 85%, 90%, 95%, or at least 100% of the natural half-life of serum albumin in said mammal as defined above.

In other words, specific frequencies of administration, which are within the scope of the present invention are every 4, 5, 6, 7, 8, 9, 10, 11, 12, 13, 14, 15, 16, 17, 18, or 19 days.

Without limitation, the frequencies of administration referred to above are in particular suited for maintaining a desired level of the amino acid sequence, compound, fusion protein or construct in the serum of the subject treated with the amino acid sequence, compound, fusion protein, or construct, optionally after administration of one or more (initial) doses that are intended to establish said desired serum level. As will be clear to the skilled person, the desired serum level may inter alia be dependent on the amino acid sequence, compound, fusion protein, or construct used and/or the disease to be treated. The clinician or physician will be able to select the desired serum level and to select the dose(s) and/or amount(s) to be administered to the subject to be treated in order to achieve and/or maintain the desired serum level in said subject, when the amino acid sequence, compound, fusion protein, or construct of the invention is administered at the frequencies mentioned herein.

In another embodiment, the invention relates to a method for immunotherapy, and in particular for passive immunotherapy, which method comprises administering, to a subject suffering from or at risk of the diseases and disorders mentioned herein, a pharmaceutically active amount of a fusion protein or construct of the invention, and/or of a pharmaceutical composition comprising the same.

The amino acid sequences, compounds, proteins, polypeptides, fusion proteins, or multivalent or multispecific constructs and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific amino acid sequence, compound, protein, polypeptide, fusion protein, or multivalent or multi specific construct of the invention to be used, the specific route of administration and pharmaceutical formulation or composition to be used, the age, gender, weight, diet, general condition of the patient, and similar factors well known to the clinician.

Generally, the treatment regimen will comprise the administration of one or more amino acid sequences, compounds, proteins, polypeptides, fusion proteins, or multivalent or multi specific constructs of the invention, or of one or more compositions comprising the same, in one or more pharmaceutically effective amounts or doses. The specific amount(s) or doses to administered can be determined by the clinician, again based on the factors cited above.

Generally, for the prevention and/or treatment of intended diseases and disorders (i.e. those diseases and disorders which are usually treated or prevented through the use of the therapeutic entity per se) and depending on the specific disease or disorder to be treated, the potency and/or the half-life of the specific amino acid sequences, compounds, proteins, polypeptides, fusion proteins, or multivalent or multispecific constructs to be used, the specific route of administration and the specific pharmaceutical formulation or composition used, the amino acid sequences, compounds, proteins, polypeptides, fusion proteins, or multivalent or multi specific constructs of the invention will generally be administered in an amount between 1 gram and 0.01 microgram per kg body weight per day, preferably between 0.1 gram and 0.1 microgram per kg body weight per day, such as about 1, 10, 100, 1000, or 2000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single amino acid sequence, compound, protein, polypeptide, fusion protein, or multivalent or multi specific construct of the invention will be used. It is however within the scope of the invention to use two or more amino acid sequences, compounds, proteins, polypeptides, fusion proteins, or multivalent or multispecific constructs of the invention in combination (e.g. as separate preparations or combined in a single preparation).

The amino acid sequences, compounds, proteins, polypeptides, fusion proteins, or multivalent or multi specific constructs of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the amino acid sequences, compounds, proteins, polypeptides, fusion proteins, or multivalent or multispecific constructs of the invention may be used in combination with other pharmaceutically active compounds or principles that are or can be used for the prevention and/or treatment of the diseases and disorders that can be prevented or treated with the amino acid sequences, compounds, proteins, polypeptides, fusion proteins, or multivalent or multi specific constructs of the invention, and as a result of which a synergistic effect may or may not be obtained.

The effectiveness of the treatment regimen used according to the invention may be determined and/or followed in any manner known per se for the disease or disorder involved, as will be clear to the clinician. The clinician will also be able, where appropriate and or a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

The invention will now be further illustrated by means of the following non-limiting Experimental Part and the non-limiting Figures, which show:

FIG. 1: alignment of the amino acid sequences of SEQ ID NO: 2 to 115 (invention) and 17D12 (SEQ ID NO:1, reference);

FIG. 2: graph showing the results of the phage-ELISA assay described in Example 2.

FIG. 3: graph showing the results of the solution binding competition assay described in Example 3.

FIGS. 4A and 4B: graphs showing the results of the alanine scanning experiment described in Example 3.

FIG. 5: Graph showing results of surface plasmon resonance analysis of the binding of the Nanobody® 2D3 (SEQ ID NO: 137), the Nanobody (fusion protein of 2D3 and 17D12 (SEQ ID NO: 138, reference), and the Nanobody (fusion protein of 2D3 and 56H5 (SEQ ID NO: 139, invention) described in Example 6 to human serum albumin (HSA). Coating of the chip (CM5) was performed by amine coupling using NHS/EDC for activation and ethanolamine for deactivation (Biacore amine coupling kit). Chip coated with ~7000 RU human serum albumin (Sigma, 99% pure) and 2460 RU irrelevant protein antigen. 2D3 and 2D3-17D12 was successively injected over the chip at concentrations of 1 µM and 5 µM. HBS-EP was used as flow buffer at a rate of 10 min-1. 20 µl of sample was injected for 120 s. Note that the fusion protein of 2D3 and 17D12 (SEQ ID NO: 138) is called "2D3-56G4" in FIG. 5.

FIG. 6: Pharmacokinetic profile of cynomolgus monkeys administered with the test item (Nanobody® construct 2D3-9GS-EXP56E4, SEQ ID NO: 142) and of cynomolgus monkeys administered with a negative control (Nanobody® 2D3, SEQ ID NO:137).

Figure 9:
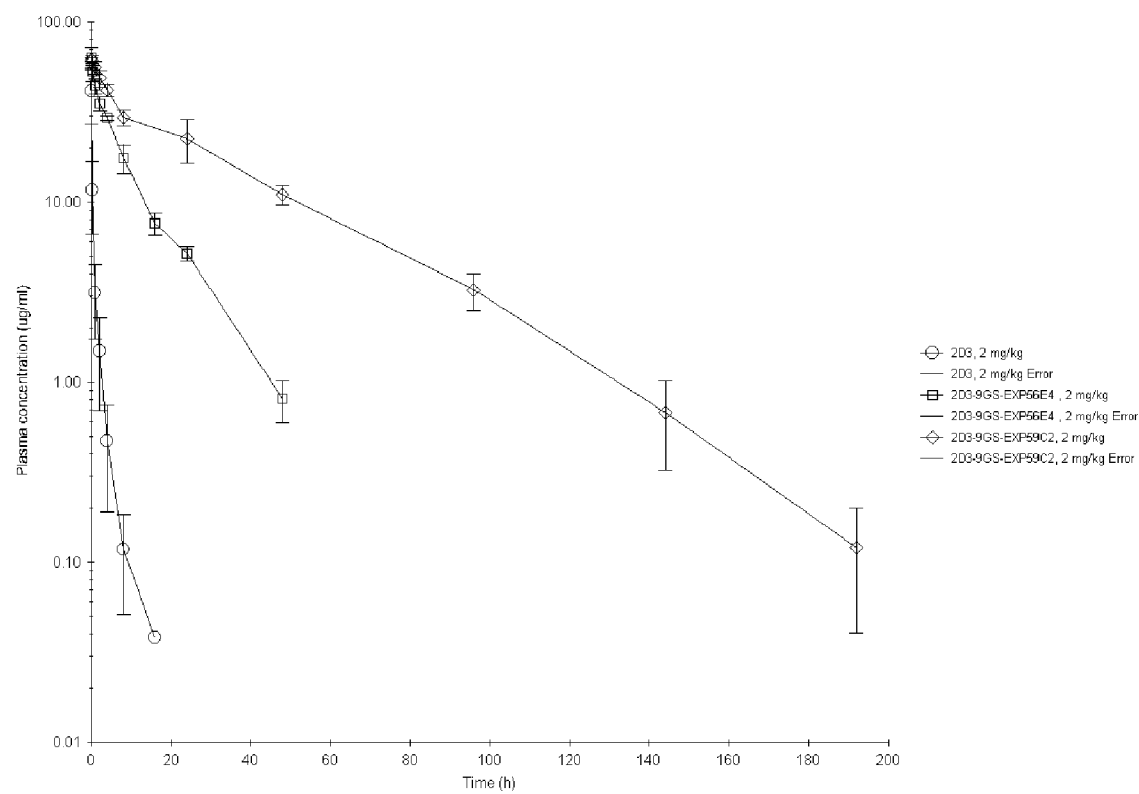

FIG. 9: Mean (+/−SD; n=3) serum concentration-time profiles of 2D3-9GS-EXP56E4, 2D3-9GS-EXP59C2, and 2D3 following i.v. bolus administration at 2 mg/kg 2D3-9GS-EXP56E4, 2D3-9GS-EXP59C2 or 2D3, respectively in the male Cynomolgus monkey.

Figure 10:
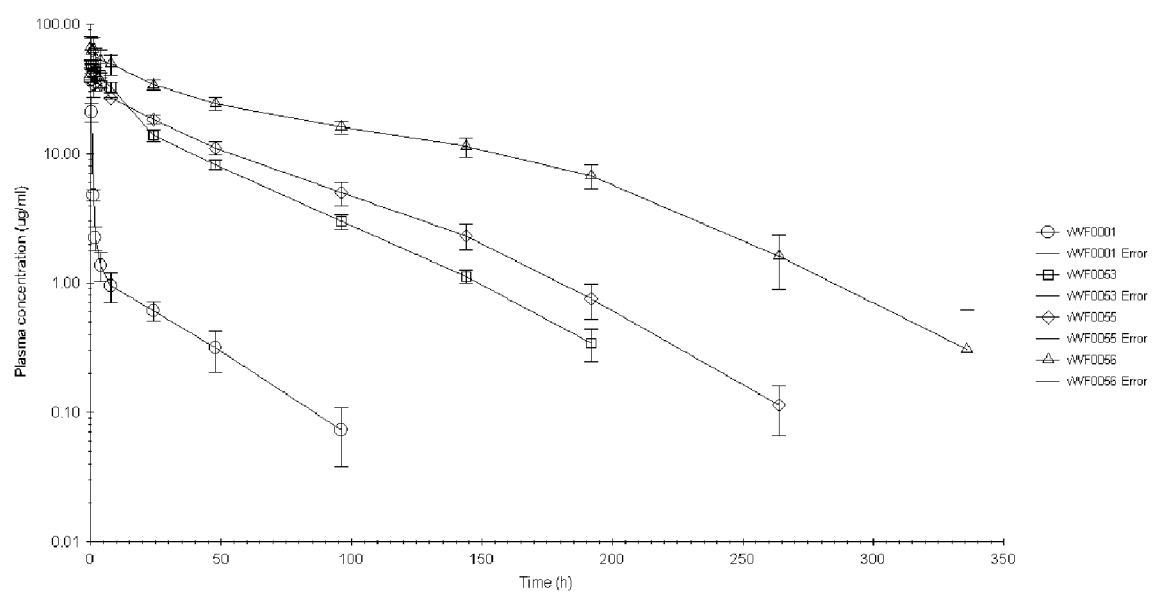

FIG. 10: Mean (+/−SD; n=3) plasma concentration-time profiles of vWF-0053, vWF-0055, vWF-0056, and vWF0001 following i.v. bolus administration at 2 mg/kg vWF-0053, vWF-0055, vWF-0056 (test items), and vWF0001 (control), respectively in the male Cynomolgus monkey.

Figure 11:
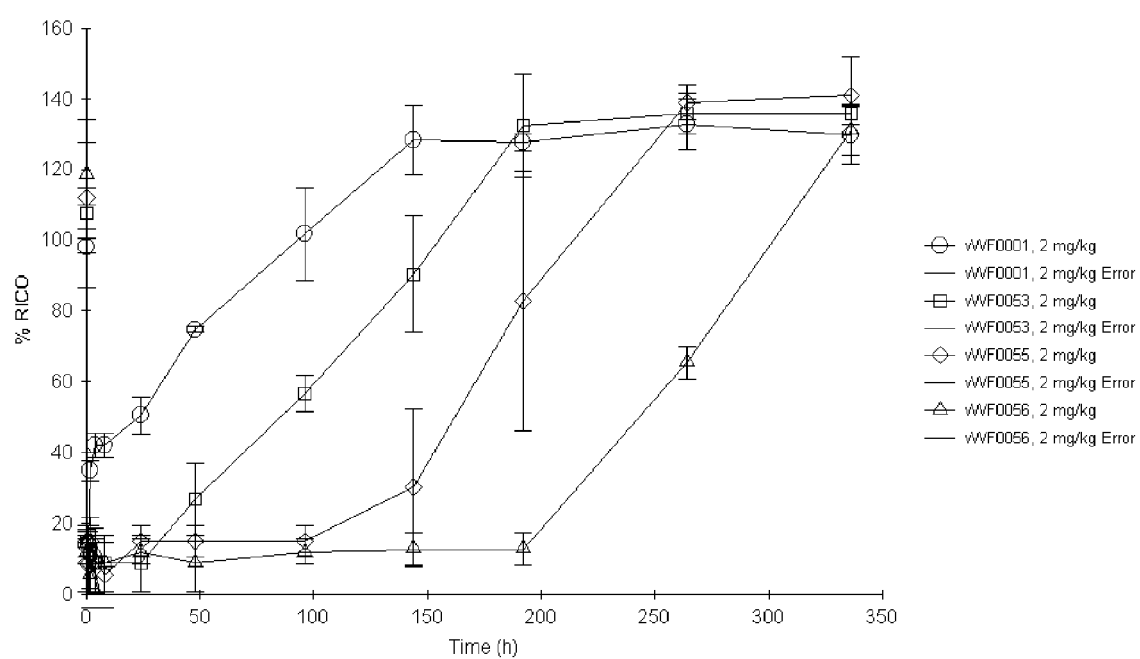

FIG. 11: Mean (+/−SD; n=3) % RICO-time profiles following i.v. bolus administration at 2 mg/kg vWF-0053, vWF-0055, vWF-0056 (test items), and vWF0001 (control), respectively in the male Cynomolgus monkey.

Figure 12:
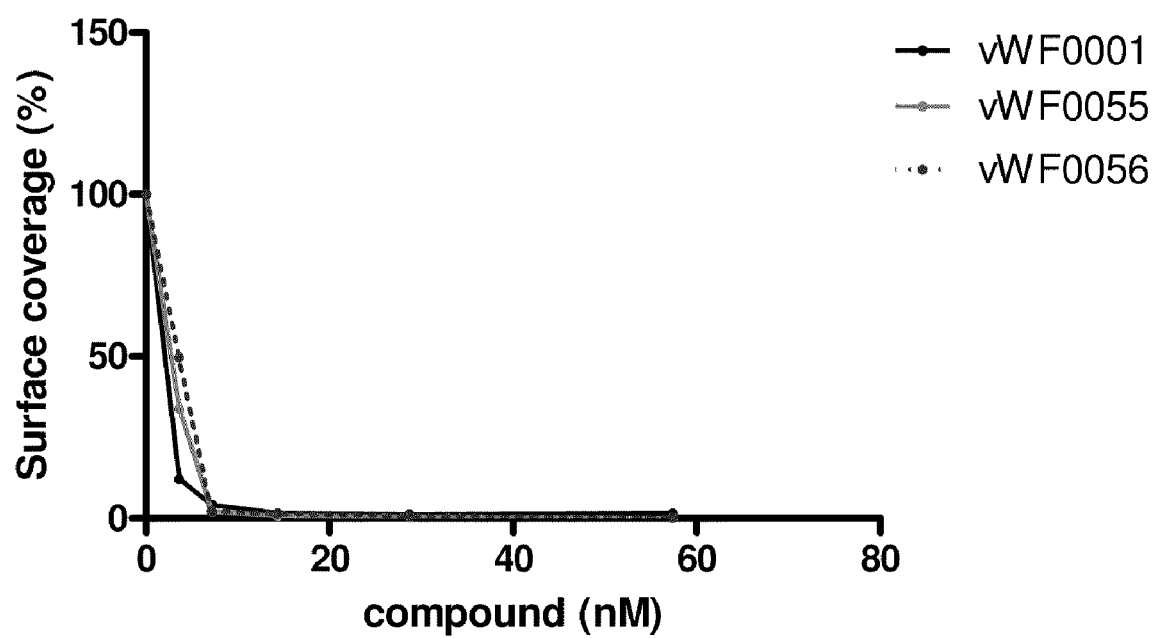

FIG. 12: diagram showing the results of the perfusion experiments performed in Example 15 with the anti vWF compounds of the invention vWF-0053, vWF-0055 and vWF-0056.

Figure 13:
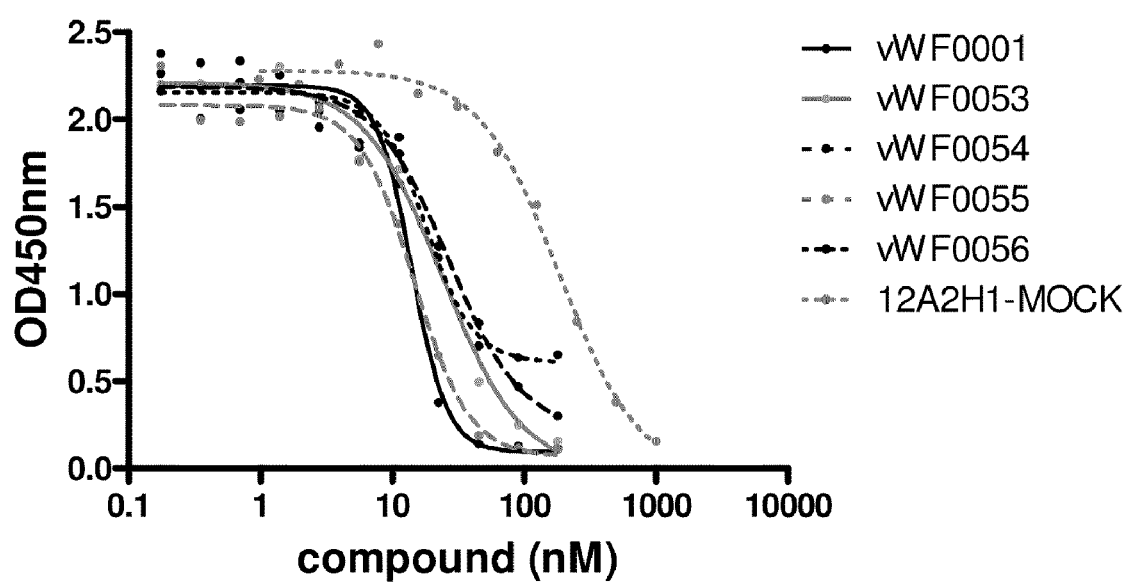

FIG. 13: diagram showing the results obtained in the ELISA for the ristocetin-induced binding to vWF performed in Example 15 with the anti vWF compounds of the invention vWF-0053, vWF-0055 and vWF-0056.

EXPERIMENTAL PART

Example 1

Examples of Amino Acid Sequences of the Invention

Some non-limiting examples of amino acid sequences of the invention are given as SEQ ID NO's 2 to 115 and 147 to 157 in Table II below. An alignment of the sequences of SEQ ID NO's 2 to 115 is given in FIG. 1.

Some preferred amino acid sequences of the invention are marked in bold typeface underlined (see for example SEQ ID NO:12).

Of these, the amino acid sequences PMP56G11 (SEQ ID NO:68); PMP56E4 (SEQ ID NO: 14); PMP54H4 (SEQ ID NO: 106); PMP54H5 (SEQ ID NO: 33); PMP56H1 (SEQ ID NO: 31); PMP56E2 (SEQ ID NO:47); PMP56G3 (SEQ ID NO: 35); PMP54G1 (SEQ ID NO:38); PMP56F1 (SEQ ID NO: 30); PMP54H2 (SEQ ID NO: 40) PMP56H9 (SEQ ID NO: 100); PMP56F2 (SEQ ID NO: 51); PMP26A3 (SEQ ID NO:26) and 01B3 (SEQ ID NO:115) are particularly preferred representative examples of amino acid sequences of the invention.

The sequences of SEQ ID NO's: 147 to 157 are some preferred but non-limiting examples of affinity matured variants (see Example 9 below) of one of the above sequences (in this case, of PMP56E4—SEQ ID NO:14) and thus are also some particularly preferred amino acid sequences of the invention. Of these, the sequences 59F2 (SEQ ID NO: 149); 59H12 (SEQ ID NO: 155) and 59C2 (SEQ ID NO: 156) are especially preferred.

The amino acid sequence called "17D12" (SEQ ID NO:1) is not an amino acid sequence of the invention, but is a comparative amino acid sequence described in the non-prepublished International application PCT/EP2007/063348.

All sequences of the invention below (SEQ ID NOs: 2 to 115 and 147 to 157) are expected to be cross-reactive for both human serum albumin and cyno serum albumin. The sequences SEQ ID NOs: 2 to 60 and 115 were tested for binding to human serum albumin, and the sequences of SEQ ID NOs: 61 to 114 were tested for binding to serum albumin from cynomolgus monkey. The sequences of SEQ ID NOs: 2-60 and 115 all bind better (as determined using the assays described in Examples 2 and/or 3) to human serum albumin than the sequence of SEQ ID NO:1 (the same is expected for the sequences of SEQ ID NOs: 61 to 114). Data obtained for some of the sequences of SEQ ID NO's: 147 to 157 is presented in Examples 9 ff.

TABLE II

Examples of amino acid sequences of the invention (SEQ ID NOs: 2-115 and 147-157).

| CLONE DESIGNATION | SEQ ID NO: | AMINO ACID SEQUENCE |
|---|---|---|
| 17D12 | SEQ ID NO: 1 | AASYSDYDVFGGGTDFGP |
| PMP56B2 | SEQ ID NO: 2 | AARYFDYDVFGGGTPAGD |
| PMP54D2 | SEQ ID NO: 3 | AARYFDYDVFGGGTDLGD |
| PMP56E6 | SEQ ID NO: 4 | AARYYDYDVFGGGTPLGG |
| PMP56F5 | SEQ ID NO: 5 | AARYYDYDVFGGGTPLGG |
| PMP56G6 | SEQ ID NO: 6 | AARYYDYDVFGGGTPLGG |
| PMP56E3 | SEQ ID NO: 7 | AARYYDYDVFGGGTPLGA |
| PMP56C3 | SEQ ID NO: 8 | AARYYDYDVFGGGTPLGA |
| PMP56E5 | SEQ ID NO: 9 | AARYYDYDVFGGGTPLGA |
| PMP54B2 | SEQ ID NO: 10 | AARYYDYDVFGGGTVVGE |
| PMP54C1 | SEQ ID NO: 11 | AARYYDYDVFGGGTRSGE |
| PMP56A6 | SEQ ID NO: 12 | AARYYDYDVFGGGTAGGQ |
| PMP56B4 | SEQ ID NO: 13 | AARYWDYDVFGGGTPVGG |
| PMP56E4 | SEQ ID NO: 14 | AARYWDYDVFGGGTPVGG |
| PMP56B1 | SEQ ID NO: 15 | AARYWDYDVFGGGTPQGE |
| PMP56C2 | SEQ ID NO: 16 | AARYWDYDVFGGGTPQGE |
| PMP56G2 | SEQ ID NO: 17 | AARYWDYDVFGGGTDPGG |
| PMP54D3 | SEQ ID NO: 18 | AARYLDYDVFGGGTQLGS |
| PMP54F3 | SEQ ID NO: 19 | AARYLDYDVFGGGTDVGS |
| PMP54C3 | SEQ ID NO: 20 | AARYLDYDVFGGGTPIGE |
| PMP54C2 | SEQ ID NO: 21 | AARYPDYDVFGGGTPVGG |
| PMP56C6 | SEQ ID NO: 22 | AARYPDYDVFGGGTPSGG |
| PMP54E2 | SEQ ID NO: 23 | AALYRDYDVFAGGTPGGG |
| PMP56B5 | SEQ ID NO: 24 | AALYRDYDVFGGGTPVGG |
| PMP56F6 | SEQ ID NO: 25 | AALYRDYDVFGGGTPVGG |
| PMP56A3 | SEQ ID NO: 26 | AALYDDYDVFGGGTPVGG |
| PMP56D6 | SEQ ID NO: 27 | AALYDDYDVFGGGTPVGG |
| PMP56B3 | SEQ ID NO: 28 | AAVYDDYDVFGGGTPVGG |
| PMP56C5 | SEQ ID NO: 29 | AAMYDYDVFGGGTPTGA |
| PMP56F1 | SEQ ID NO: 30 | AAWYTDYDVFGGGTPQGG |
| PMP56H1 | SEQ ID NO: 31 | AAWYRDYDVFGGGTPLGA |
| PMP54B1 | SEQ ID NO: 32 | AAWYRDYDVFGGGTDEGS |
| PMP56H5 | SEQ ID NO: 33 | AAFYDDYDVFGGGTPAGG |
| PMP56H3 | SEQ ID NO: 34 | AAFYWDYDVFGGGTDPGA |
| PMP56G3 | SEQ ID NO: 35 | AAFYWDYDVFGGGTDPGA |
| PMP56G1 | SEQ ID NO: 36 | AAYYFDYDVFGGGTPEGT |
| PMP56C1 | SEQ ID NO: 37 | AAYYFDYDVFGGGTPEGT |
| PMP54G1 | SEQ ID NO: 38 | AATYFDYDVFGGGTAVGS |
| PMP56G5 | SEQ ID NO: 39 | AAAYLDYDVFGGGTPVGG |
| PMP54H2 | SEQ ID NO: 40 | AAAYWDYDVFGGGTSAGT |
| PMP56B6 | SEQ ID NO: 41 | AAVYWDYDVFGGGTSLGD |
| PMP56H6 | SEQ ID NO: 42 | AAWYFDYDVFGGGTADGE |
| PMP56F3 | SEQ ID NO: 43 | AAWYFDYDVFGGGTADGE |
| PMP54G3 | SEQ ID NO: 44 | AAYYYDYDVFGGGTPGGE |
| PMP56A1 | SEQ ID NO: 45 | AADYYDYDVFGGGTSVGE |
| PMP56E1 | SEQ ID NO: 46 | AAYYYDYDVFGGGTPGGE |
| PMP56E2 | SEQ ID NO: 47 | AAYYYDYDVFGGGTPGGE |
| PMP56A5 | SEQ ID NO: 48 | AAYYRDYDVFGGGTPVGE |
| PMP54B3 | SEQ ID NO: 49 | AALYRDYDVFGGGTQVGE |
| PMP56D4 | SEQ ID NO: 50 | AALYKDYDVFGGGTPGGE |
| PMP56F2 | SEQ ID NO: 51 | AAPYRDYDVFGGGTPRGE |
| PMP56A2 | SEQ ID NO: 52 | AAPYHDYDVFGGGTPVGE |
| PMP54F2 | SEQ ID NO: 53 | AALYGDYDVFGGGTPLGE |
| PMP54H1 | SEQ ID NO: 54 | AASYLDYDVFGGGTPFGE |
| PMP54E1 | SEQ ID NO: 55 | AAFYRDYDVFGGGTGSGN |
| PMP54G2 | SEQ ID NO: 56 | AAIYRDYDVFGGGTPLGQ |
| PMP56D5 | SEQ ID NO: 57 | AATYYDYDVFGGGTPLGQ |
| PMP54H3 | SEQ ID NO: 58 | AASYRDYDVFGGGTPRGW |
| PMP54E3 | SEQ ID NO: 59 | AATYLDYDVFGGGTPDGR |
| PMP56A4 | SEQ ID NO: 60 | AAFYMDYDVFGGGTPRGQ |
| PMP54G5 | SEQ ID NO: 61 | AAPYFDYDVFGGGTARGG |
| PMP54F5 | SEQ ID NO: 62 | AAPYFDYDVFGGGTEVGG |
| PMP56A9 | SEQ ID NO: 63 | AAPYFDYDVFGGGTPMGG |

TABLE II-continued

Examples of amino acid sequences of the invention (SEQ ID NOs: 2-115 and 147-157).

| CLONE DESIGNATION | SEQ ID NO: | AMINO ACID SEQUENCE |
|---|---|---|
| PMP56B9 | SEQ ID NO: 64 | AARYYDYDVFGGGTPGGV |
| PMP56D7 | SEQ ID NO: 65 | AARYYDYDVFGGGTPGGV |
| PMP56H10 | SEQ ID NO: 66 | AARYYDYDVFGGGTSRGG |
| PMP56G10 | SEQ ID NO: 67 | VARYYDYDVFGGGTWSGD |
| PMP56G11 | SEQ ID NO: 68 | AVRYYDYDVFGGGTSVGG |
| PMP54G6 | SEQ ID NO: 69 | AALYYDYDVFGGGTPEGI |
| PMP56A10 | SEQ ID NO: 70 | AALYYDYDVFGGGTAAGS |
| PMP56A7 | SEQ ID NO: 71 | AALYYDYDVFGGGTPRGG |
| PMP56C7 | SEQ ID NO: 72 | AAYYYDYDVFGGGTALGG |
| PMP56B11 | SEQ ID NO: 73 | AADYYDYDVFGGGTVFGS |
| PMP56D8 | SEQ ID NO: 74 | AATYYDYDVFGGGTSLGN |
| PMP56G7 | SEQ ID NO: 75 | AALYYDYDVFGGGTYKGS |
| PMP54D6 | SEQ ID NO: 76 | AATYYDYDVFGGGTDGGS |
| PMP56C10 | SEQ ID NO: 77 | AARYWDYDVFGGGTPEGV |
| PMP54B5 | SEQ ID NO: 78 | AARYWDYDVFGGGTAQGE |
| PMP54E6 | SEQ ID NO: 79 | AARYWDYDVFGGGTPEGV |
| PMP56A8 | SEQ ID NO: 80 | AARYWDYDVFGGGTPEGV |
| PMP56B7 | SEQ ID NO: 81 | AARYWDYDVFGGGTPEGV |
| PMP56C9 | SEQ ID NO: 82 | AARYWDYDVFGGGTPEGI |
| PMP56D12 | SEQ ID NO: 83 | AARYWDYDVFGGGTPEGV |
| PMP56E8 | SEQ ID NO: 84 | AARYWDYDVFGGGTPEGV |
| PMP56F10 | SEQ ID NO: 85 | AGRYWDYDVFGGGTAQGA |
| PMP56G9 | SEQ ID NO: 86 | AGRYWDYDVFGGGTAQGA |
| PMP56E11 | SEQ ID NO: 87 | VAKYWDYDVFGGGTDSGG |
| PMP56F7 | SEQ ID NO: 88 | AASYWDYDVFGGGTPVGD |
| PMP56B12 | SEQ ID NO: 89 | AAQYWDYDVFGGGTPKGE |
| PMP54C6 | SEQ ID NO: 90 | AALYRDYDVFGGGTPVGG |
| PMP56A11 | SEQ ID NO: 91 | AALYRDYDVFGGGTSAGV |
| PMP56B10 | SEQ ID NO: 92 | AALYRDYDVFGGGTPSGV |
| PMP56D11 | SEQ ID NO: 93 | AALYRDYDVFGGGTPKGE |
| PMP56D9 | SEQ ID NO: 94 | AALYRDYDVFGGGTPKGE |
| PMP56C8 | SEQ ID NO: 95 | AALYRDYDVFGGGTPSGV |
| PMP56E9 | SEQ ID NO: 96 | AALYRDYDVFGGGTPSGV |
| PMP56F11 | SEQ ID NO: 97 | AALYRDYDVFGGGTPRGG |
| PMP56F9 | SEQ ID NO: 98 | AALYRDYDVFGGGTPKGE |
| PMP56H7 | SEQ ID NO: 99 | AALYRDYDVFGGGTPVGG |
| PMP56H9 | SEQ ID NO: 100 | AALYRDYDVFGGGTPRGS |
| PMP56H11 | SEQ ID NO: 101 | AAFYRDYDVFGGGTPKGG |
| PMP56A12 | SEQ ID NO: 102 | AAFYRDYDVFGGGTPKGG |
| PMP54H5 | SEQ ID NO: 103 | AAFYRDYDVFGGGTDMGN |
| PMP54E5 | SEQ ID NO: 104 | AAWYRDYDVFGGGTPLGA |
| PMP56D10 | SEQ ID NO: 105 | AAWYRDYDVFGGGTPLGA |
| PMP54H4 | SEQ ID NO: 106 | AARYPDYDVFGGGTSMGQ |
| PMP54B6 | SEQ ID NO: 107 | AAMYDYDVFGGGTPSGA |
| PMP54C5 | SEQ ID NO: 108 | AAYYLDYDVFGGGTPGGG |
| PMP54F6 | SEQ ID NO: 109 | AAFYDYDVFGGGTPAGG |
| PMP54H6 | SEQ ID NO: 110 | AASYLDYDVFGGGTPGGG |
| PMP56B8 | SEQ ID NO: 111 | AAPYLDYDVFGGGTPEGS |
| PMP56C12 | SEQ ID NO: 112 | AALYSDYDVFGGGTPPGV |
| PMP56E10 | SEQ ID NO: 113 | AAPYPDYDVFGGGTPQGS |
| PMP56E12 | SEQ ID NO: 114 | AAMYDYDVFGGGTPSGA |
| 01B3 | SEQ ID NO: 115 | AALYDDYDVFGGGTPAGG |
| 59A5 | SEQ ID NO: 147 | AARWWDYDVFGGGTPVGG |
| 59C8 | SEQ ID NO: 148 | AARYWDWDVFGGGTPVGG |
| 59F2 | SEQ ID NO: 149 | AARYWDFDVFGGGTPVGG |
| 59B3 | SEQ ID NO: 150 | AARYWDFDAFGGGTPVGG |
| 59B2 | SEQ ID NO: 151 | AARFWDYDVFGGGTPVGG |
| 60 E6 | SEQ ID NO: 152 | AARYWDYDVFGGGTPVDG |
| 60F1 | SEQ ID NO: 153 | AARYWDYDVFGGGSQVGG |
| 60G5 | SEQ ID NO: 154 | AARYWDYDVFGGGSPVGG |
| 59H12 | SEQ ID NO: 155 | AARSWDFDVFGGGTPVGG |
| 59C2 | SEQ ID NO: 156 | AARDWDFDVFGGGTPVGG |
| 59H10 | SEQ ID NO: 157 | AARYWDFDVFGGGSPVGG |

Example 2

Phage ELISA 5-fold serial dilutions of phage clones (starting from ~5×10[11] phage) were added to 96-well Nunc Maxisorp plates coated with human serum albumin (2 µg/ml in PBS, overnight at 4° C.; plates were blocked with Superblock T20 (Pierce) for 1 h at room temperature). The microtiter plate was washed with wash buffer (PBS, 0.05% Tween 20) and bound phages were detected with anti-M13 and goat-anti mouse IRDye conjugate (610-130-121, Rockland). The amount of IRDye bound was measured on Odyssey (LI-COR Biosciences). The dilution of phage was plotted against measured near-infrared fluorescence intensity (FIG. 2). Clones 56 E2 and 56 F2 show stronger binding to HSA compared to the amino acid sequence

```
AASYSDYDVFGGGTDFGP.            (SEQ ID NO: 1)
```

Example 3

Solution Binding Competition ELISA

A competition ELISA was performed to determine the relative binding affinity for the selected phage clones. 96-well Nunc Maxisorp plates were coated with 2 μg/ml HSA in coating buffer at 4° C. Plates were blocked with SuperblockT20 (Pierce) for 1 h at room temperature. The microtiter plates were washed with wash buffer (PBS, 0.05% Tween 20).

Sixty μl of a 12.5 fold dilution of a 1012/ml phage stock was incubated with 60 μl of various concentrations of HSA (1.6-10000 nM final concentration) for 30 minutes at room temperature in a tissue culture microtiter plate. Unbound phage was captured by transferring 100 μl of the well mixture to the HSA coated Maxisorp plate and incubating at room temperature for 30 minutes. The plate with captured phage was washed with PBS-0.05% Tween 20 at least five times. Bound phages were detected with anti-M13 and goat-anti mouse IRDye conjugate. The amount of IRDye bound was measured on Odyssey (LI-COR Biosciences). The % of phage binding was calculated by the following equation: Phage binding %=fluorescence signal of well with competitor/fluorescence signal of well with no competitor*100 (FIG. 3). The $IC_{50}$, the concentration of HSA in solution that inhibits 50% of the phage binding, represents the affinity.

When this assay is used to compare binding of an amino acid sequence of the invention to the amino acid sequence AASYSDYDVFGGGTDFGP (SEQ ID NO:1), the amino acid sequences of the invention bind "better" to the relevant serum albumin (e.g. to human serum albumin).

Example 4

Alanine Scanning of 17D12

Alanine scanning of the peptide 17D12 (SEQ ID NO:1) peptide was performed to identify amino acids within the peptide sequence amenable for mutation to improve binding to HSA. The amino acid residues of the 17D12-peptide were numbered from 1 to 18, as follows:

```
                                          (SEQ ID NO: 1)
 1 2 3 4 5 6 7 8 9 10 11 12 13 14 15 16 17 18
 A A S Y S D Y D V F  G  G  G  T  D  F  G  P
```

Figure 4A:
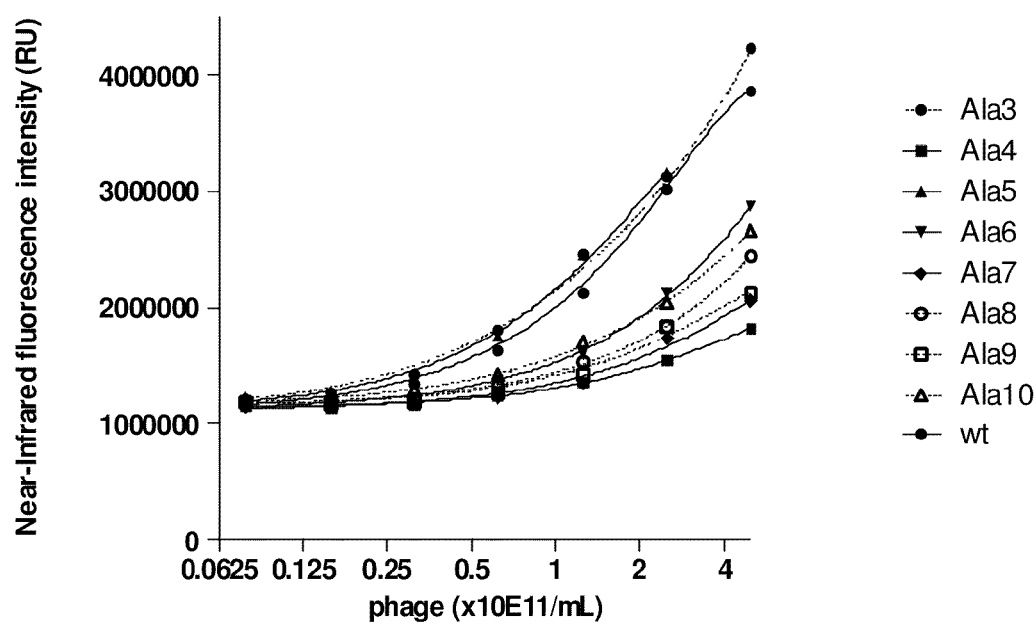
Figure 4B:
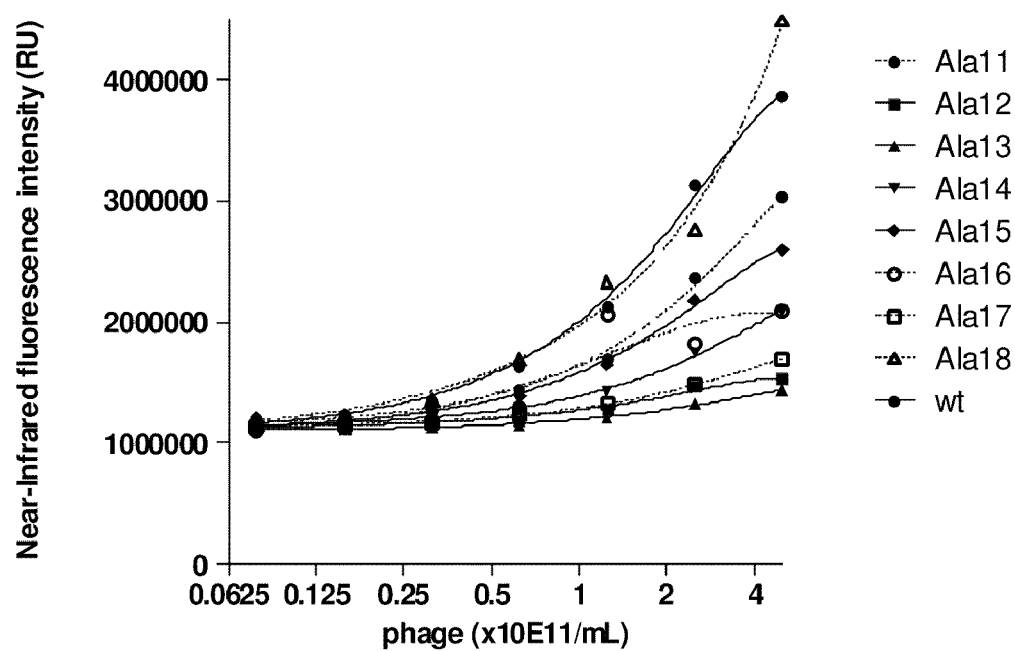

Individual amino acids which were not already alanine in the original sequence were mutated to alanine and effects on binding to HSA of each variant peptide were investigated. The 16 variant peptide constructs (with alanine substitutions at positions 3-18 in SEQ ID NO:1) were generated as N-terminal fusions with M13 bacteriophage geneIII and phage were produced. Variant peptides expressed on phage were assayed for binding to HSA. Binding was compared to binding of the wild-type peptide displayed on phage. A Maxisorp microtiter plate was coated with 2 μg/mL HSA and blocked with SuperBlock T20. Serial 2-fold dilutions of variant or wild-type phage in PBS+0.05% Tween-20+10% Superblock T20 (Pierce) were incubated for 1.5 h at room temperature. Bound phage were detected using anti-M13 (27-9420-01, GE Healthcare) and goat anti-mouse IRDye700 (610-130-121, Rockland) antibodies and near-infrared fluorescence intensity was measured on Odyssey (LI-COR Biosciences). For clarity reasons, the data are represented in two graphs (FIGS. 4A and 4B). Amino acid substitutions in 17D12 that did not result in a significant decrease in HSA binding were selected for randomization (underlined in the sequence above).

For affinity maturation of 17D12, 6 residues were chosen for randomization using an nnk codon (underlined in sequence), based on alanine scanning data and the functionality of the residues.

Example 5

Solution Binding Competition ELISA of Clones 01G7, 01B3 and 01C7

The 3 clones listed in Table III below were tested in a solution binding competition ELISA, as follows:

A competition ELISA was performed to determine the relative binding affinity for the selected phage clones. 96-well Nunc Maxisorp plates were coated with 2 μg/ml HSA in coating buffer at 4° C. Plates were blocked with SuperblockT20 (Pierce) for 1 h at room temperature. The microtiter plates were washed with wash buffer (PBS, 0.05% Tween 20).

45 μl phage stock was pre-incubated with 65 μl HSA solution 1.67 μM (1 μM final) or 65 μl 16.9% Superblock T20 in PBS/0.05% Tween 20 for 30 minutes at room temperature in a tissue culture microtiter plate. Unbound phage was captured by transferring 100 μl of the well mixture to the HSA coated Maxisorp plate and incubating at room temperature for 30 minutes. The plate with captured phage was washed with PBS-0.05% Tween 20 five times. Bound phages were detected with anti-M13 and goat-anti mouse IRDye conjugate. The amount of IRDye bound was measured on Odyssey (LI-COR Biosciences). The ratio of phage binding was calculated by the following equation: fluorescence signal of well with competitor/fluorescence signal of well with no competitor (Table III).

TABLE III

| Solution binding competition assay | |
|---|---|
| Clone | Ratio 1 μM/0 μM HSA |
| 01G7 (=56H5; SEQ ID NO: 33) | 0.43 |
| 01B3 (SEQ ID NO: 115) | 0.42 |
| 01C7 (=56A3; SEQ ID NO: 26) | 0.47 |

Example 6

Construction of a Nanobody-Expedite Fusion Protein and Analysis of Binding to HSA HSA-binding peptides 17D12 (reference) and 56H5 (SEQ ID NO:33; invention) were each genetically fused at the C-terminus of the Nanobody 2D3:

```
                                         [SEQ ID NO: 137]
EVQLVESGGSLVQPGGSLRLSCAASGFTFDDYAMSWVRQVPGKGLEWVSS

INWSGTHTDYADSVKGRFTISRNNANNTLYLQMNSLKSEDTAVYYCAKNW

RDAGTTWFEKSGSAGQGTQVTVSS
``` via the following linker sequence (that comprises a Gly4Ser-Gly3Ser linker and a flanking amino acid sequence GSA]

GGGGSGGGSA          [SEQ ID NO: 140]

and with the following C-terminal tag:

AAAEQKLI SEEDLNGAAH HHHHH.    [SEQ ID NO: 141]

The resulting fusion proteins had the following sequences:

2D3-17D12 fusion protein:
                                    [SEQ ID NO: 138]
EVQLVESGGSLVQPGGSLRLSCAASGFTFDDYAMSWVRQVPGKGLEWVSS
INWSGTHTDYADSVKGRFTISRNNANNTLYLQMNSLKSEDTAVYYCAKNW
RDAGTTWFEKSGSAGQGTQVTVSSGGGGSGGGSAAASYSDYDVFGGGTDF
GPAAAEQKLISEEDLNGAAHHHHHH.

2D3-56H5 fusion protein:
                                    [SEQ ID NO: 139]
EVQLVESGGSLVQPGGSLRLSCAASGFTFDDYAMSWVRQVPGKGLEWVSS
INWSGTHTDYADSVKGRFTISRNNANNTLYLQMNSLKSEDTAVYYCAKNW
RDAGTTWFEKSGSAGQGTQVTVSSGGGGSGGGSAAAFYDDYDVFGGGTPA
GGAAAEQKLISEEDLNGAAHHHHHH.

The binding of the resulting 2D3-17D12 and 2D3-56H5 fusion proteins to human serum albumin was determined using surface plasmon resonance analysis. For this purpose, the fusion proteins were expressed in *E. coli* TG1 cells. The fusion proteins were purified by IMAC/SEC and binding to HSA was assessed in BIAcore™ 3000, by injecting 1 µM and 5 µM of the 2D3-17D12 and 2D3-56H5 fusion proteins on a CM5 chip coated with ~7000 RU human serum albumin (Sigma, 99% pure) and 2460 RU an irrelevant protein antigen (reference). Coating of the chip (CM5) was performed by amine coupling using NHS/EDC for activation and ethanolamine for deactivation (Biacore amine coupling kit). HBS-EP was used as flow buffer at a rate of 10 min-1. 20 µl of sample was injected for 120 s. The 2D3 Nanobody was injected as control.

Figure 5:
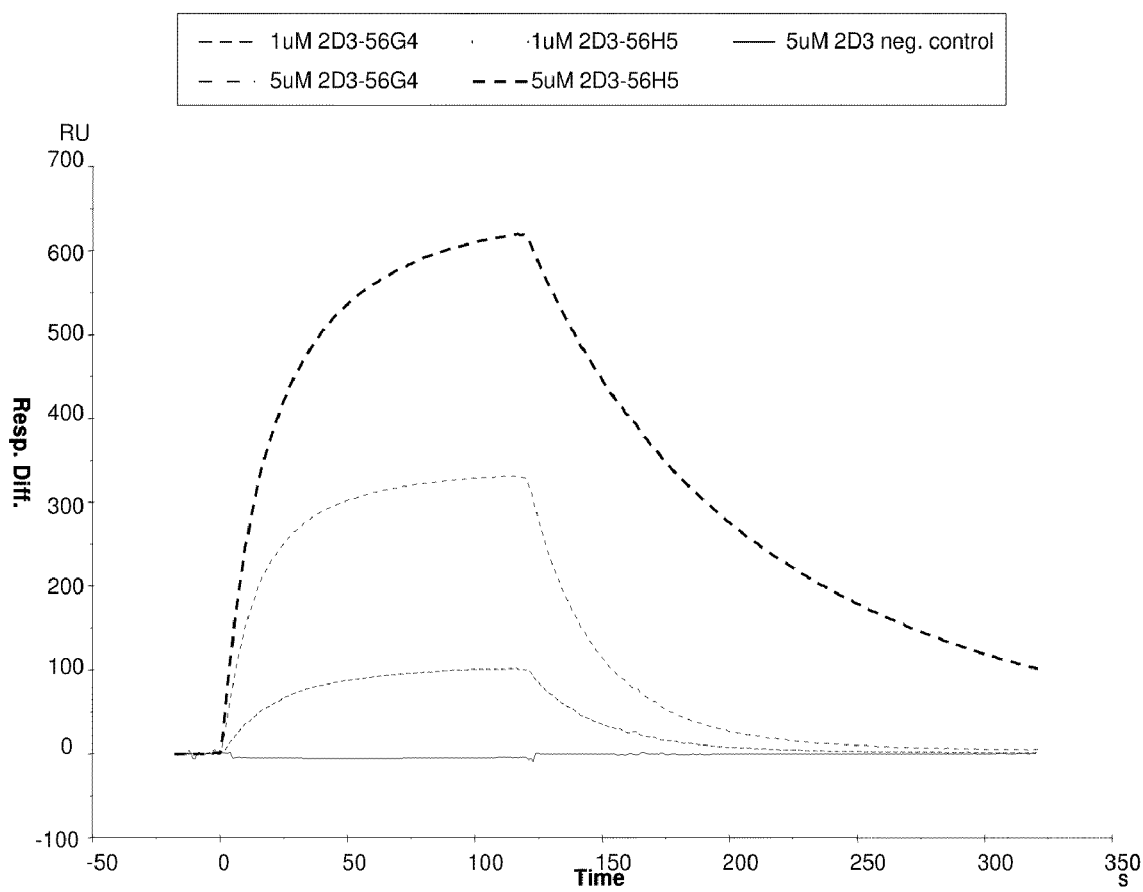

FIG. 5 shows improved binding of the 2D3-56H5 fusion protein to HSA compared to the 2D3-17D12 fusion protein (which is called 2D3-56G4 in FIG. 5), whereas, as expected, 2D3 does not bind at identical concentrations tested. Calculated affinity of the 2D3-56H5 fusion protein for HSA is ~1.2 µM (ka (1/Ms)=7.57E+03 and kd (1/s)=9.3E−03). As a control, 5 µM of the fusion protein 2D3-56H5 was injected on CM5 chip coated with high density of irrelevant protein (2400RU), but no specific binding was detected.

Example 7

Pharmacokinetic Profile in Male Cynomolgus Monkeys

A Nanobody construct was prepared as a fusion of the peptide 56E4 (SEQ ID NO: 14, also referred to herein as PMP56E4) and the Nanobody 2D3 (SEQ ID NO:137), via a Gly4Ser-Gly3Ser ("9GS") linker sequence.

The sequence of the Nanobody construct (referred to as 2D3-9GS-EXP56E4) used was:

[SEQ ID NO: 142]
EVQLVESGGSLVQPGGSLRLSCAASGFTFDDYAMSWVRQVPGKGLEWVSS
INWSGTHTDYADSVKGRFTISRNNANNTLYLQMNSLKSEDTAVYYCAKNW
RDAGTTWFEKSGSAGQGTQVTVSSGGGGSGGGSRYWDYDVFGGGTPVGG.

As a negative control, the Nanobody 2D3 was used (without the 56E4 peptide).

The pharmacokinetic profile of this 2D3-9GS-EXP56E4 Nanobody construct ("construct" or "test item" hereafter) was analysed in male cynomolgus monkeys of approximately 3 to 4 years old and was compared to the 2D3 control ("control" or "negative control" hereafter). The construct and the control were each injected in three monkeys. Both the construct and the control were administered at a dose of 2 mg/kg via intravenous infusion. Blood samples were taken at pre-dose, 5 min, 20 min, 1 h, 2 h, 4 h, 8 h, and 16 h after administration and at test days 2, 3, 5, 7, 9, 12, 15, 18, 21, 24, 27, 30, 33, 36, 39, 42, 45, 48, 51, 54, and 57 after the start of the infusion. In order to obtain at least 0.25 mL serum per animal per sampling time, a sufficient volume of whole blood was withdrawn per sampling time and the serum was isolated after 1 h of incubation at 37° C. The serum samples were stored at −80° C.

Serum samples were tested for serum levels of construct and the control, respectively, using the following ELISA assay.

96-well microtiter plates (Maxisorp, Nunc, Wiesbaden, Germany) were coated for 1 hour at 37° C. with Recombinant Human ErbB2/Fc Chimera, C F (R&D Systems, Minneapolis) in PBS at 3 µg/mL for the negative control and 4.5 µg/mL for the test item. Wells were aspirated and blocked for 30 minutes at room temperature (RT) with SuperBlock®T20 PBS (Pierce, Rockford, Ill.). After this blocking step, wells were washed with PBS-0.05% Tween20.

Preparations for the standards, QC samples and dilutions of the test samples were performed in a non-coated (polypropylene) plate.

Standard curve and QC-samples: Solutions at the required concentrations were prepared in PBS 0.1% casein and spiked into 100% monkey serum. To prepare standards and QC samples, a 1/10 dilution of the pure monkey serum dilutions was made in PBS-0.1% casein.

Test samples: Dilution factors for the test samples were estimated, and varied from 1/10 to 1/500. Samples were diluted 1/10 in PBS 0.1% casein in a first step, and if needed, further dilution was done in PBS 0.1% casein containing 10% monkey serum. These sample dilutions were further serially diluted 1/5 in PBS 0.1% casein with 10% monkey serum over 2 wells.

Standards, QC samples and the 1/5 dilutions of the test samples were transferred onto the coated plate and incubated for 1 hour at RT. Afterwards the plates were washed and rabbit polyclonal anti-VHH K1, purified against protein A and Her2/Fc depleted, was added at 1 µg/mL in PBS 0.1% casein, and incubated for 1 hour at RT. After washing a 1/2000 dilution in PBS 0.1% casein of horse radish peroxidase labelled goat anti-rabbit (Dakocytomation, Denmark) was added to the plate and incubated for 30 minutes at RT. This enzyme catalyzes a chemical reaction with the substrate sTMB (3,3',5,5'-tetramethylbenzidine, SDT reagents, Brussels, Belgium), which results in a colorimetric change. After stopping this reaction after 15 minutes using HCl (1N), the intensity of the colour was measured by a spectrophotometer, which determines the optical density of the reaction product, using a 450 nm wavelength of light.

The concentration of the construct and the control in the serum samples was determined towards a standard curve of the construct and the control, respectively. The concentration determination was performed using the sigmoidal dose-response curve with variable slope. All serum samples were tested minimally in duplicate. Average values were reported. For each sample standard deviations and precision between the different results was calculated.

Figure 6:
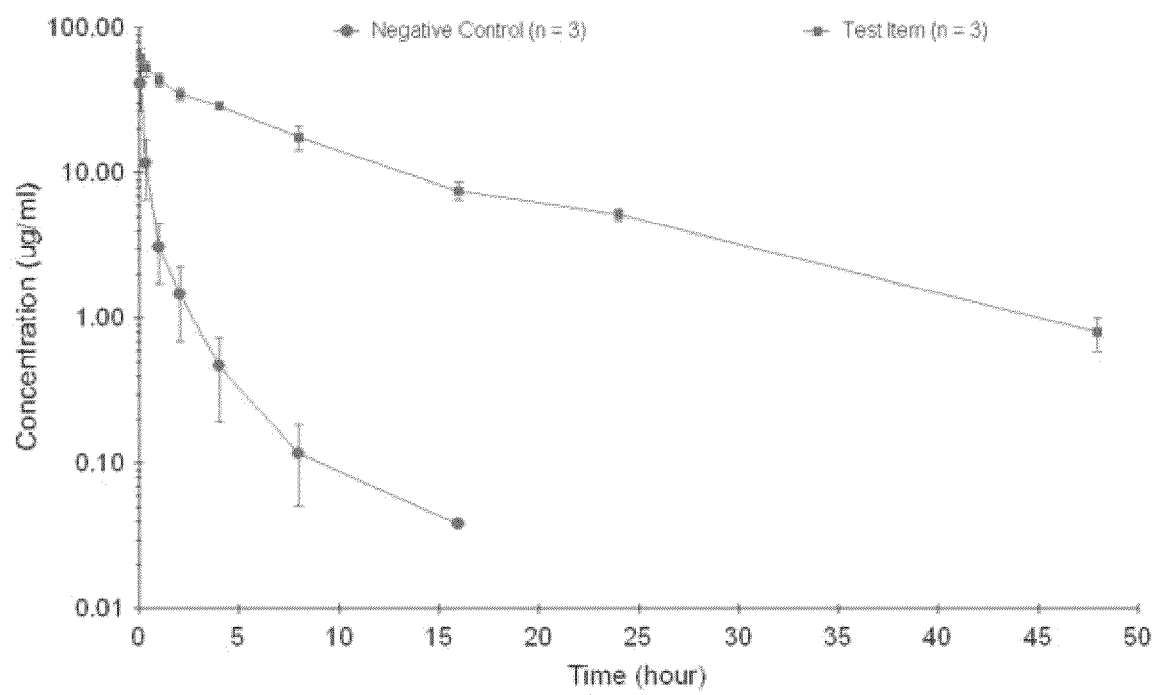

The PK profile is represented in FIG. 6.

The calculated terminal half-life of the Nanobodies® is summarized in Table IV.

TABLE IV

Terminal half-life expressed in hours obtained in cynomolgus monkeys after administration of the 2D3-9GS-EXP56E4 or the negative control (2D3).

| Nanobody ® | Terminal Half-life |
|---|---|
| 2D3-9GS-EXP56E4 | 8.54 ± 0.79 hr |
| 2D3 (control) | 2.04 ± 0.74 hr |

The data obtained in the experiment described in this Example 7 is also mentioned in Example 13 and FIG. 9.

Example 8

Crystal Structure of Peptide Based on EXP56E4 with Human Serum Albumin and In Silico Modelling of the Interactions of this Peptide with Human Serum Albumin In order to determine the binding interaction and epitopes of the peptides of the invention with human serum albumin, the crystal structure of a co-crystal of the following peptide (AAARYWDYDVFGGGTPVGGAAA; SEQ ID NO:143) and human serum albumin was determined, and also the interactions between the peptide of SEQ ID NO: 143 and human serum albumin were modeled in silico. The peptide of SEQ ID NO:143 was based on the sequence of EXP56E4 (SEQ ID NO:14) and, compared to the sequence of EXP56E4, contains an additional N-terminal alanine residue and three C-terminal alanine-residues.

It should be noted that, compared to the amino acid sequence of SEQ ID NO:1, the amino acid sequence of SEQ ID NO: 143 contains one additional N-terminal alanine residue. Thus, in the numbering used in this Example 8, position 2 corresponds to position 1 of the sequence of SEQ ID NO: 1 (see also Table II); position 3 corresponds to position2 of the sequence of SEQ ID NO: 1, etc.

The crystal structure was determined as follows: the purified proteins were used in crystallization trials employing both, a standard screen of approximately 1200 different conditions, as well as crystallization conditions identified using literature data. Conditions initially obtained have been optimized using standard strategies, systematically varying parameters critically influencing crystallization, such as temperature, protein concentration, drop ratio, etc. These conditions were also refined by systematically varying pH or precipitant concentrations. Crystals were obtained via the method of co-crystallization.

Crystals have been flash-frozen and measured at a temperature of 100K. The X-ray diffraction have been collected at the SWISS LIGHT SOURCE (SLS, Villigen, Switzerland) using cryogenic conditions. Data were processed using the programs XDS and XSCALE. The phase information necessary to determine and analyze the structure was obtained by molecular replacement. Subsequent model building and refinement was performed with the software packages CCP4 and COOT. The peptide parameterization was carried out with the program CHEMSKETCH.

Modeling of the interaction was performed using ICM-Pro (Molsoft) and Discovery Studio (Accelrys) with a force-field that is based on the parameters as described in Momany et al. (Momany et al. J. Phys. Chem. 1975, 79, 2361-2381)

In respect of human serum albumin, for the purposes of this Example 8 and the further disclosure herein, reference will be made to the sequence given under Genbank accession number AAA98797 (Minghetti et al., J. Biol. Chem. 261 (15), 6747-6757 (1986); SEQ ID NO: 144):

```
  1 mkwvtfisll flfssaysrg vfrrdahkse vahrFkdlge enfkalvlia faqylqqcpf 61 edhvklvnev tefaktcvad esaencdksl htlfgdklct vatlretyge madccakqep 121 ernecflqhk ddNPNLpRLv Rpevdvmcta fhdneetflk kYlyEIarRH pyFyapellf 181 Fakrykaaft eccqaadkaa cllpkldelr deGKasSakq rlkcaslqkf gerafkawav 241 arlsqrfpka efaevsklvt dltkvhtecc hgdllecadd radlakyice nqdsissklk 301 eccekpllek shciaevend empadlpsla adfveskdvc knyaeakdvf lgmflyeyar 361 rhpdysvvll lrlaktyett lekccaaadp hecyakvfde fkplveepqn likqncelfe 421 qlgeykfqna llvrytkkvp qvstptlvev srnlgkvgsk cckhpeakrm pcaedylsvv 481 lnQlcvlhek tpvsdrvtkc cteslvnrrp cfsalevdet yvpkefnaet ftfhadictl 541 seKerqikkq talvelvkhk pkatkeqlka vmddfaafve kcckaddket cfaeegkklv 601 aasqaalgl
```

Thus, when reference is made herein to a specific amino acid residue of human serum albumin, the numbering of this amino acid residue will be according to the above sequence. It should however be noted that the above sequence contains the following signal sequence (mkwvtfisllflfssaysrgvfrr, SEQ ID NO:145). The sequence of mature human serum albumin (without this signal sequence) is given below and in SEQ ID NO:146. This polypeptide was also used to determine the crystal structure of the co-crystal with the peptide of SEQ ID NO: 143:

```
  1 dahksevahr Fkdlgeenfk alvilafaqy lqqcpfedhv klvnevtefa ktcvadesae
 61 ncdkslhtlf gdklctvatl retygemadc cakqeperne cflqhkddNP NLpRLvRpev
121 dvmctafhdn eetflkkYly EIarRHpyFy apellfFakr ykaafteccq aadkaacllp
181 kldelrdeGK asSakqrlkc aslqkfgera fkawavarls qrfpkaefae vsklvtdltk
241 vhtecchgdl lecaddradl akyicenqds issklkecce kpllekshci aevendempa
301 dlpslaadfv eskdvcknya eakdvflgmf lyeyarrhpd ysvvlllrla ktyettlekc
361 caaadphecy akvfdefkpl veepqnhikq ncelfeqlge ykfqnallvr ytkkvpqvst
421 ptlvevsrnl gkvgskcckh peakrmpcae dylsvvlnQl cvlhektpvs drvtkcctes
481 lvnrrpcfsa levdetyvpk efnaetftfh adictlseKe rqikkqtalv elvkhkpkat
541 keqlkavmdd faafvekcck addketcfae egkklvaasq aalgl
```

[It should also be noted that Genbank accession number CAA00844 and EP 0361991 give an alternative, synthetic amino acid sequence for human serum albumin which—compared to the sequence of SEQ ID NO:144—contains one amino acid residue less than the sequence of AAA98797. In particular, in the sequence of CAA00844, and compared to the amino sequence of SEQ ID NO: 144, the amino acid residues KH on positions 463 and 464 are replaced with a single amino acid residue N at position 463. Herein, when reference is made to the amino acid sequence of human serum albumin and the amino acid residues present therein, reference is made to the sequence and numbering given in SEQ ID NO:144].

From the crystal structure and modeling data, the following observations have been made regarding the binding interaction of the peptide of SEQ ID NO: 143 and human serum albumin. It should be noted that these observations are given as exemplification only and do not limit the invention to any specific (or complete) explanation or hypothesis on where (i.e. to which epitope) and how (i.e. via which amino acid residues) the amino acid sequences of the invention bind to human serum albumin. However, it is assumed that the binding interactions and epitope(s) described below constitute one (preferred) way in which the amino acid sequences of the invention may bind to human serum albumin.

The peptide of SEQ ID NO: 143 binds in a deep subpocket of domain I of human serum albumin, and also has some interactions with residues from domain III of human serum albumin.

The peptide of SEQ ID NO: 143 may in particular bind to human serum albumin via interaction with one or more of the following amino acid residues: Asn (N) 133; Pro (P) 134; Asn (N) 135; Leu (L) 136; Leu (L) 139; Arg (R) 141; Tyr (Y) 162; Glu (E) 165; Ile (I) 166; His (H) 170; Phe (F) 173; Phe (F) 181; Gly (G) 213; Lys (K) 214; Ser (S) 217; Gln (Q) 483; and/or Lys (K) 543. These amino acid residues are indicated in UPPER CASE in the above sequences.

In respect of the primary sequence of human serum albumin, particularly important interactions appear to be the interactions of the peptide of SEQ ID NO: 143 with the stretch of amino acid residues that comprises the residues Asn (N) 133; Pro (P) 134; Asn (N) 135; Leu (L) 136; Leu (L) 139 and Arg (R) 141; with the stretch of amino acid residues that comprises the residues Tyr (Y) 162; Glu (E) 165; Ile (I) 166; His (H) 170; Phe (F) 173; Phe (F) 181; and/or with the stretch of amino acid residues that comprises the residues Gly (G) 213; Lys (K) 214 and Ser (S) 217;

In respect of the ternary structure of human serum albumin (as deducted from the X-ray and modeling data), particularly important interactions appear to be the interactions of the peptide of SEQ ID NO: 143 with a rather hydrophobic subpocket that is formed by (amongst others) residues the residues Leu (L) 139, Glu (E) 165, Ile (I) 166, His (H) 170, Phe (F) 173, Phe (F) 181, Gly (G) 213, Lys (K) 214, Ser (S) 217 and Gln (Q) 483 in human serum albumin;

The three N-terminal alanine residues (Ala-1 to Ala-3) in the peptide of SEQ ID NO: 143 could not be seen in the X-ray structure. The results from in silico modeling results suggest these alanine residues may be in contact with human serum albumin.

The Arg (R) residue at position 4 in peptide of SEQ ID NO: 143 likely forms a hydrogen bond with the amino acid residues Asn (N) 133 & Asn (N) 135 of human serum albumin; and may also forms electrostatic interactions with the main-chain oxygen atoms of the Pro (P) 134 and Leu (L) 136 residues of human serum albumin. The Arg (R) residue at position 4 in peptide of SEQ ID NO: 143 may also form an internal hydrogen bond with the Asp (D) residue at position 7 of the peptide of SEQ ID NO: 143. The crystal structure and modeling data suggests that this is likely an important residue for the interaction between the peptide of SEQ ID NO: 143 and human serum albumin;

The Tyr (Y) residue at position 5 in the peptide of SEQ ID NO: 143 likely forms a hydrogen-bond with the Lys (K) 543 residue of human serum albumin via its main-chain. The crystal structure and modeling data further suggests that the Tyr (Y) residue at position 5 in peptide of SEQ ID NO: 143 is located in a subpocket of HSA and is likely stabilized by the Trp (W) residue at position 6 of peptide of SEQ ID NO: 143. The crystal structure and modeling data also suggests that this is likely an important residue for the interaction between the peptide of SEQ ID NO: 143 and human serum albumin; and that the aromatic nature of the Tyr residue at this position, although not strictly needed at this position (the data suggests that other hydrophobic residues may be present at this position), may contribute to the stabilization with the Trp residue at position 6 of peptide of SEQ ID NO: 143;

The Trp (W) residue at position 6 in the peptide of SEQ ID NO: 143 appears to be nicely positioned between the Arg (R) 138 and Lys (K) 543 residues of human serum albumin; and likely forms strong electrostatic interactions with the Arg (R) 138 residue of human serum albumin. It also appears that the aromatic nature of the Trp (W) residue may be important for these interactions; as well as for the stabilization with the Tyr (Y) residue at position 5 in peptide of SEQ ID NO: 143. The crystal structure and modeling data suggests that this is likely an important residue for the interaction between the peptide of SEQ ID NO: 143 and human serum albumin. It should also be noted that in serum albumin of cynomolgus monkey, mouse and rat, the amino acid residue at position 138 is pro (P) instead of Arg (R); this may lead to a reduced binding affinity of the amino acid sequences of the invention for cyno, mouse and/or rat serum albumin compared to human serum albumin;

The Asp (D) residue at position 7 in the peptide of SEQ ID NO: 143 likely forms an internal hydrogen bond with the Arg (R) residue at position 4 in the peptide of SEQ ID NO: 143, and so may be important for the local conformation of the peptide. The crystal structure and modeling data also suggests that this residue may potentially form a hydrogen bond with the His (H) 170 residue of human serum albumin, i.e. via its main-chain oxygen atom (from the data, the Asp-7 side-chain does not appear to have significant interactions with human serum albumin);

The Tyr (Y) residue at position 8 in the peptide of SEQ ID NO: 143 appears to bind in a hydrophobic subpocket that is formed by the His (H) 170, Lys (K) 214, Ser (S) 217 and Gln (Q) 483 residues of human serum albumin: and may also have aromatic interactions with the His (H) 170 residue of human serum albumin (HSA) and/or internal aromatic interactions with the Phe (F) residue at position 11 of the peptide of SEQ ID NO: 143. The crystal structure and modeling data suggests that this is likely an important residue for the interaction between the peptide of SEQ ID NO: 143 and human serum albumin; but might possible be replaced by another hydrophobic residue at position 8, as the shape complementarity with the aforementioned hydrophobic subpocket could possibly be further improved;

The Asp (D) residue at position 9 in the peptide of SEQ ID NO: 143 appears to undergo electrostatic interactions with the Lys (K) 543 residue of human serum albumin; and also appears to be partially solvent exposed. The crystal structure and modeling data further suggests that this residue might possibly be replaced by a Glu (E) residue at the same position, as such a substitution might bring the carboxylic acid group closer to the Lys (K) 543 in human serum albumin and so even further improve these electrostatic interactions;

The Val (V) residue at position 10 in the peptide of SEQ ID NO: 143 appears to bind into a hydrophobic subpocket that is formed by Leu (L) 139, Glu (E) 165, Ile (I) 166 and His (H) 170 residues of human serum albumin. The crystal structure and modeling data suggests that, due to the important hydrophobic interactions and good shape complementarity with human serum albumin, this is an important residue for the interaction between the peptide of SEQ ID NO: 143 and human serum albumin;

The Phe (F) residue at position 11 in the peptide of SEQ ID NO: 143 appears to bind in a deep hydrophobic subpocket of human serum albumin that is formed by the Ile (I) 166, His (H) 170, Phe (F) 173, Phe (F) 181 & Gly (G) 213 residues of human serum albumin. Also, the main chain oxygen atom of the Phe (F) residue at position 11 in the peptide of SEQ ID NO: 143 appears likely to form a hydrogen-bond with the Tyr (Y) 162 residue in human serum albumin. The crystal structure and modeling data suggests that this is likely an important residue for the interaction between the peptide of SEQ ID NO: 143 and human serum albumin;

The three glycine residues at positions 12 to 14 of the peptide of SEQ ID NO: 143 appear to bind deep into domain I of human serum albumin and to make a turn which optimally fits with the surface of human serum albumin. The crystal structure and modeling data suggests that this likely is important for the interaction between the peptide of SEQ ID NO: 143 and human serum albumin;

The Thr (T) residue at position 15 of the peptide of SEQ ID NO: 143 appears to form two main-chain hydrogen bonds with the Leu (L) 139 and Arg (R) 141 residues. In addition, the Thr (T) residue at position 15 of the peptide of SEQ ID NO: 143 appears to form an internal hydrogen bond with the Asp (D) residue at position 7 of the peptide of SEQ ID NO: 143; might possibly also form a stabilizing internal hydrogen-bond with Asp (D) residue at position 9 of the peptide of SEQ ID NO: 143.

The Pro (P) residue at position 16 of the peptide of SEQ ID NO: 143 might have a function in positioning of (and/or constraining the optimal conformation for) the two hydrogen bonds of that are formed by the Thr (T) residue at position 15 of the of peptide of SEQ ID NO: 143

From the X-ray structure, no observations could be made for the C-terminal part of the peptide of SEQ ID NO: 143 not seen in X-ray structure. Modeling suggests that the C-terminal stretch does not interact with HSA (except maybe for the Val (V) residue at position 16, which is the residue from the C-terminal end that is closest to human serum albumin compared to the other C-terminal residues. The modelling data suggests the possibility that the Val residue at position 16 could possibly be replaced by a larger (d-) residue (such as, in particular, a Glu residue) which could possibly interact with the Arg (R) 114 residue of human serum albumin and in this way potentially also indirectly contribute to the further stabilization of the Trp (W) residue at position 6 (HSA) of the peptide of SEQ ID NO: 143.

Again, although the abovementioned X-ray and modeling data, as well as the observations made based on that data, are non-limiting and given as exemplification only, it is assumed that other amino acid sequences with the same or comparable amino acid sequences at positions corresponding to those mentioned above will undergo interactions with human serum albumin that are essentially the same as and/or essentially similar to the interactions described above for the peptide of SEQ ID NO: 143; and that the abovementioned stretches of amino acid residues in the primary sequence of human serum albumin and/or the binding pockets on human serum albumin described above form one or more important epitopes for the binding of the amino acid sequences of the invention to human serum albumin.

Example 9

Affinity Maturation of an Amino Acid Sequence of the Invention

In this example, 56E4 (AA<u>RYWDYDV</u>FGGGTPVGG, SEQ ID NO:14) was chosen as a starting point for affinity maturation. 8 residues (bold/underlined) were chosen for randomization via parsimonious mutagenesis using a coding sequence for 56E4 but synthesized with a 70:10:10:10 mixture of bases (70% original base and 10% of the other three bases), resulting in a frequency of 50% of the wild type amino at each randomized position.

The randomized peptide was expressed on the surface of M13 bacteriophages as N-terminal fusion to geneIII protein using a pUC19-derived phagemid vector. Four rounds of in solution selections were performed using biotinylated human serum albumin (HSA: A5763, Sigma), concentrations ranging from 1M to 1 nM. After incubation for 2 h in presence of ovalbumin or casein as blocking agent, phages bound to biotinylated HSA were captured on neutravidin and after washing the bound phages were eluted with 100 mM triethylamine and neutralized with 1M Tris pH 7.5.

Figure 7A:
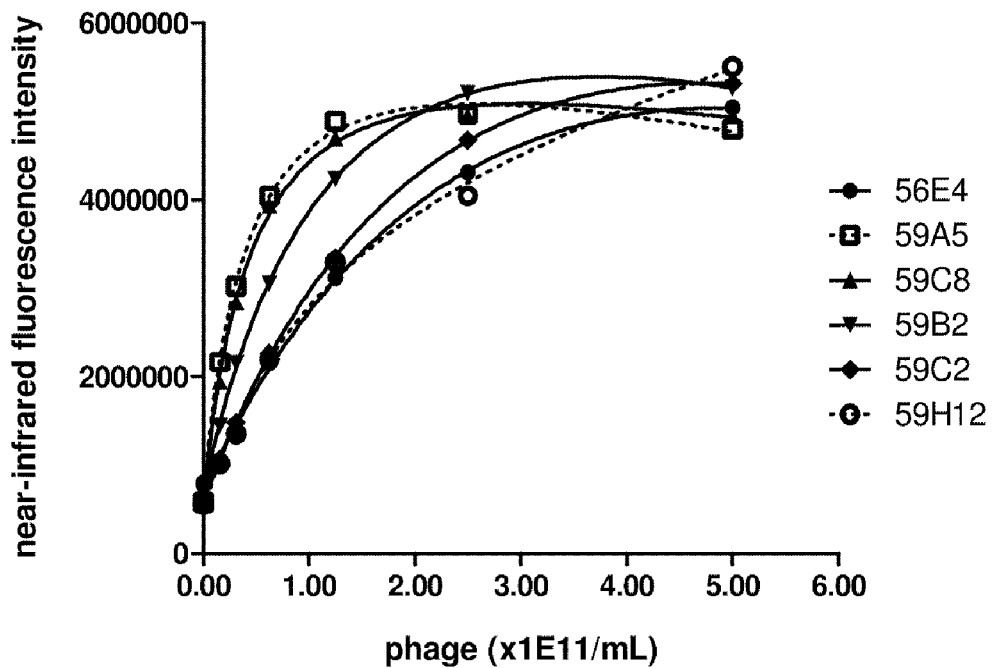
FIGS. 7A to 7C are diagrams showing the results obtained in Example 9 with the affinity matured versions of 56E4 described in Example 9 when these were tested in the phage competition assay described in Example 5.
Figure 7B:
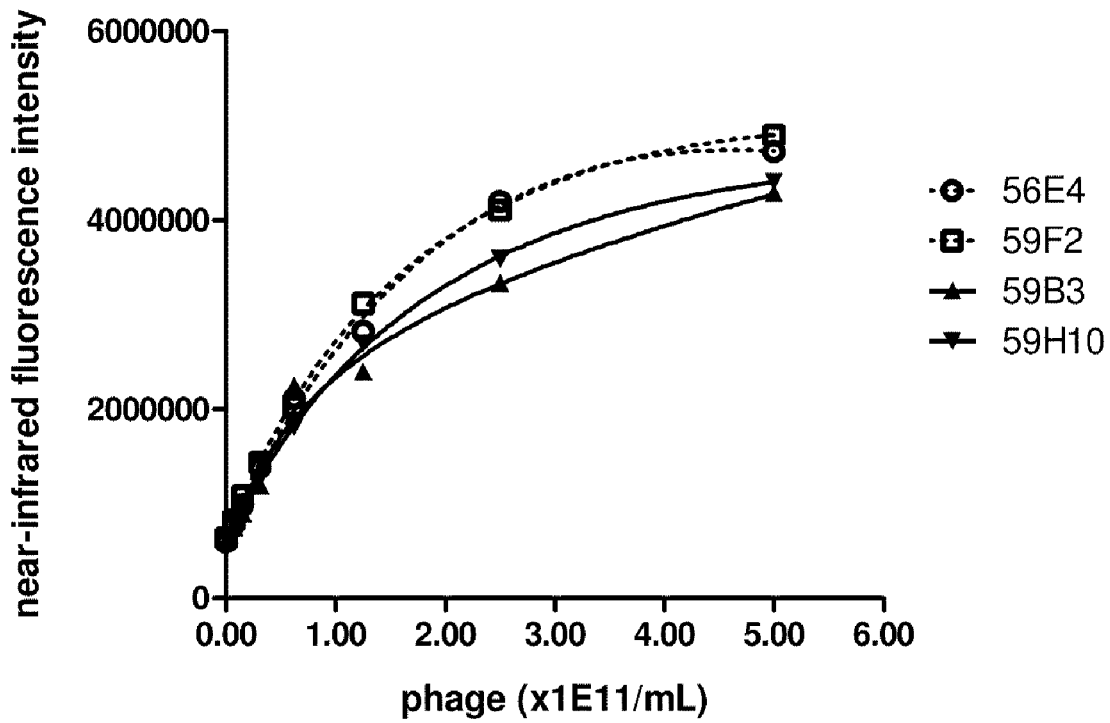
Figure 7C:
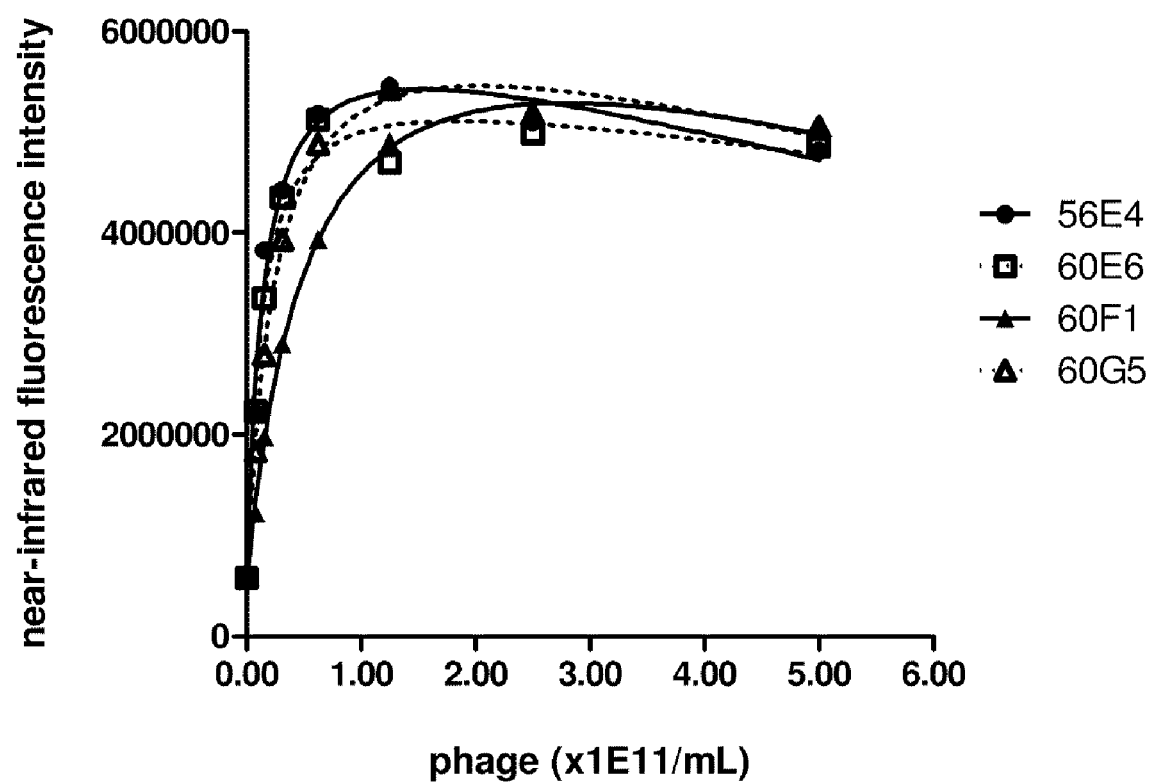

After respectively three and four selection rounds, monoclonal phage were screened for binding on HSA, in the manner described in Example 2. Clones that bind to HSA (FIGS. 7A to 7C and Table V) were screened in phage competition ELISA, in the manner described in Example 5. The ratio of phage binding was calculated by the following equation: fluorescence signal of well with 2 µM competitor/fluorescence signal of well with no competitor (Table VI).

TABLE V

Alignment of clones resulting from affinity maturation of 56E4 (shown at top) that bind to HSA

| Clone | SEQ ID NO: | sequence |
|---|---|---|
| 59E4 | SEQ ID NO: 14 | AARYWDYDVFGGGTPVGG |
| 59A5 | SEQ ID NO: 147 | AARWWDYDVFGGGTPVGG |
| 59C8 | SEQ ID NO: 148 | AARYWDWDVFGGGTPVGG |
| 59F2 | SEQ ID NO: 149 | AARYWDFDVFGGGTPVGG |
| 59B3 | SEQ ID NO: 150 | AARYWDFDAFGGGTPVGG |
| 59B2 | SEQ ID NO: 151 | AARFWDYDVFGGGTPVGG |
| 60 E6 | SEQ ID NO: 152 | AARYWDYDVFGGGTPVDG |
| 60F1 | SEQ ID NO: 153 | AARYWDYDVFGGGSQVGG |
| 60G5 | SEQ ID NO: 154 | AARYWDYDVFGGGSPVGG |
| 59H12 | SEQ ID NO: 155 | AARSWDFDVFGGGTPVGG |
| 59C2 | SEQ ID NO: 156 | AARDWDFDVFGGGTPVGG |
| 59H10 | SEQ ID NO: 157 | AARYWDFDVFGGGSPVGG |

TABLE VI

Solution binding competition assay for 56E4, 59C2, 59F2 and 59H12

| Clone | Ratio 2 µM/0 µM HSA |
|---|---|
| 56E4 | 0.82 |
| 59C2 | 0.91 |
| 59F2 | 0.69 |
| 59H12 | 0.87 |

Example 10

Construction of a Nanobody-Expedite Fusion Protein and Analysis of Binding to HSA HSA-binding peptides 56E4 (reference), 59C2, 59F2 and were each genetically fused at the C-terminus of the Nanobody 2D3 (SEQ ID NO: 137) using the linker sequence of SEQ ID NO: 140 (that comprises a Gly4Ser-Gly3Ser linker and a flanking amino acid sequence GSA) and the C-terminal tag of SEQ ID NO:141. The resulting fusion proteins (for which the sequence are given below) were expressed in *E. coli* TG1 cells and purified by IMAC/SEC, using standard vectors, conditions and techniques.

2D3-9GS-56E4-MycHis:

[SEQ ID NO: 158]
EVQLVESGGSLVQPGGSLRLSCAASGFTFDDYAMSWVRQVPGKGLEWVSS
INWSGTHTDYADSVKGRFTISRNNANNTLYLQMNSLKSEDTAVYYCAKNW
RDAGTTWFEKSGSAGQGTQVTVSSGGGGSGGGSAAARYWDYDVFGGGTPV
GGAAAEQKLISEEDLNGAAHHHHHH

2D3-9GS-59F2-MycHis:

[SEQ ID NO: 159]
EVQLVESGGSLVQPGGSLRLSCAASGFTFDDYAMSWVRQVPGKGLEWVSS
INWSGTHTDYADSVKGRFTISRNNANNTLYLQMNSLKSEDTAVYYCAKNW
RDAGTTWFEKSGSAGQGTQVTVSSGGGGSGGGSAAARYWDFDVFGGGTPV
GGAAAEQKLISEEDLNGAAHHHHHH

2D3-9GS-59C2-MycHis:

[SEQ ID NO: 160]
EVQLVESGGSLVQPGGSLRLSCAASGFTFDDYAMSWVRQVPGKGLEWVSS
INWSGTHTDYADSVKGRFTISRNNANNTLYLQMNSLKSEDTAVYYCAKNW
RDAGTTWFEKSGSAGQGTQVTVSSGGGGSGGGSAAARDWDFDVFGGGTPV
GGAAAEQKLISEEDLNGAAHHHHHH

2D3-9GS-59H12-MycHis:

[SEQ ID NO: 161]
EVQLVESGGSLVQPGGSLRLSCAASGFTFDDYAMSWVRQVPGKGLEWVSS
INWSGTHTDYADSVKGRFTISRNNANNTLYLQMNSLKSEDTAVYYCAKNW
RDAGTTWFEKSGSAGQGTQVTVSSGGGGSGGGSAAARSWDFDVFGGGTPV
GGAAAEQKLISEEDLNGAAHHHHHH

The binding of the resulting 2D3-9GS-56E4-MycHis, 2D3-9GS-59C2-MycHis, 2D3-9GS-59F2-MycHis and 2D3-9GS-59H12-MycHis fusion proteins to human and cynomolgus serum albumin (HSA and CSA respectively) was determined using surface plasmon resonance analysis. For this purpose, binding to HSA and CSA was assessed in BIAcore™ 3000, by injecting concentration series of the fusion proteins ranging from 2 µM to 200 nM on a CM5 chip coated with ~3000 RU HSA or CSA. Coating of the chip (CM5) was performed by amine coupling using NHS/EDC for activation and ethanolamine for deactivation (Biacore amine coupling kit). HBS-EP was used as flow buffer at a rate of 45 µl min-1. 90 µl of sample was injected for 120 s.

Figure 8A:
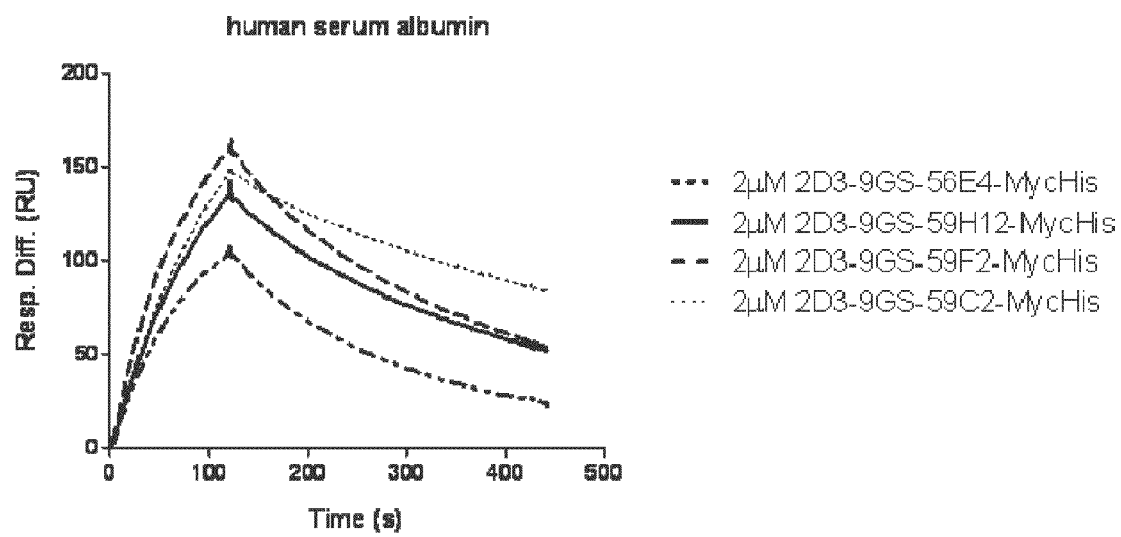
FIGS. 8A and 8B are diagrams showing the results obtained in Example 10 for the binding of the fusion proteins compounds 2D3-9GS-56E4-MycHis, 2D3-9GS-59C2-MycHis, 2D3-9GS-59F2-MycHis and 2D3-9GS-59H12-MycHis to human serum albumin (FIG. 8A) and cynomolgus serum albumin (FIG. 8B).
Figure 8B:
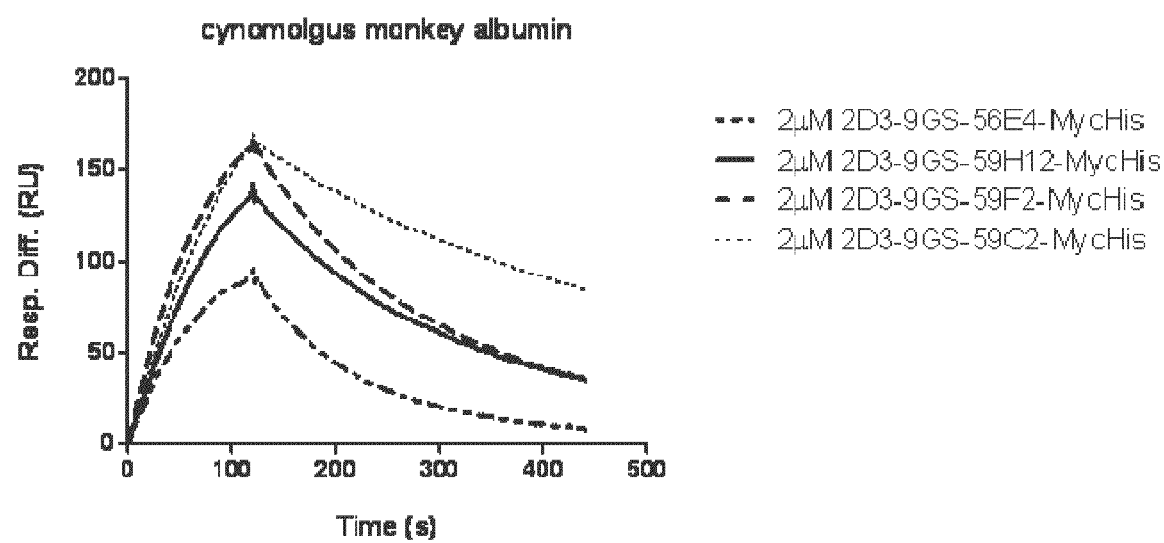

FIGS. 8A and 8B show improved binding of the 2D3-9GS-59C2-MycHis, 2D3-9GS-59F2-MycHis and 2D3-9GS-59H12-MycHis fusion protein to HSA and CSA compared to 2D3-9GS-56E4-MycHis. Calculated affinities are shown in Table VII.

TABLE VII

Kinetic values for MycHis tagged 2D3-Expedite fusions

| | Human serum albumin | | | Cynomolgus monkey serum albumin | | |
|---|---|---|---|---|---|---|
| | ka (1/ms) | Kd (1/s) | KD (nM) | ka (1/ms) | Kd (1/s) | KD (nM) |
| 2D3-9GS-56E4-MycHis | 5.02E+03 | 4.97E−03 | 991 | 4.01E+03 | 8.45E−03 | 2110 |
| 2D3-9GS-59H12-MycHis | 4.59E+03 | 3.04E−03 | 663 | 3.45E+03 | 4.41E−03 | 1280 |
| 2D3-9GS-59F2-MycHis | 6.14E+03 | 3.51E−03 | 571 | 4.85E+03 | 5.04E−03 | 1040 |
| 2D3-9GS-59C2-MycHis | 3.73E+03 | 1.79E−03 | 481 | 2.75E+03 | 2.13E−03 | 775 |

Example 11

Construction of Anti-HER2Nanobody-Expedite Fusion Proteins for PK Study

The HSA-binding peptide 59C2 without the two N-terminal alanine residues (RDWDFDVFGGGTPVGG; SEQ ID NO: 162) was genetically fused with a Gly4Ser-Gly3Ser (9GS) linker sequence (GGGGSGGGS; SEQ ID NO:163) at the C-terminus of the anti-HER2 Nanobody 2D3 (SEQ ID NO: 137). The fusion protein was expressed and produced in essentially the same manner as described in Example 12.

The resulting fusion protein had the following sequence:

2D3-9GS-59C2:

[SEQ ID NO: 164]
EVQLVESGGSLVQPGGSLRLSCAASGFTFDDYAMSWVRQVPGKGLEWVSS

INWSGTHTDYADSVKGRFTISRNNANNTLYLQMNSLKSEDTAVYYCAKNW

RDAGTTWFEKSGSAGQGTQVTVSSGGGGSGGGSRDWDFDVFGGGTPVGG

The binding of 2D3-9GS-59C2 to human, cynomolgus monkey and baboon serum albumin was determined using surface plasmon resonance analysis and compared with binding of and 2D3-9GS-56E4 (SEQ ID NO:142), essentially as described in Example 7. The binding was determined in BIAcore™ 3000, by injecting concentration series of the fusion proteins ranging from 2 μM to 200 nM on a CM5 chip coated with ~3000 RU HSA or CSA. Coating of the chip (CM5) was performed by amine coupling using NHS/EDC for activation and ethanolamine for deactivation (Biacore amine coupling kit). HBS-EP was used as flow buffer at a rate of 45 μl min-1. 90 μl of sample was injected for 120 s. Calculated affinities are shown in Table VIII.

TABLE VIII

Kinetic values for 2D3-9GS-56E4 and 2D3-9GS-59C2

| | Human serum albumin | | | Cynomolgus monkey serum albumin | | |
|---|---|---|---|---|---|---|
| | ka (1/ms) | Kd (1/s) | KD (nM) | ka (1/ms) | Kd (1/s) | KD (nM) |
| 2D3-9GS-56E4 | 1.04E+04 | 4.97E−03 | 342 | 1.71E+04 | 8.47E−03 | 495 |
| 2D3-9GS-59C2 | 8.76E+03 | 1.94E−03 | 221 | 8.98E+03 | 2.47E−03 | 276 |

Example 12

Construction of Anti-VWF Nanobody-Expedite Fusion Proteins for PK/PD Study

The HSA-binding peptide 59C2 (without the two N-terminal alanine residues; SEQ ID NO: 162) was genetically fused either as a monomer or as a dimer with a Gly4Ser-Gly3Ser (9GS) linker sequence between the two peptides (RDWDFDVFGGGTPVGGGGGSGGGSRDWDFDVFGGGTPVGG; SEQ ID NO: 166) to the bivalent anti-VWF Nanobody 12A2_sv1-AAA-12A2_sv1 (vWF-001):

[SEQ ID NO: 165]
DVQLVESGGGLVQPGGSLRLSCAASGRTFSYNPMGWFRQAPGKGRELVAA

ISRTGGSTYYPESVEGRFTISRDNAKRTVYLQMNSLRAEDTAVYYCAAAG

VRAEQGRVRTLPSEYTFWGQGTQVTVSSAAAEVQLVESGGGLVQPGGSLR

LSCAASGRTFSYNPMGWFRQAPGKGRELVAAISRTGGSTYYPESVEGRFT

ISRDNAKRTVYLQMNSLRAEDTAVYYCAAAGVRAEQGRVRTLPSEYTFWG

QGTQVTVSS either at the C-terminus or interspaced between the two VHH building blocks via the Gly4Ser-Gly3Ser (9GS) linker.

For production, *Escherichia coli* strain TG1 containing the pAX102 plasmids expressing the constructs were inoculated in 200 mL TB supplemented with 50 mg/L kanamycin (Kan) and 2% glucose, and incubated ON at 30° C. and 200 rpm. For each construct 1×10 L bioreactor containing TBKan (50 mg/L)+2% glucose was inoculated with 1/50 of the obtained overnight pre-culture and further grown at 37° C. during the following batch phase to obtain biomass. After 3 hours, the cultures were induced with 1 mM IPTG and further grown at 30° C. for another 3 hours during induction phase until OD600>10. The cultures were harvested by centrifugation (Sigma 8K10 rotor; 7000 rpm; 20'; 4° C.), after which the clarified fermentation broth was stored at 4° C. and the cell pellets were stored at −20° C.

For purification, periplasmic extracts were prepared by re-suspending the pellets in 1 to 1.5 L peri-buffer (50 mM NaH2PO4, 300 mM NaCl pH 8.0) and incubating for 40 minutes at 4° C. on a shaking platform at 200 rpm. The suspensions were centrifuged at 7000 rpm for 40 minutes to clear the cell debris from the periplasmic extract, followed by a filtration step using a 0.45 μm filter. All the fusion proteins were captured via affinity chromatography using MabCapture A (Poros), followed by intermediate purification step via either CEX for the vWF-EXP molecules [Poros 50HS (Poros); equilibration buffer PBS, elution buffer PBS/1M NaCl, followed by binding and elution for vWF0056 on Source 15S; equilibration buffer 25 mM Hepes, 75 mM NaCl pH=8.0 and elution buffer: 25 mM Hepes, 175 mM NaCl pH=8.0] or via AEX for 2D3-EXP59C2 [Poros 50HQ (Poros); equilibration buffer 25 mM Tris pH7.66, elution buffer 25 mM Tris pH7, 79-500 mM NaCl]. Finally, all samples were treated with OGP for LPS-removal, followed by a final size exclusion chromatography step using Superdex 75 pg (GE Healthcare) in D-PBS. The OD280 nm was measured and the concentrations for the different fusions were calculated. Samples were after sterile filtration stored at −20 C. LC/MS analysis indicated experimentally observed mass was in agreement with the respectively theoretically expected masses of each construct.

The resulting fusion proteins had the following sequences:

```
12A2_sv1-9GS-59C2-9GS-12A2_sv1 (vWF-0053):
                                         [SEQ ID NO: 167]
DVQLVESGGGLVQPGGSLRLSCAASGRTFSYNPMGWFRQAPGKGRELVAA
ISRTGGSTYYPESVEGRFTISRDNAKRTVYLQMNSLRAEDTAVYYCAAAG
VRAEQGRVRTLPSEYTFWGQGTQVTVSSGGGGSGGGSRDWDFDVFGGGTP
VGGGGGGSGGGSEVQLVESGGGLVQPGGSLRLSCAASGRTFSYNPMGWFR
QAPGKGRELVAAISRTGGSTYYPESVEGRFTISRDNAKRTVYLQMNSLRA
EDTAVYYCAAAGVRAEQGRVRTLPSEYTFWGQGTQVTVSS

12A2_sv1-9GS-59C2-9GS-59C2-9GS-12A2_sv1
(vWF-0054):
                                         [SEQ ID NO: 168]
DVQLVESGGGLVQPGGSLRLSCAASGRTFSYNPMGWFRQAPGKGRELVAA
ISRTGGSTYYPESVEGRFTISRDNAKRTVYLQMNSLRAEDTAVYYCAAAG
VRAEQGRVRTLPSEYTFWGQGTQVTVSSGGGGSGGGSRDWDFDVFGGGTP
VGGGGGGSGGGSRDWDFDVFGGGTPVGGGGGSGGGSEVQLVESGGGLVQ
PGGSLRLSCAASGRTFSYNPMGWFRQAPGKGRELVAAISRTGGSTYYPES
VEGRFTISRDNAKRTVYLQMNSLRAEDTAVYYCAAAGVRAEQGRVRTLPS
EYTFWGQGTQVTVSS

12A2_sv1-AAA-12A2_sv1-9GS-59C2 (vWF-0055):
                                         [SEQ ID NO: 169]
DVQLVESGGGLVQPGGSLRLSCAASGRTFSYNPMGWFRQAPGKGRELVAA
ISRTGGSTYYPESVEGRFTISRDNAKRTVYLQMNSLRAEDTAVYYCAAAG
VRAEQGRVRTLPSEYTFWGQGTQVTVSSAAAEVQLVESGGGLVQPGGSLR
LSCAASGRTFSYNPMGWFRQAPGKGRELVAAISRTGGSTYYPESVEGRFT
ISRDNAKRTVYLQMNSLRAEDTAVYYCAAAGVRAEQGRVRTLPSEYTFWG
QGTQVTVSSGGGGSGGGSRDWDFDVFGGGTPVGG

12A2_sv1-AAA-12A2_sv1-9GS-59C2-9GS-59C2
(vWF-0056):
                                         [SEQ ID NO: 170]
DVQLVESGGGLVQPGGSLRLSCAASGRTFSYNPMGWFRQAPGKGRELVAA
ISRTGGSTYYPESVEGRFTISRDNAKRTVYLQMNSLRAEDTAVYYCAAAG
VRAEQGRVRTLPSEYTFWGQGTQVTVSSAAAEVQLVESGGGLVQPGGSLR
LSCAASGRTFSYNPMGWFRQAPGKGRELVAAISRTGGSTYYPESVEGRFT
ISRDNAKRTVYLQMNSLRAEDTAVYYCAAAGVRAEQGRVRTLPSEYTFWG
QGTQVTVSSGGGGSGGGSRDWDFDVFGGGTPVGGGGGSGGGSRDWDFDV
FGGGTPVGG
```

Example 13

Pharmacokinetic Profile in Male Cynomolgus Monkeys: Monovalent Nanobody

The Nanobody construct tested was a fusion of the peptide 59C2 (SEQ ID NO: 156) and the Nanobody 2D3 (SEQ ID NO:137). The sequence of this construct (2D3-9GS-59C2) is given in Example 11 and SEQ ID NO: 164.

In this Example 13 and its corresponding FIG. 9, the data for another construct of the invention (2D3-9GS-56E4; SEQ ID NO:142) as obtained in Example 7 is also presented.

As a negative control, the Nanobody 2D3 was used.

For blood sampling and processing, the pharmacokinetic profile of the constructs (2D3-9GS-EXP56E4 and 2D3-9GS-EXP59C2) and the negative control 2D3 were determined in male Cynomolgus monkeys of approximately 3 to 4 years old and was compared to that of the control (2D3). The constructs and the control were administered to three monkeys at a dose of 2 mg/kg by intravenous bolus injection. Blood samples 2D3 and for 2D3-9GS-EXP56E4 were taken at predose, 5 min, 20 min, 1 h, 2 h, 4 h, 8 h, and 16 h (test day 1), and on test days 2, 3, 5, 7, 9, 12, 15, 18, 21, 24, 27, 30, 33, 36, 39, 42, 45, 48, 51, 54, and 57. While, for 2D3-9GS-59C2 blood samples were taken only up to test day 33. In order to obtain at least 0.25 mL serum per animal per sampling time, a sufficient volume of whole blood was withdrawn per sampling time and the serum was isolated after 1 h of incubation at 37° C. The serum samples were stored at −80° C. until analysis.

For bioanalytical determination of the construct and the control article in monkey serum, serum samples were tested for serum levels of the constructs and control, respectively, using the following ELISA assay. 96-well microtiter plates (Maxisorp, Nunc, Wiesbaden, Germany) were coated for 1 hour at 37° C. with Recombinant Human ErbB2/Fc Chimera, CF (R&D Systems, Minneapolis) in PBS at 3 µg/mL for the negative control and 4.5 µg/mL for the test item. Wells were aspirated and blocked for 30 minutes at room temperature (RT) with SuperBlock®T20 PBS (Pierce, Rockford, Ill.). After this blocking step, wells were washed with PBS-0.05% Tween20. Preparations for the standards, QC samples and dilutions of the test samples were performed in a non-coated (polypropylene) plate.

A standard curve and QC-samples were obtained as follows: solutions at the required concentrations were prepared in PBS 0.1% casein and spiked into 100% monkey serum. To prepare standards and QC samples, a 1/10 dilution of the pure monkey serum dilutions was made in PBS-0.1% casein.

The dilution factors for the test samples were estimated, and varied from 1/10 to 1/500. Samples were diluted 1/10 in PBS 0.1% casein in a first step, and if needed, further dilution was done in PBS 0.1% casein containing 10% monkey serum. These sample dilutions were further serially diluted 1/5 in PBS 0.1% casein with 10% monkey serum over 2 wells.

Standards, QC samples and the 1/5 dilutions of the test samples were transferred onto the coated plate and incubated for 1 hour at RT. Afterwards the plates were washed and rabbit polyclonal anti-VHH K1, purified against protein A and Her2/Fc depleted, was added at 1 µg/mL in PBS 0.1% casein, and incubated for 1 hour at RT. After washing a 1/2000 dilution in PBS 0.1% casein of horse radish peroxidase labelled goat anti-rabbit (Dakocytomation, Denmark) was added to the plate and incubated for 30 minutes at RT. This enzyme catalyzes a chemical reaction with the substrate sTMB (3,3',5,5'-tetramethylbenzidine, SDT reagents, Brussels, Belgium), which results in a calorimetric change. After stopping this reaction after 15 minutes using HCl (1N), the intensity of the color was measured by a spectrophotometer, which determines the optical density of the reaction product, using a 450 nm wavelength of light.

The concentration of the constructs and the control in the serum samples was determined towards a standard curve of the constructs and the control, respectively. The concentration determination was performed using the sigmoidal dose-response curve with variable slope. All serum samples were tested minimally in duplicate. Average values were reported. For each sample standard deviations and precision between the different results was calculated.

For the analysis of the pharmacokinetic data, descriptive statistics (mean and SD) were calculated per dose group and per sampling time point using Microsoft Excel 2007. In case all three values were BQL, BQL was reported. When one or two out of three values were BQL, BQL values were set to zero and the mean calculated. Individual serum concentration-time profiles were subjected to non-compartmental analysis (NCA) (Model 201; i.v. bolus injection) using Win-Nonlin Pro 5.1 (Pharsight Corporation, USA; 2006). The area under the curve (AUC) was estimated using the lin up/log down rule. LLOQ values were treated as missing, except when comprised between two values above the LLOQ, then they were set to zero. The concentration at time zero (C0) was estimated through back-calculation based on the two first data points. The terminal elimination half-life ($t^{1/2}$) was calculated automatically (best-fit) using a log-linear regression of the non-zero concentration-time data of the log-linear portion of the terminal phase. A minimum of three points were considered for the determination of λz.

The following main pharmacokinetic parameters were estimated: the serum concentration at time zero (C0); the area under the serum concentration-time curve extrapolated to infinity (AUCinf), total body clearance (CL), volume of distribution at steady-state (Vdss), and the terminal half-life ($t\frac{1}{2}$).

The results (for both the construct 2D3-9GS-59C2 as described in this Example 13, as well as the construct 2D3-9GS-56E4 as described in Example 7) are shown in FIG. 9. In this FIG. 9, the mean serum concentration time profile of 2D3-9GS-EXP56E4, 2D3-9GS-EXP59C2 and 2D3 following an i.v. bolus administration at 2 mg/kg of 2D3-9GS-EXP56E4, 2D3-9GS-EXP59C2 (test items) and 2D3 (control article), respectively in the male Cynomolgus monkey is depicted.

In Table IX, the main pharmacokinetic parameters of 2D3-9GS-EXP56E4, 2D3-9GS-EXP59C2, and 2D3 in the male Cynomolgus monkey are listed.

TABLE IX

Main pharmacokinetic parameters (mean +/− SD; n = 3) of 2D3-9GS-EXP56E4, 2D3-9GS-EXP59C2 (test items) and 2D3 (control article) following i.v. bolus administration of 2 mg/kg 2D3-9GS-EXP56E4, 2D3-9GS-EXP59C2 or 2D3, respectively in the male Cynomolgus monkey.

| Parameter | Units | 2D3-9GS-EXP56E4 | | 2D3-9GS-EXP59C2 | | 2D3 | |
|---|---|---|---|---|---|---|---|
| | | Mean | SD | Mean | SD | Mean | SD |
| C0 | ug/ml | 66.8 | 10.2 | 62.5 | 2.5 | 63.0 | 20.1 |
| AUCinf | ug * h/ml | 458 | 17 | 1540 | 98 | 19.9 | 8.6 |
| CL | ml/h * kg | 4.37 | 0.17 | 1.30 | 0.08 | 114 | 48 |
| Vdss | ml/kg | 50.3 | 4.5 | 45.5 | 5.54 | 116 | 34 |
| t½ | h | 8.54 | 0.79 | 20.9 | 4.23 | 2.04 | 0.74 |

Following an i.v. dose of 2 mg/kg, the C0-values were comparable for all three compounds. However, the exposure and the corresponding total body clearance (CL) after administration of 2D3-9GS-EXP56E4 and 2D3-9GS-EXP59C2 was respectively substantially higher and lower (on average 23-fold for 2D3-9GS-EXP56E4 and 77-fold for 2D3-9GS-EXP59C2, respectively) than after administration of the control article, 2D3.

The estimated values of the volume of distribution at steady-state (Vdss) were lower after administration of 2D3-9GS-EXP56E4 and 2D3-9GS-EXP59C2, relative to 2D3: 2D3-9GS-EXP56E4 and 2D3-9GS-EXP59C2 had mean Vdss-values which were respectively 2.3- and 2.6-fold lower compared to 2D3.

The terminal half-life (t½) was increased 4.2, and 10-fold from ca 2.0 h for 2D3 to ca 8.5 h for 2D3-9GS-EXP56E4, and to about 21 h for 2D3-9GS-EXP59C2, mainly as a result of the markedly decreased CL.

Example 14

Pharmacokinetic Profile in Male Cynomolgus Monkeys: Bivalent Nanobody Constructs The bivalent Nanobody constructs tested were the constructs vWF 0053 (SEQ ID NO:167); vWF 0055 (SEQ ID NO:169) and vWF-0056 (SEQ ID NO:170) described in Example 12. Of these, vWF-0056 (SEQ ID NO:170) has a C-terminal tag comprising two amino acid sequences of the invention linked via a linker (see SEQ ID NO:166). The corresponding bivalent Nanobody without any amino acid sequence of the invention (vWF-001, SEQ ID NO:165) was used as a reference.

The pharmacokinetic profile of the constructs was analyzed in male cynomolgus monkeys of approximately 3 to 4 years old and was compared to the reference (SEQ ID NO:165). The constructs and the control were each injected in three monkeys at a dose of 2 mg/kg via an intravenous bolus injection. Blood samples were taken at predose, 5 min, 20 min, 1 h, 2 h, 4 h, 8 h (test day 1) after administration and at test days 2, 3, 5, 7, 9, 12, 15, 18, 21, 24, 27, 30, 33. In order to obtain at least 1 mL plasma per animal per sampling time, a sufficient volume of whole blood was withdrawn per sampling time. Plasma was collected after whole blood centrifugation for 30 minutes at 2200 g at room temperature (RT). The plasma samples were stored at −80° C. until analysis.

For bioanalytical determination of constructs and control article in monkey plasma, plasma samples were tested for levels of constructs and the control using ELISA based PK assays. The detection of control and constructs in the ELISA assays is based on the binding of these Nanobodies with vWF and the assay set-ups are as such that total vWF-binding Nanobody is detected.

For the reference (SEQ ID NO:165) and the construct of SEQ ID NO:167, 96-well microtiter plates (Maxisorp, Nunc, Wiesbaden, Germany) were coated overnight at 4° C. with neutravidin (Pierce) in 10:10 buffer at 3 µg/ml. Wells were aspirated and blocked for 1 hour at RT with PBS/1% casein. After this blocking step, wells were washed with PBS/0.05% Tween20. A biotinylated bivalent Nanobody against the constructs was added to the neutravidin coated plate at 2 µg/ml in PBS/0.1% casein and incubated for 1 hour at RT. After the incubation step of this capture tool, wells were washed 3 times with PBS/0.05% Tween20.

Preparations of the standards, QC samples and dilutions of the test samples were performed in a non-coated (polypropylene) plate. For the standard curve and QC-samples, solutions at the required concentrations were prepared in PBS/0.1% casein and spiked into 100% monkey plasma. To prepare standards and QC samples, a 1/100 dilution of the pure monkey plasma dilutions was made in IgM-Reducing Agent (Immunochemistry Technologies, Bloomington, USA) supplemented with 2.5% pooled human plasma (referred to as sample diluent). For the test samples, dilution factors for the test samples were estimated, and ranged between 1/100 to 1/9000 for the reference of SEQ ID NO:165 tests and between 1/100 and 12000 for the construct of SEQ ID NO: 167. Samples were diluted 1/100 in sample diluent in a first step, and if needed, further dilution was done in sample diluent supplemented with 1% cynomolgus plasma.

Standards, QC samples and diluted test samples were transferred onto the coated plate and incubated for 1 hour at RT. Afterwards the plates were washed followed by a complexation step with purified vWF (ZLB Behring). vWF diluted to 2.5 µg/ml for the assay for the reference of SEQ ID NO:165 and to 3 µg/ml for the assay for the construct of SEQ ID NO: 167 in PBS/0.1% casein was incubated on the plates for 30 minutes at RT. Plates were washed and Nanobody/vWF complexes bound to the capture tool detected with Rabbit anti-human vWF Ab (Dako, Denmark), diluted 1/2000 in PBS/0.1% casein and incubated for 30 minutes at RT. After washing, a 1/15000 dilution in PBS/0.1% casein of Horse-Radish-Peroxidase labelled goat anti-rabbit Ab (Dako, Denmark) was added to the plate and incubated for 30 minutes at RT. The enzyme coupled to the Ab catalyzes a chemical reaction with the substrate sTMB (3,3',5,5'-tetramethylbenzidine, SDT reagents, Brussels, Belgium), resulting in a colorimetric change. After stopping this reaction after 10 minutes using HCl (1N), the intensity of the colour was measured using a spectrophotometer at 450 nm.

The concentrations of the reference of SEQ ID NO:165 or the construct of SEQ ID NO: 167, respectively, in the plasma samples were determined based on the parameters of a 4-parameter logistic fit of the standard curve (prepared using the reference of SEQ ID NO:165 or the construct of SEQ ID NO: 167, respectively). All test samples were tested in 2 independent runs and the reported values are the average of the 2 analysis batches.

For the constructs of SEQ ID NO: 169 and 170, 96-well microtiter plates (Maxisorp, Nunc, Wiesbaden, Germany) were coated overnight at 4° C. with a monoclonal antibody (mAb) against the constructs at 6 µg/mL in PBS. Wells were aspirated and blocked for 1 hour at RT with PBS/1% casein. After this blocking step, wells were washed with PBS-0.05% Tween20. Preparations for the standards, QC samples and dilutions of the test samples were performed in a non-coated (polypropylene) plate.

For the standard curve and QC-samples, solutions at the required concentrations were prepared in PBS 0.1%/casein and spiked into 100% monkey plasma. To prepare standards and QC samples, a 1/100 dilution of the pure monkey plasma dilutions was made in IgM-reducing Agent (Immunochemistry Technologies, Bloomington, USA) supplemented with 2.5% pooled human plasma (referred to as sample diluent).

For the test samples, dilution factors for the test samples were estimated, and ranged between 1/100 to 1/14000. Samples were diluted 1/100 in sample diluent in a first step, and if needed, further dilution was done in sample diluent supplemented with 1% cynomolgus plasma.

Standards, QC samples and diluted test samples were transferred onto the coated plate and incubated for 1 hour at RT. Afterwards the plates were washed followed by a complexation step with purified vWF (ZLB Behring). vWF diluted to 3 µg/ml in PBS/0.1% casein was incubated on the plates for 30 minutes at RT. Plates were washed and Nanobody/vWF complexes bound to the capture tool detected with a Rabbit anti-human vWF Ab (Dako, Denmark), diluted 1/2000 in PBS/0.1% casein and incubated for 30 minutes at RT. After washing, a 1/15000 dilution in PBS/0.1% casein of Horse-Radish-Peroxidase labelled goat anti-rabbit Ab (Dako, Denmark) was added to the plate and incubated for 30 minutes at RT. The enzyme coupled to the Ab catalyzes a chemical reaction with the substrate sTMB (3,3',5,5'-tetramethylbenzidine, SDT reagents, Brussels, Belgium), diluted 1/2 with TMB weakener, SDT reagents) which results in a colorimetric change. After stopping this reaction after 20 minutes using HCl (1N), the intensity of the colour was measured using a spectrophotometer, which determines the optical density of the reaction product, at 450 nm.

The concentrations of each of the constructs of SEQ ID NO: 169 and 170 in the plasma samples were determined based on the parameters of a 4-parameter logistic fit of the standard curve (prepared using the relevant construct). All test samples were tested in 2 independent runs and the reported values are the average of the 2 runs.

For pharmacokinetic data analysis, descriptive statistics (mean and SD) were calculated per dose group and per sampling time point using Microsoft Excel 2007. In case all three values were BQL, BQL was reported. When one or two out of three values were BQL, BQL values were set to zero and the mean calculated. Individual plasma concentration-time profiles were subjected to non-compartmental analysis (NCA) (Model 201; i.v. bolus injection) using WinNonlin Pro 5.1 (Pharsight Corporation, USA; 2006). The area under the curve (AUC) was estimated using the lin up/log down rule. LLOQ values were treated as missing, except when comprised between two values above the LLOQ, then they were set to zero. The concentration at time zero (C0) was estimated through back-calculation based on the two first data points. The terminal elimination half-life ($t^{1/2}$) was calculated automatically (best-fit) using a log-linear regression of the non-zero concentration-time data of the log-linear portion of the terminal phase. A minimum of three points were considered for the determination of λz.

The following main pharmacokinetic parameters were estimated: the plasma concentration at time zero (C0); the area under the plasma concentration-time curve extrapolated to infinity (AUCinf), total body clearance (CL), volume of distribution at steady-state (Vdss), and the dominant half-life ($t_{1/2}$, dominant), and the terminal half-life ($t½$).

In FIG. 10, the mean plasma concentration time profiles of the constructs of SEQ ID NO: 167 (vWF-0053), SEQ ID NO: 169 (vWF-0055), SEQ ID NO: 170 (vWF-0056) and the reference (vWF0001) following an i.v. bolus administration at 2 mg/kg of vWF-0053, vWF-0055, and vWF-0056 (test items) and vWF-0001 (control article), respectively in the male Cynomolgus monkey are presented.

After i.v. injection, the plasma levels of the control article, vWF-0001, dropped rapidly during the first two hours after administration from about 45 ug/ml to ca 2 ug/ml. This initial drop is likely the result of rapid elimination of unbound vWF-0001 by the kidneys. Beyond 2 h post-dose, a slower decline in plasma levels was observed, which is most likely explained by the slower elimination of the vWF0001-vWF complex by the liver.

In the temporal plasma concentration profiles of the various constructs, no such rapid initial decline in plasma levels was apparent. This is likely related to binding of the constructs to monkey albumin, preventing rapid clearance through the kidneys.

In Table X, the main pharmacokinetic parameters of the various constructs and the control vWF0001 in the male Cynomolgus monkey are listed.

TABLE X

Main pharmacokinetic parameters (mean +/− SD; n = 3) of vWF-0053, vWF-0055, and vWF-0056 and vWF0001 following i.v. bolus administration of 2 mg/kg vWF-0053, vWF-0055 and vWF-0056 (test items) or vWF0001 (control article), respectively in the male Cynomolgus monkey.

| Parameter | Units | Mean | SD | Mean | SD |
|---|---|---|---|---|---|
| | | vWF-0053 | | vWF-0055 | |
| C0 | ug/ml | 48.9 | 3.1 | 46.5 | 9.1 |
| AUCinf | ug * h/ml | 1320 | 88 | 1590 | 148 |
| CL | ml/h * kg | 1.52 | 0.10 | 1.26 | 0.12 |
| Vdss | ml/kg | 60.0 | 4.6 | 63.3 | 2.6 |
| t½ dominant | h | 33.2 | 0.30 | 40.5 | 3.9 |

TABLE X-continued

Main pharmacokinetic parameters (mean +/− SD; n = 3) of
vWF-0053, vWF-0055, and vWF-0056 and vWF0001 following
i.v. bolus administration of 2 mg/kg vWF-0053, vWF-0055 and
vWF-0056 (test items) or vWF0001 (control article), respectively
in the male Cynomolgus monkey.

| Parameter | Units | Mean | SD | Mean | SD |
|---|---|---|---|---|---|
| $t_{1/2}$ terminal | h | 31.8 | 2.2 | 27.1 | 2.2 |
| | | vWF-0056 | | vWF-0001 | |
| C0 | ug/ml | 69.4 | 16.2 | 45.3 | 1.3 |
| AUCinf | ug * h/ml | 4140 | 607 | 62.6 | 11.0 |
| CL | ml/h * kg | 0.489 | 0.067 | 32.7 | 5.7 |
| Vdss | ml/kg | 38.5 | 3.1 | 727 | 51 |
| $t_{1/2}$ dominant | h | 75.5 | 7.6 | 0.477 | 0.057 |
| $t_{1/2}$ terminal | h | 30.4 | 7.9 | 22.9 | 3.6 |

Relative to control, the calculated total body clearance (CL) of the constructs was substantially lower. The mean CL of vWF-0053, vWF-0055, and vWF-0056 was decreased 22-, 26-, and 67-fold, respectively compared to the control.

The effect on the Vdss was less pronounced: vWF-0053, vWF-0055, and vWF-0056 had a Vdss-values which were on average 12-, 11-, and 19-fold lower relative to vWF0001.

Relative to vWF0001, the dominant half-life ($t_{1/2}$ dominant) was markedly increased 70-, 85-, 158-fold, respectively for vWF-0053, vWF-0055, and vWF-0056. The terminal half-life ($t_{1/2}$ terminal), which likely reflects elimination of the construct—vWF remained essentially the same (see Table 1).

To evaluate the chemical stability of vWF0055, the Nanobody® vWF0055 was stored at 37° C. After 1, 2 and 4 weeks a sample was taken and analyzed for chemical or proteolytic modifications via RP-HPLC (Zorbax 300SB-C3, 4.6×150 mm (5 μm); trifluoroacetic acid/acetonitrile). These analyses showed that after 4 weeks incubation at 37° C. in D-PBS, neither chemical modifications nor proteolytic degradation occurred (data not shown).

Example 15

Pharmacodynamic Profile and Activity Assays

For the constructs used in Example 14, pharmacodynamic characteristics upon compound administration were measured by means of a ristocetin cofactor activity assay (Biopool). The ristocetin cofactor activity is a functional assay for VWF, measuring the capacity of VWF to interact with the platelet receptor glycoprotein Ib using ristocetin as a modulator.

For pharmacodynamic data analysis, descriptive statistics (mean and SD) were calculated per dose group and per sampling time point using Microsoft Excel 2007. Response parameters and associated statistics for the overall time course were calculated by noncompartmental analysis of the response-time data using WinNonlin Pro 5.1 (Pharsight Corporation, USA; 2006). The non-compartmental analysis was based on a model for pharmacodynamic data (Model 220). The threshold value was set at 20% based on extensive historical PK/PD data on the vWF-0001 compound. Preclinical studies have shown that a complete inhibition of the pharmacodynamic marker are correlated with full antithrombotic efficacy. The following main pharmacodynamic parameters were determined: time below the threshold (Time below T), area under the threshold (AUC below T), time at which the % RICO first drops below the threshold ($T_{onset}$), and time at which the % RICO first returns back above the threshold ($T_{offset}$).

In FIG. 11, the temporal time profiles of the % RICO measurements following an i.v. bolus administration at 2 mg/kg of vWF-0053, vWF-0055, and vWF-0056 (test items) and vWF-0001 (control article), respectively in the male Cynomolgus monkey are shown.

In Table XI, the main pharmacodynamic parameters of the various constructs and the control vWF-0001 in the male Cynomolgus monkey after a single i.v. dose at 2 mg/kg are presented.

TABLE XI

Main pharmacodynamic parameters (mean +/− SD; n = 3) of
vWF-0053, vWF-0055 and vWF-0056 and vWF0001 following
i.v. bolus administration of 2 mg/kg vWF-0053, vWF-0055
and vWF-0056 (test items) or vWF0001 (control article),
respectively in the male Cynomolgus monkey.

| Parameter | Units | Mean | SD | Mean | SD |
|---|---|---|---|---|---|
| | | vWF-0053 | | vWF-0055 | |
| AUC below T | (% RICO * h) | 379 | 291 | 781 | 406 |
| Time below T | (h) | 39.9 | 11.0 | 127 | 26 |
| Tonset | (h) | 0.079 | 0.003 | 0.074 | 0.006 |
| Toffset | (h) | 40.0 | 11.0 | 127 | 26 |
| | | vWF-0056 | | vWF-0001 | |
| AUC below T | (% RICO * h) | 1709 | 945 | 6.60 | 4.35 |
| Time below T | (h) | 202 | 6 | 1.21 | 0.1 |
| Tonset | (h) | 0.079 | 0.003 | 0.077 | 0.002 |
| Toffset | (h) | 202 | 6 | 1.28 | 0.135 |

After i.v. injection, a rapid and comparable onset of action was observed (as evaluated by the % RICO measurements) following i.v. application of both the control article (vWF0001) and the various constructs (vWF-0053, vWF-0055 and vWF-0056). The $T_{onset}$ values were estimated at ca 5 minutes. Compared to control, $T_{offset}$ and hence the time below the threshold (Time below T), and also the AUC under the threshold (AUC below T) were markedly increased after i.v. administration of the constructs.

The time below the threshold after i.v. bolus administration of vWF0001 was on average 1.21 h and had increased 33-, 105-, and 167-fold after application of the respective constructs (vWF-0053, vWF-0055, and vWF-0056).

The mean AUC under the threshold after i.v. bolus administration was 6.60% RICO*h after vWF0001 administration; its value was increased 57-, 118-, and 259-fold after dosing with vWF-0053, vWF-0055, and vWF-0056, respectively.

The activity of the constructs was determined/confirmed in perfusion experiments (see for example Example 16 of WO 04/062551 or Example 4 of WO 06/122825) and a standard inhibition ELISA for measuring inhibition of ristocetin-induced binding of VWF to platelets.

The perfusion experiments were performed with a single-pass perfusion chamber under non-pulsatile flow conditions using a modified small perfusion chamber with a slit height of 0.1 mm and a slit width of 2 mm. Thermanox coverslips (Nunc, Rochester, N.Y.) were coated overnight with 0.5 mg/mL Horm collagen type III (Nycomed) and subsequently blocked with Hepes buffer containing 1% human serum albumin. Citrated human blood was preincubated at 37° C. for 5 min with or without addition of test compound, and then perfused through the chamber for 5 min at a wall shear rate of 1600 s$^{-1}$ using an infusion/withdrawal pump (pump 22, model 2400-004, Harvard Apparatus, Holliston, Mass.). After the perfusion run, the coverslips were rinsed in Hepes buffered saline (10 mM Hepes, 150 mM NaCl, pH 7.4) and platelets were fixed with 5% glutaraldehyde and stained with May-Grünwald and Giemsa. Platelet deposition of the coverslip was evaluated as platelet surface coverage of 10 randomly chosen pictures using light microscopy (Olympus BX61 microscope using Analysis Five digital imaging solutions analysis software).

These results are shown in FIG. 12, and demonstrate that VWF0055, VWF0056 and their non half life extended equivalents dose-dependently and completely inhibit platelet adhesion to fibrillar collagen at arterial shear rate. Effective concentration was similar for VWF0055 and VWF0056 compared to VWF0001.

For determining the inhibition of ristocetin-induced binding of VWF to Platelets, microtiter plates (Maxisorp, Nunc) were coated overnight at 4° C. with 0.1 mg/mL poly-L-Lysine (Sigma, St Louis, Mo.) in PBS. After 3 times washing with phosphate buffered saline (PBS), wells were incubated for 1 hour at room temperature (RT) with formalin fixed human platelets (Dade Behring, Newark, Del.) which were diluted two-fold in PBS or—as a blank—with PBS. Wells were washed 3 times with PBS and blocked for 2 hours at RT with PBS containing 4% bovine serum albumin (BSA, Sigma). A dilution series of compound was prepared in human plasma and was preincubated for 30 min at RT with 1.5 mg/mL ristocetin (abp, NJ, USA) after which the mixture was transferred to the coated wells. After 1.5 hours incubation at 37° C., wells were washed 6 times with PBS and residual bound vWF was detected for 1 hour at RT with a 1/2000 dilution of anti-VWF polyclonal antibodies labeled with horse radish peroxidase (Dako, Glostrup, Denmark). Visualization was obtained with esTMB (SDT reagents, Germany) and the coloring reaction was stopped with 1M hydrochloric acid after which the absorbance was determined at 450 nm. For the analysis of the data, the absorbance values were corrected using the absorbance of the respective blanks.

The results are shown in FIG. 13 and demonstrate that all compounds dose-dependently and completely block the ristocetin-induced binding of VWF to the platelet surface. Similar potency was observed for the expedite constructs compared to the non-half life extended parent. Potency of compounds with 2 VWF binding domains was much higher compared to the potency of a mock variant, in which one of the VWF binding domains was exchanged by an irrelevant Nanobody®. This suggests avid binding of the bivalent compounds to the multimeric VWF and hence confirms functionality of the 2 VWF binding units.

Example 16

Biacore Analysis to Determine pH Dependency of the Binding of vWF0055 to HSA and cynoSA The pH dependent binding of vWF0055 on HSA and cynoSA was investigated by surface plasmon resonance using a Biacore 3000 instrument by assessing the affinity at three different pH's. In brief, HSA and cynoSA were amine-coupled to a separate CM5 sensor chip at a density of respectively 1800RU and 1900RU. Diluted samples, ranging in concentration between 25 nM to 1 μM vW0055 were prepared in three buffers. The three buffers used contained 50 mM phosphate, 150 mM NaCl and 0.005% surfactant P and were adjusted to either pH5, pH7 or pH8. Samples were injected at a flow-rate of 45 μL/min, association and dissociation were monitored during 120 sec and 300 sec. Binding curves were subsequently used to calculate the $K_D$, association- and dissociation-rate constants with the BiaEvaluation software. The highest affinity was observed at pH 7, both for HSA and cynoSA. At pH5 the affinity of vWF0055 was decreased about 10-fold.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

All references disclosed herein are incorporated by reference, in particular for the teaching that is referenced hereinabove.

---

The invention claimed is:

1. An isolated amino acid sequence that:
   a) has at least 50%, but not 100%, sequence identity over the full length of the isolated amino acid sequence with the amino acid sequence

AASYSDYDVFGGGTDFGP;   (SEQ ID NO: 1)

and that:
   b) binds better to human serum albumin than the amino acid sequence

AASYSDYDVFGGGTDFGP.   (SEQ ID NO: 1)

2. An isolated amino acid sequence that:
   a) has no more than 9 amino acid differences over the full length of the isolated amino acid sequence with the amino acid sequence AASYSDYDVFGGGTDFGP (SEQ ID NO:1);
   and that:
   b) binds better to human serum albumin than the amino acid sequence

AASYSDYDVFGGGTDFGP.   (SEQ ID NO: 1)

3. The isolated amino acid sequence according to claim 1, in which, compared to the amino acid sequence of SEQ ID NO.1:
   the serine residue (S) at position 3 of SEQ ID NO:1 is replaced by an amino acid residue chosen from arginine (R), proline (P), phenylalanine (F), tyrosine (Y), tryptophan (W), histidine (H), leucine (L), isoleucine (I), valine (V) or methionine (M);
   and/or
   the serine residue (S) at position 5 of SEQ ID NO:1 is replaced by an amino acid residue chosen from arginine (R), proline (P), phenylalanine (F), tyrosine (Y), tryptophan (W) or histidine (H);
   and/or
   the aspartate residue (D) at position 15 of SEQ ID NO:1 is replaced by an amino acid residue chosen from proline (P), alanine (A), glycine (G), serine (S) or threonine (T);
   and/or
   the phenylalanine residue (F) at position 16 of SEQ ID NO:1 is replaced by proline (P), leucine (L), isoleucine (I), valine (V), methionine (M), alanine (A), glycine (G), serine (S) or threonine (T);
   and/or
   the proline residue (P) at position 18 of SEQ ID NO:1 is maintained or replaced by aspartic acid (D), glutamic acid (E), glutamine (Q), asparagine (N), alanine (A), glycine (G), serine (S) or threonine (T);
   and which amino acid sequence optionally comprises one or more further suitable amino acid insertions, deletions and/or substitutions.

4. The isolated amino acid sequence according to claim 3, in which, compared to the amino acid sequence of SEQ ID NO.1, the serine residue (S) at position 3 of SEQ ID NO:1 is replaced by an arginine (R).

5. The isolated amino acid sequence according to claim 1, that comprises
   (i) an Arg (R) residue, in particular an Arg (R) residue that is capable of forming a hydrogen bond with the amino acid residues Asn (N) 133 & Asn (N) 135 of human serum albumin and/or capable of forming electrostatic interactions with the main-chain oxygen atoms of the Pro (P) 134 and Leu (L) 136 residues of human serum albumin; and/or
   (ii) a Trp (W) residue, in particular a Trp (W) residue that is capable of forming electrostatic interactions with the Arg (R) 138 residue of human serum albumin; and/or
   (iii) the sequence motif GGG;
   and preferably at least any two and more preferably all three of (i), (ii) and (iii).

6. The isolated amino acid sequence according to claim 1, which is one of the amino acid sequences of SEQ ID NO: 14 or 147 to 157, or an amino acid sequence that has not more than 3 amino acid differences over the full length of the isolated amino acid sequence with one of the amino acid sequences of SEQ ID NO: 14 or 147 to 157.

7. An isolated amino acid sequence that:
   a) is the sequence AARYWDYDVFGGGTPVGG (56E4; SEQ ID NO:14); or
   b) has at least 65% sequence identity over the full length of the isolated amino acid sequence with the amino acid sequence AARYWDYDVFGGGTPVGG (56E4; SEQ ID NO:14); and/or
   c) that has no more than 6 amino acid differences over the full length of the isolated amino acid sequence with the amino acid sequence AARYWDYDVFGGGTPVGG (56E4; SEQ ID NO:14)
   and
   d) binds equally well and preferably better to human serum albumin than the amino acid sequence AARYWDYD-VFGGGTPVGG (56E4; SEQ ID NO:14).

8. An isolated amino acid sequence that:
a) is one of the amino acid sequences 59A5 (SEQ ID NO: 147); 59C8 (SEQ ID NO: 148); 59F2 (SEQ ID NO: 149); 59B3 (SEQ ID NO: 150); 59B2 (SEQ ID NO: 151); 60E6 (SEQ ID NO: 152); 60F1 (SEQ ID NO: 153); 60G5 (SEQ ID NO: 154); 59H12 (SEQ ID NO: 155); 59C2 (SEQ ID NO: 156); or 59H10 (SEQ ID NO: 157); or
b) has at least 65% sequence identity over the full length of the isolated amino acid sequence with at least one of the amino acid sequences 59A5 (SEQ ID NO: 147); 59C8 (SEQ ID NO: 148); 59F2 (SEQ ID NO: 149); 59B3 (SEQ ID NO: 150); 59B2 (SEQ ID NO: 151); 60E6 (SEQ ID NO: 152); 60F1 (SEQ ID NO: 153); 60G5 (SEQ ID NO: 154); 59H12 (SEQ ID NO: 155); 59C2 (SEQ ID NO: 156); and/or 59H10 (SEQ ID NO: 157); and/or
c) that has no more than 6 amino acid differences over the full length of the isolated amino acid sequence with at least one of the amino acid sequences 59A5 (SEQ ID NO: 147); 59C8 (SEQ ID NO: 148); 59F2 (SEQ ID NO: 149); 59B3 (SEQ ID NO: 150); 59B2 (SEQ ID NO: 151); 60E6 (SEQ ID NO: 152); 60F1 (SEQ ID NO: 153); 60G5 (SEQ ID NO: 154); 59H12 (SEQ ID NO: 155); 59C2 (SEQ ID NO: 156); and/or 59H10 (SEQ ID NO: 157);

and
d) binds equally well and preferably better to human serum albumin than the amino acid sequence AARYWDYDVFGGGTPVGG (56E4; SEQ ID NO:14).

9. An isolated amino acid sequence that
a) is one of the amino acid sequences 59F2 (SEQ ID NO: 149); 59H12 (SEQ ID NO: 155); or 59C2 (SEQ ID NO: 156); or
b) has at least 65% sequence identity over the full length of the isolated amino acid sequence with at least one of the amino acid sequences 59F2 (SEQ ID NO: 149); 59H12 (SEQ ID NO: 155); and/or 59C2 (SEQ ID NO: 156); and/or
c) that has no more than 6 amino acid differences over the full length of the isolated amino acid sequence with at least one of the amino acid sequences 59F2 (SEQ ID NO: 149); 59H12 (SEQ ID NO: 155); and/or 59C2 (SEQ ID NO: 156);

and
d) binds equally well and preferably better to human serum albumin than the amino acid sequence AARYWDYDVFGGGTPVGG (56E4; SEQ ID NO:14).

10. The isolated amino acid sequence according to claim 1, wherein said amino acid sequence is such that, when it is linked or fused to a therapeutic moiety, compound, protein or other therapeutic entity, the compound thus obtained has a longer half-life than a corresponding compound or construct in which said therapeutic moiety, compound, protein or other therapeutic entity is linked or fused to the amino acid sequence of SEQ ID NO:1; and preferably has a half life that is the same or longer than a corresponding compound or construct in which said therapeutic moiety, compound, protein or other therapeutic entity is linked or fused to the amino acid sequence of SEQ ID NO:14.

11. The isolated amino acid sequence according to claim 1, that is cross-reactive with serum albumin from cynomolgus monkeys (*Macaca fascicularis*).

12. A compound or construct which comprises at least one amino acid sequence according to claim 1 and at least one therapeutic moiety.

13. A compound or construct which comprises at least two amino acid sequences according to claim 1 and at least one therapeutic moiety.

14. A compound or construct which comprises at least one tandem repeat comprising at least two amino acid sequences according to claim 1 and at least one therapeutic moiety.

15. A compound or construct which comprises at least one amino acid sequence according to claim 1 and at least one therapeutic moiety, wherein said compound of the invention has a longer half-life than a corresponding compound that, instead of said amino acid sequence(s), contains the amino acid sequence AASYSDYDVFGGGTDFGP (SEQ ID NO:1); and preferably has an equal or longer half-life than a corresponding compound that, instead of said amino acid sequence(s), contains the amino acid sequence of SEQ ID NO:14.

16. The isolated amino acid sequence according to claim 9, which is a fusion protein or polypeptide.

17. The compound or construct according to claim 12, in which the at least one therapeutic moiety preferably comprises or essentially consists of an immunoglobulin sequence or an antigen-binding fragment thereof, such as an immunoglobulin variable domain or an antigen-binding fragment thereof.

18. The compound or construct according to claim 17, in which the at least one therapeutic moiety preferably comprises or essentially consists of a single domain antibody.

* * * * *